United States Patent
Fujimori

(10) Patent No.: US 9,394,272 B2
(45) Date of Patent: Jul. 19, 2016

(54) 1,3-DIOXANE COMPOUND HAVING FLUORINE ATOM IN AXIAL POSITION, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Sayaka Fujimori, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/742,712

(22) Filed: Jun. 18, 2015

(65) Prior Publication Data

US 2015/0368225 A1    Dec. 24, 2015

(30) Foreign Application Priority Data

Jun. 18, 2014    (JP) .................................. 2014-125670

(51) Int. Cl.

| | |
|---|---|
| G02F 1/1333 | (2006.01) |
| C07D 319/06 | (2006.01) |
| C09K 19/34 | (2006.01) |
| C09K 19/54 | (2006.01) |
| C07D 407/04 | (2006.01) |
| C07D 407/10 | (2006.01) |
| C07D 407/12 | (2006.01) |
| C07D 407/06 | (2006.01) |
| C09K 19/32 | (2006.01) |
| C09K 19/52 | (2006.01) |

(52) U.S. Cl.
CPC ............ *C07D 319/06* (2013.01); *C07D 407/04* (2013.01); *C07D 407/06* (2013.01); *C07D 407/10* (2013.01); *C07D 407/12* (2013.01); *C09K 19/32* (2013.01); *C09K 19/3402* (2013.01); *C09K 19/3458* (2013.01); *C09K 19/52* (2013.01); *C09K 19/542* (2013.01); *C09K 2019/3422* (2013.01); *C09K 2019/3425* (2013.01)

(58) Field of Classification Search
CPC .. C07D 319/06; C07D 407/04; C07D 407/10; C07D 407/12; C09K 19/3458; C09K 19/3402; C09K 19/542; C09K 19/32; C09K 19/52; C09K 2019/3422; C09K 2019/3425; G02F 1/1333
USPC ............... 252/299.01, 299.6, 299.61, 299.63; 428/1.1; 349/182; 549/369, 370, 372, 549/374
See application file for complete search history.

(56) References Cited

U.S. PATENT DOCUMENTS 5,961,880 A    10/1999    Kirsch et al.

FOREIGN PATENT DOCUMENTS

| | | |
|---|---|---|
| EP | 0930288 | 7/1999 |
| JP | H11-012271 | 1/1999 |
| WO | 9814418 | 4/1998 |

OTHER PUBLICATIONS

Kirsch et al., "Liquid Crystals Based on Axially Fluorinated 1,3-Dioxanes: Synthesis, Properties and Computational Study", European Journal of Organic Chemistry, Nov. 2006, vol. 21, pp. 4819-4824.

*Primary Examiner* — Geraldina Visconti
(74) *Attorney, Agent, or Firm* — Jianq Chyun IP Office

(57) ABSTRACT

A liquid-crystal compound satisfying at least one physical property such as a high clearing point, large dielectric anisotropy and excellent compatibility with other liquid-crystal compounds is described; a liquid-crystal composition containing the compound; and a liquid-crystal display device. The compound is represented by formula (1):

$$R^1 \underset{O}{\overset{F}{\diagdown}} O \diagdown \left( Z^1 - A^1 \right)_a \left( Z^2 - A^2 \right)_b \left( Z^3 - A^3 \right)_c R^2 \quad (1)$$

wherein, $R^1$ and $R^2$ are independently alkyl having 1 to 15 carbons, and in the alkyl, at least one $—CH_2—$ may be replaced by $—O—$, $—CH{=}CH—$ or the like;
ring $A^1$, ring $A^2$ and ring $A^3$ are independently 1,4-cyclohexylene, 1,4-phenylene or the like, and at least one ring $A^1$, ring $A^2$ or ring $A^3$ is represented by formula (A):

$$\text{(A)}$$

wherein, $X^1$ and $X^2$ are independently hydrogen or halogen; and
$Z^1$, $Z^2$ and $Z^3$ are independently a single bond, $—(CH_2)_2—$ or the like; and
a, b and c are independently 0 or 1, and a sum of a, b and c is 1, 2 or 3.

12 Claims, No Drawings

1,3-DIOXANE COMPOUND HAVING FLUORINE ATOM IN AXIAL POSITION, LIQUID CRYSTAL COMPOSITION AND LIQUID CRYSTAL DISPLAY DEVICE

CROSS-REFERENCE TO RELATED APPLICATION

This application claims the priority benefit of Japan application no. 2014-125670, filed on Jun. 18, 2014. The entirety of each of the above-mentioned patent application is hereby incorporated by reference herein and made a part of this specification.

TECHNICAL FIELD

The invention relates to a liquid crystal compound, a liquid crystal composition and a liquid crystal display device. More specifically, the invention relates to a compound that has a 1,3-dioxane skeleton having a fluorine atom in an axial position and ring structure bonded therewith and has a negative dielectric anisotropy, a liquid crystal composition containing the compound, and a liquid crystal display device including the composition.

BACKGROUND ART

A liquid crystal display device gas been widely utilized for a display of a personal computer, television or the like. The device utilizes optical anisotropy, dielectric anisotropy and so forth of a liquid crystal compound. As an operating mode of the liquid crystal display device, such modes are known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

Among the modes, the IPS mode, the FFS mode and the VA mode are known to allow improvement in narrowness of a viewing angle being a disadvantage of the operating mode such as the TN mode and the STN mode. In the liquid crystal display device having the mode of the kind, a liquid crystal composition having a negative dielectric anisotropy is mainly used. In order to further improve characteristics of the liquid crystal display device, the liquid crystal compound contained in the composition preferably has physical properties described in (1) to (8) below:
(1) high stability to heat, light and so forth;
(2) a high clearing point;
(3) low minimum temperature of a liquid crystal phase;
(4) small viscosity ($\eta$);
(5) suitable optical anisotropy ($\Delta n$);
(6) large negative dielectric anisotropy ($\Delta \in$);
(7) a suitable elastic constant ($K_{33}$: bend elastic constant); and
(8) excellent compatibility with other liquid crystal compounds.

An effect of the physical properties of the liquid crystal compound on the characteristics of the device is as described below. A compound having the high stability to heat, light and so forth as described in (1) increases a voltage holding ratio of the device. Thus, a service life of the device becomes long. A compound having the high clearing point as described in (2) extends a temperature range in which the device can be used. A compound having the low minimum temperature of the liquid crystal phase such as a nematic phase and a smectic phase, as described in (3), in particular, a compound having the low minimum temperature of the nematic phase, also extends the temperature range in which the device can be used. A compound having the small viscosity as described in (4) shortens a response time of the device.

A compound having the suitable optical anisotropy as described in (5) improves contrast of the device. According to a design of the device, a compound having a large optical anisotropy or small optical anisotropy, more specifically, a compound having the suitable optical anisotropy, is required. When the response time is shortened by decreasing a cell gap of the device, a compound having the large optical anisotropy is suitable. A compound having the large negative dielectric anisotropy as described in (6) decreases a threshold voltage of the device. Thus, an electric power consumption of the device is decreased.

With regard to (7), a compound having a large elastic constant shortens the response time of the device. A compound having a small elastic constant decreases the threshold voltage of the device. Therefore, the suitable elastic constant is required according to the characteristics to be desirably improved. A compound having the excellent compatibility with other liquid crystal compounds as described in (8) is preferred. The reason is that the physical properties of the composition are adjusted by mixing liquid crystal compounds having different physical properties.

A variety of liquid crystal compounds having the negative dielectric anisotropy have so far been prepared (Patent literature No. 1 and Patent literature No. 2, or Non-patent literature No. 1, for example). Patent literature No. 2 and Non-patent literature No. 1 show compound (C-1). However, compound (C-1) has no sufficiently high compatibility with other compounds.

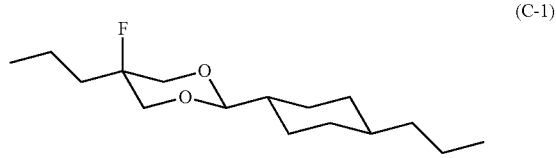 [SMILES: CCCC1CCC(C2OCC(F)(CCC)CO2)CC1]

(C-1)

Moreover, Patent literature No. 1 shows compound (C-2). However, compound (C-2) has no high clearing point and shows no sufficiently large negative dielectric anisotropy.

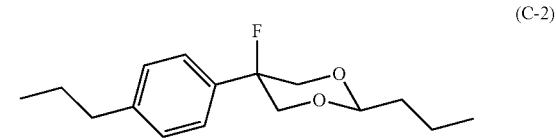 [SMILES: CCCc1ccc(C2(F)COC(CCC)OC2)cc1]

(C-2)

From such a circumstance, development has been desired for a compound having excellent physical properties and a suitable balance with regard to the physical properties (1) to (8) described above, in particular, for a compound having a high compatibility with other compounds and showing the large negative dielectric anisotropy.

CITATION LIST

Patent Literature

Patent literature No. 1: WO 1998/014418 A.
Patent literature No. 2: JP H11-12271 A.

Non-Patent Literature

Non-patent literature No. 1: Eur. J. Org. Chem. 2006, 4819-4824.

SUMMARY OF INVENTION

Technical Problem

This invention provides a liquid crystal compound satisfying at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. In particular, this invention provides a compound having a large negative dielectric anisotropy, a high clearing point and a high compatibility with other compounds. This invention also provides a liquid crystal composition that contains the compound and satisfies at least one of physical properties such as a high maximum temperature of a nematic phase, a low minimum temperature of the nematic phase, a small viscosity, a suitable optical anisotropy, a large negative dielectric anisotropy and a suitable elastic constant. This invention provides a liquid crystal composition having a suitable balance regarding at least two of the physical properties. This invention further provides a liquid crystal display device that includes the composition and has a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition:

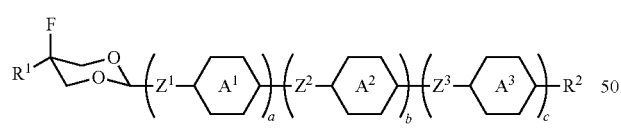

(1)

wherein, in formula (1), $R^1$ and $R^2$ are independently alkyl having 1 to 15 carbons, and in the alkyl, at least one of —$CH_2$— may be replaced by —O— or —S—, and at least one of —$(CH_2)_2$— may be replaced by —CH=CH—;

ring $A^1$, ring $A^2$ and ring $A^3$ are independently 1,4-cyclohexylene, 1,4-phenylene, 1,4-phenylene in which at least one of hydrogen is replaced by halogen, tetrahydropyran-2,5-diyl, or tetrahydropyran-2,5-diyl in which at least one of hydrogen is replaced by halogen, and in the rings, at least one of —$(CH_2)_2$— may be replaced by —CH=CH—, and at least one of ring $A^1$, ring $A^2$ and ring $A^3$ is represented by formula (A):

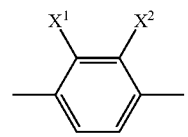

(A)

wherein, $X^1$ and $X^2$ are independently hydrogen or halogen; and $Z^1$, $Z^2$ and $Z^3$ are independently a single bond, —$(CH_2)_2$—, —CH=CH—, —C≡C—, —COO—, —OCO—, —$CH_2O$—, —$OCH_2$—, —$CF_2O$—, —$OCF_2$— or —CF=CF—; and a, b and c are independently 0 or 1, and a sum of a, b and c is 1, 2 or 3.

The invention also concerns use of at least one compound as a component of a liquid crystal composition.

The compound represented by formula (1) has ring structure on a side of an oxygen atom of a 1,3-dioxane skeleton having a fluorine atom in an axial position, and thus has a large negative dielectric anisotropy and a high clearing point.

Advantageous Effects of Invention

A first advantage of the invention is to provide a liquid crystal compound satisfying at least one of physical properties such as a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. A characteristic advantage among the physical properties described above is to provide a compound having a large negative dielectric anisotropy, a high clearing point and a high compatibility with other compounds. A second advantage of the invention is to provide a liquid crystal composition that contains the compound and satisfies at least one of physical properties such as a high maximum temperature of a nematic phase, a low minimum temperature of the nematic phase, a small viscosity, a suitable optical anisotropy, a large negative dielectric anisotropy and a suitable elastic constant. A third advantage of the invention is to provide a liquid crystal display device that includes the composition and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase or a smectic phase, and also for a compound having no liquid crystal phases but being useful as a component for a liquid crystal composition. The liquid crystal compound, the liquid crystal composition and a liquid crystal display device may be occasionally abbreviated as "compound," "composition" and "device," respectively. The liquid crystal display device is a generic term for a liquid crystal display panel and a liquid crystal display module. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as "maximum temperature." A minimum temperature of the nematic phase may be occasionally abbreviated as "minimum temperature." "Compound represented by formula (1)" may be occasionally abbreviated as "compound (1)." The abbreviation may also apply to a compound represented by formula (2) or the like. In formula (1), formula (2) or the like, a symbol $A^1$, $D^1$ or the like surrounded by a hexagonal shape corresponds to ring $A^1$, ring $D^1$ or the like, respectively. A plurality of ring $A^1$ are described in one formula or different formulas. In the compounds, two groups represented by two of arbitrary ring $A^1$ may be identical or different. A same rule also applies to a symbol of ring $A^2$, $Z^2$ or the like. Moreover, a same rule also applies to two of ring $A^1$ when 1 is 2. An amount of the compound expressed in terms of "percent" is expressed in terms of "weight percent (% by weight)" based on the total weight of the composition.

An expression "at least one of "A" may be replaced by "B" means that a position of "A" is arbitrary when the number of "A" is 1, and also when the number of "A" is two or more, positions thereof can be selected without restriction. An expression "at least one of A may be replaced by B, C or D" means inclusion of a case where arbitrary A is replaced by B, a case where arbitrary A is replaced by C, and a case where arbitrary A is replaced by D, and also a case where a plurality of A are replaced by at least two of B, C or D. For example, alkyl in which at least one of —CH$_2$— may be replaced by —O— or —CH═CH— includes alkyl, alkenyl, alkoxy, alkoxyalkyl, alkoxyalkenyl and alkenyloxyalkyl. In addition, replacement of two consecutive —CH$_2$— by —O— to form —O—O— is not preferred. In alkyl or the like, replacement of —CH$_2$— of a methyl part (—CH$_2$—H) by —O— to form. —O—H is not preferred, either.

Then, 2-fluoro-1,4-phenylene means two divalent groups described below. Fluorine may be leftward or rightward. A same rule also applies to a divalent group of an asymmetrical ring such as tetrahydropyran-2,5-diyl.

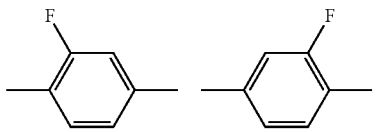

The invention includes the content described in items 1 to 13 below.

Item 1. A compound represented by formula (1):

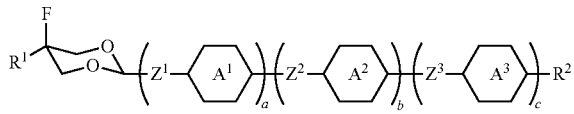

wherein, in formula (1), $R^1$ and $R^2$ are independently alkyl having 1 to 15 carbons, and in the alkyl, at least one of —CH$_2$— may be replaced by —O— or —S—, and at least one of —(CH$_2$)$_2$— may be replaced by —CH═CH—;

ring $A^1$, ring $A^2$ and ring $A^3$ are independently 1,4-cyclohexylene, 1,4-phenylene, 1,4-phenylene in which at least one of hydrogen is replaced by halogen, tetrahydropyran-2,5-diyl, or tetrahydropyran-2,5-diyl in which at least one of hydrogen is replaced by halogen, and in the rings, at least one of —(CH$_2$)$_2$— may be replaced by —CH═CH—, and at least one of ring $A^1$, ring $A^2$ and ring $A^3$ is represented by formula (A):

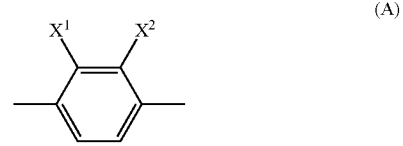

wherein,
$X^1$ and $X^2$ are independently hydrogen or halogen; and
$Z^1$, $Z^2$ and $Z^3$ are independently a single bond, —(CH$_2$)$_2$—, —CH═CH—, —C≡C—, —COO—, —OCO—, —CH$_2$O—, —OCH$_2$—, —CF$_2$O—, —OCF$_2$— or —CF═CF—; and
a, b and c are independently 0 or 1, and a sum of a, b and c is 1, 2 or 3.

Item 2. The compound according to item 1, represented by formulas (1-1) to (1-3):

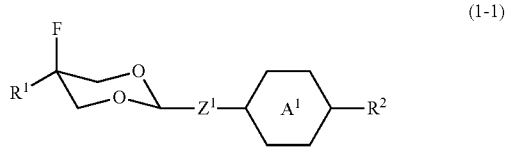

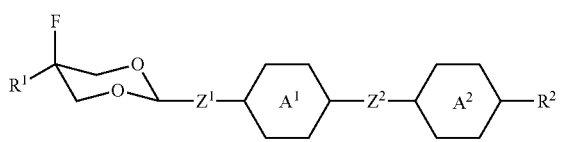

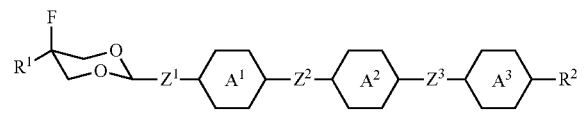

wherein, in formulas (1-1) to (1-3),
$R^1$ and $R^2$ are independently alkyl having 1 to 15 carbons, alkoxy having 1 to 14 carbons, alkenyl having 2 to 15 carbons and alkenyloxy having 2 to 14 carbons;
ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by halogen, tetrahydropyran-2,5-diyl or dihydropyrane-2,5-diyl, but at least one is a ring represented by formula (A):

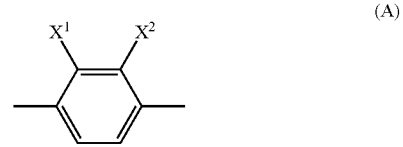

wherein,
$X^1$ and $X^2$ are independently hydrogen or fluorine; and
$Z^1$, $Z^2$ and $Z^3$ are independently a single bond, —(CH$_2$)$_2$—, —CH═CH—, —COO—, —OCO—, —CH$_2$O—, —OCH$_2$—, —CF$_2$O— or —OCF$_2$—.

Item 3. The compound according to item 1, wherein $R^1$ and $R^2$ are independently alkyl having 1 to 15 carbons, alkoxy having 1 to 14 carbons, alkenyl having 2 to 15 carbons and alkenyloxy having 2 to 14 carbons, ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl or dihydropyrane-2,5-diyl, but at least one is a ring represented by formula (A)

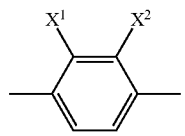
(A)

wherein, $X^1$ and $X^2$ are independently hydrogen or fluorine; and $Z^1$, $Z^2$ and $Z^3$ are independently a single bond, —(CH$_2$)$_2$—, —CH=CH—, —CH$_2$O— or —OCH$_2$—.

Item 4. The compound according to item 1, wherein, in the case where both $X^1$ and $X^2$ are fluorine when ring $A^1$ is represented by formula (A):

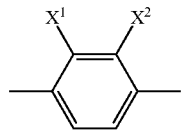
(A)

$Z^1$ is —(CH$_2$)$_2$—, —CH=CH—, —CH$_2$O— or —OCH$_2$—.

Item 5. The compound according to item 1, represented by formula (1-1-a), formula (1-1-b), formulas (1-2-a) to (1-2-k), formula (1-2-m), formulas (1-3-a) to (1-3-k) and formulas (1-3-m) to (1-3-t):

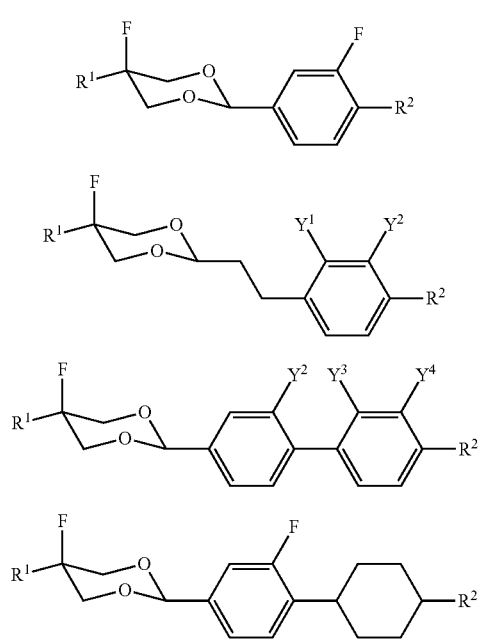

-continued

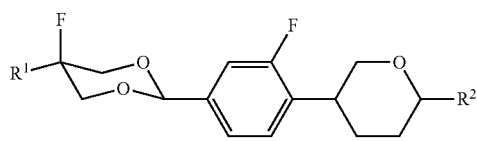
(1-2-c)

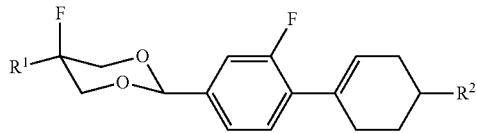
(1-2-d)

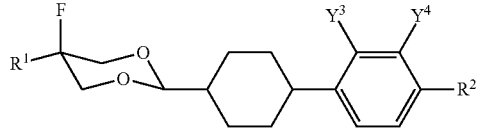
(1-2-e)

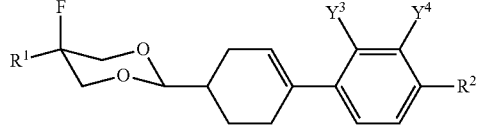
(1-2-f)

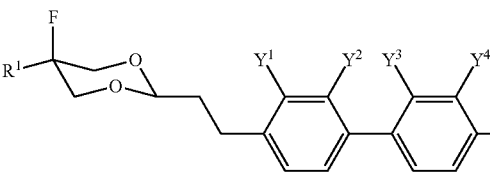
(1-2-g)

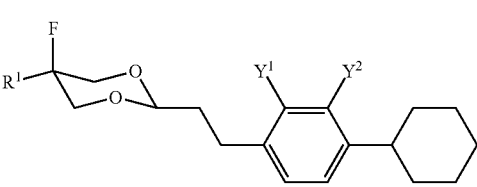
(1-2-h)

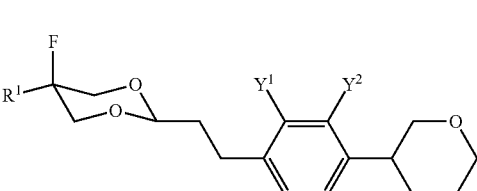
(1-2-i)

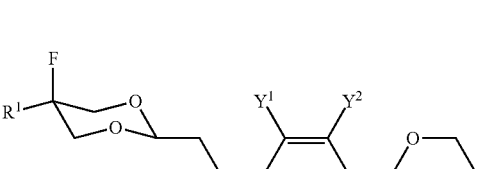
(1-2-j)

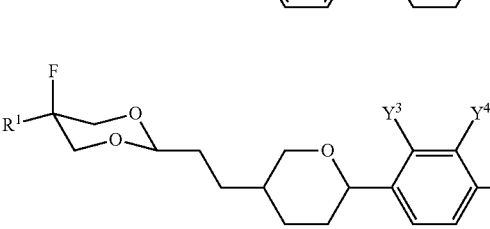
(1-2-k)

(1-2-m)
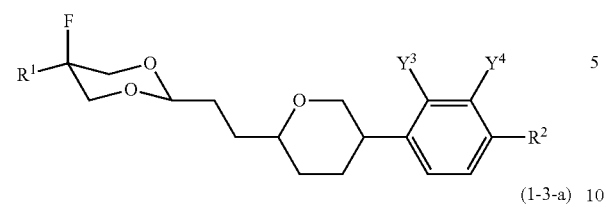
(1-3-a)
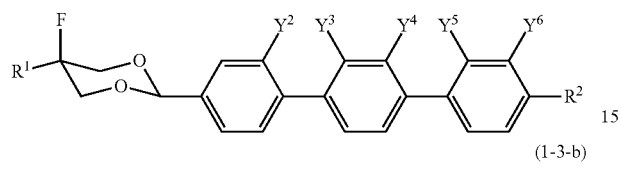
(1-3-b)
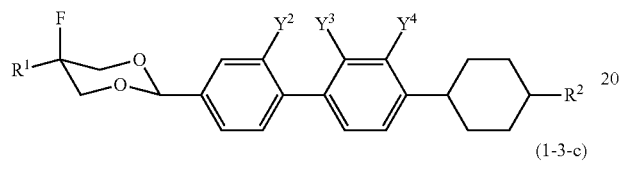
(1-3-c)
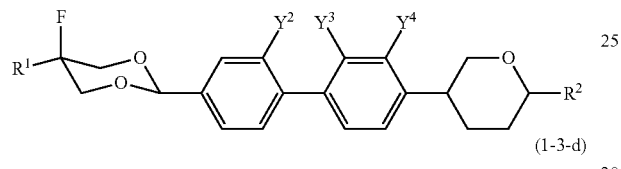
(1-3-d)
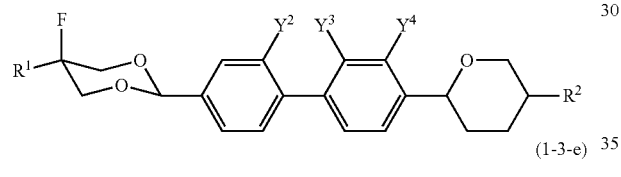
(1-3-e)
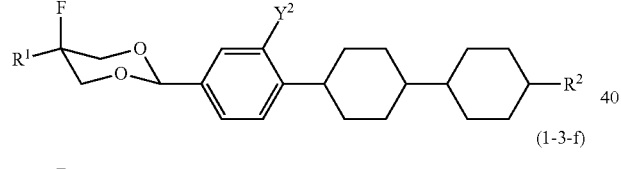
(1-3-f)
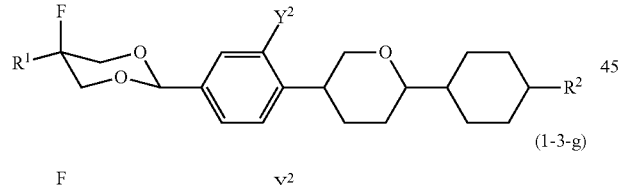
(1-3-g)
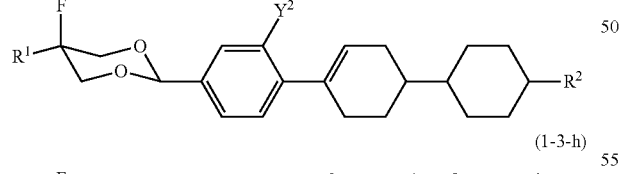
(1-3-h)
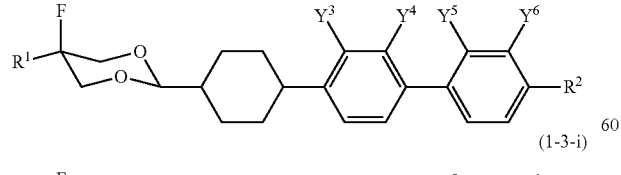
(1-3-i)
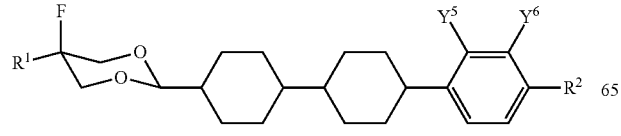
(1-3-j)
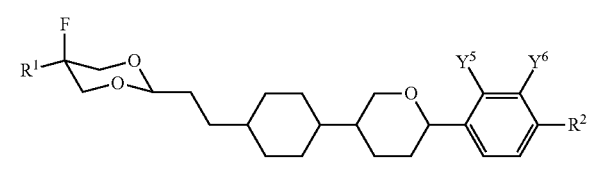
(1-3-k)
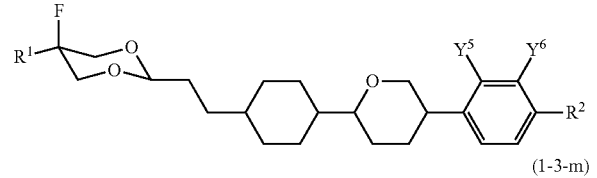
(1-3-m)
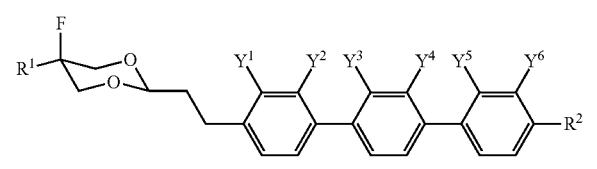
(1-3-n)
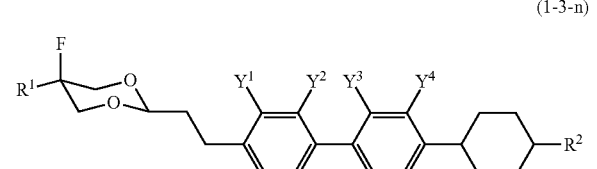
(1-3-o)
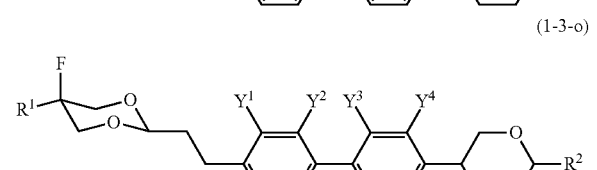
(1-3-p)
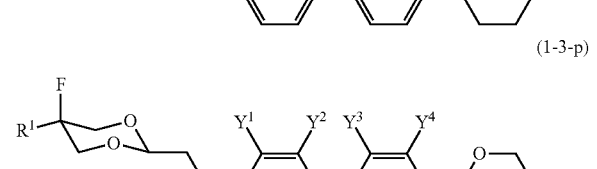
(1-3-q)
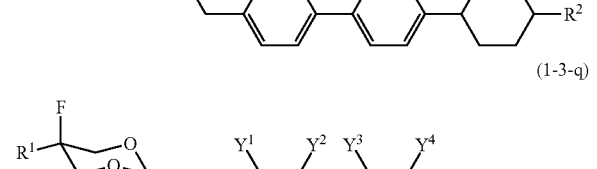
(1-3-r)
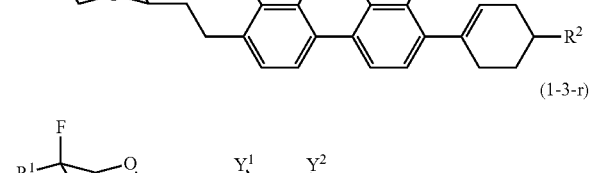
(1-3-s)
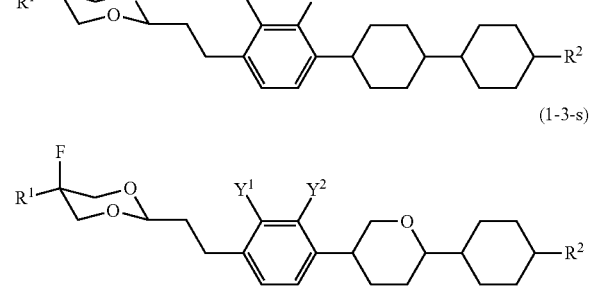

-continued (1-3-t)
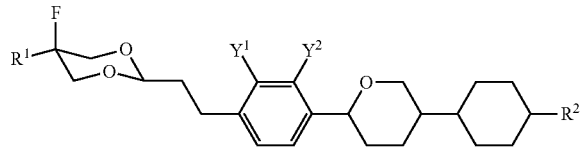

wherein, in formula (1-1-a), formula (1-1-b), formulas (1-2-a) to (1-2-k), formula (1-2-m), formulas (1-3-a) to (1-3-k) and formulas (1-3-m) to (1-3-t), $R^1$ and $R^2$ are independently alkyl having 1 to 10 carbons, alkoxy having 1 to 9 carbons, alkenyl having 2 to 10 carbons and alkenyloxy having 2 to 9 carbons; and $Y^1$ to $Y^6$ are independently hydrogen or fluorine.

Item 6. Use of at least one compound according to anyone of items 1 to 5 as a component of a liquid crystal composition.

Item 7. A liquid crystal composition, containing at least one compound according to any one of items 1 to 5.

Item 8. The liquid crystal composition according to item 7, further containing at least one compound selected from the group of compounds represented by formulas (6) to (12):

—$CH_2$— may be replaced by —O—, and at least one of hydrogen may be replaced by fluorine;

$R^{14}$ is alkyl having 1 to 10 carbons, and in the alkyl, at least one of —$CH_2$— may be replaced by —O—, and at least one of hydrogen may be replaced by fluorine;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$S^{11}$ b is hydrogen or methyl;

$X^1$ and $X^2$ are independently —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

(6)
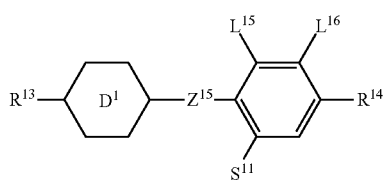

(7)
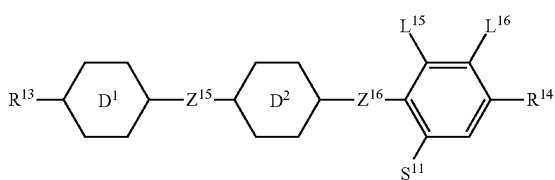

(8)
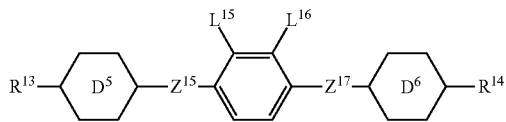

(9)
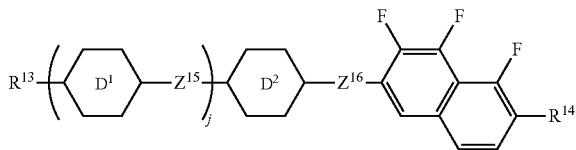

(10)
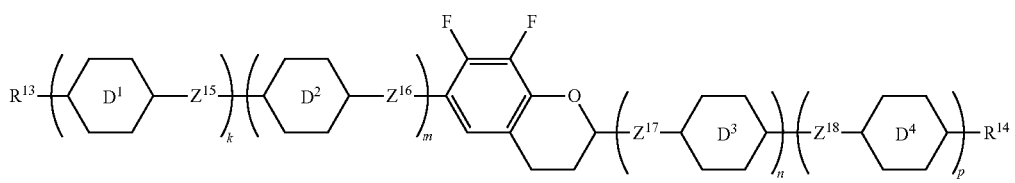

(11)
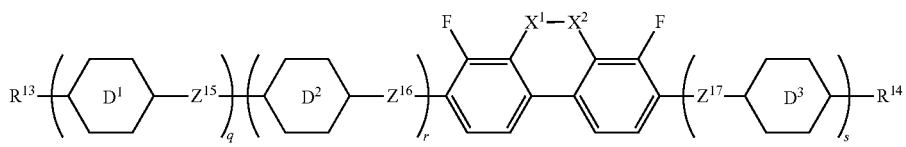

(12)
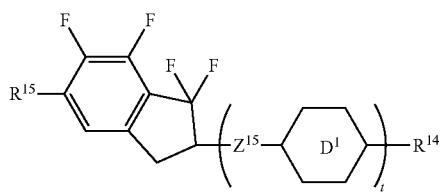

wherein, in formulas (6) to (12), $R^{13}$ is alkyl having 1 to 10 carbons or alkenyl having 2 to 10 carbons, and in the alkyl and the alkenyl, at least one of $L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 9. The liquid crystal composition according to item 7 or 8, further containing at least one compound selected from the group of compounds represented by formulas (13) to (15):

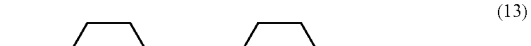
(13)

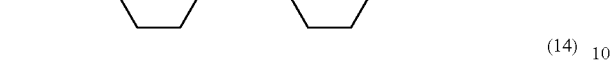
(14)

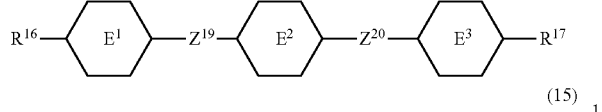
(15)

wherein, in formulas (13) to (15), $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, —C≡C— or —COO—.

Item 10. The liquid crystal composition according to any one of items 7 to 9, further containing at least one compound selected from the group of compounds represented by formulas (2) to (4):

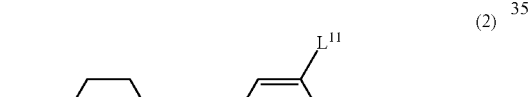
(2)

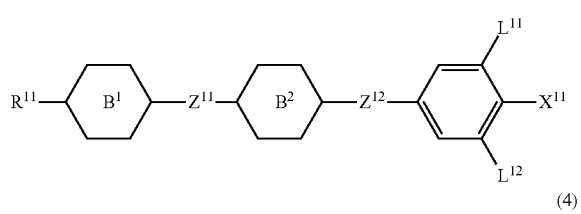
(3)

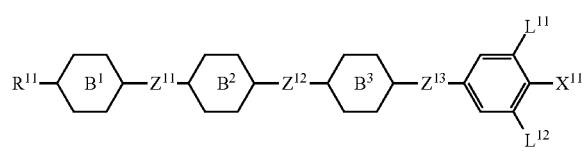
(4)

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one of hydrogen is replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 11. The liquid crystal composition according to any one of items 7 to 10, further containing at least one compound selected from the group of compounds represented by formula (5):

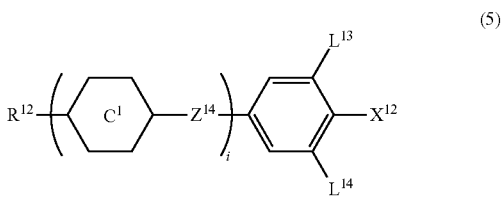
(5)

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{12}$ is —C≡N or —C≡C—C≡N;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 12. The liquid crystal composition according to any one of items 7 to 11, further containing at least one optically active compound and/or polymerizable compound.

Item 13. The liquid crystal composition according to any one of items 7 to 12, further containing at least one antioxidant and/or ultraviolet light absorber.

Item 14. A liquid crystal display device, including the liquid crystal composition according to any one of items 7 to 13.

The compound, the liquid crystal composition and the liquid crystal display device of the invention will be described in the order.

1-1. Compound (1)

Compound (1) of the invention will be described. Preferred examples of a terminal group, ring structure, a bonding group or the like in compound (1), and an effect of the groups on physical properties also apply to a subordinate formula of formula (1) for compound (1).

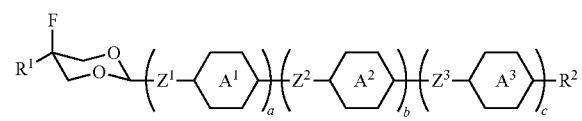
(1)

In formula (1), $R^1$ and $R^2$ are independently alkyl having 1 to 15 carbons, and in the alkyl, at least one of —$CH_2$— may be replaced by —O— or —S—, and at least one —$(CH_2)_2$— may be replaced by —CH=CH—. The groups have a straight chain or a branched chain, and include no cyclic group such as cyclohexyl. In the groups, the straight chain is preferred to the branched chain.

A preferred configuration of —CH═CH— in alkenyl depends on a position of a double bond. A trans configuration is preferred in alkenyl having the double bond in an odd-numbered position, such as —CH═CHCH$_3$, —CH═CHC$_2$H$_5$, —CH═CHC$_3$H$_7$, —CH═CHC$_4$H$_9$, —C$_2$H$_4$CH═CHCH$_3$ and —C$_2$H$_4$CH═CHC$_2$H$_5$. A cis configuration is preferred in alkenyl having the double bond in an even-numbered position, such as —CH$_2$CH═CHCH$_3$, —CH$_2$CH═CHC$_2$H$_5$ and —CH$_2$CH═CHC$_3$H$_7$. An alkenyl compound having the preferred configuration has a high clearing point or a wide temperature range of the liquid crystal phase. A detailed description is found in Mol. Cryst. Liq. Cryst., 1985, 131, P 109 and Mol. Cryst. Liq. Cryst., 1985, 131, P327.

Preferred examples of $R^1$ and $R^2$ include alkyl, alkoxy, alkenyl and alkenyloxy. Further preferred examples of $R^1$ and $R^2$ include alkyl, alkoxy and alkenyl. Most preferred examples of $R^1$ and $R^2$ include alkyl and alkoxy.

Examples of alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Examples of alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Examples of alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Examples of alkenyl include —CH═CH$_2$, —CH═CHCH$_3$, —CH$_2$CH═CH$_2$, —CH═CHC$_2$H$_5$, —CH$_2$CH═CHCH$_3$, —(CH$_2$)$_2$—CH═CH$_2$, —CH═CHC$_3$H$_7$, —CH$_2$CH═CHC$_2$H$_5$, —(CH$_2$)$_2$—CH═CHCH$_3$ and —(CH$_2$)$_3$—CH═CH$_2$.

Examples of alkenyloxy include —OCH$_2$CH═CH$_2$, —OCH$_2$CH═CHCH$_3$ and —OCH$_2$CH═CHC$_2$H$_5$.

In formula (1), ring $A^1$, ring $A^2$ and ring $A^3$ are independently 1,4-cyclohexylene, 1,4-phenylene, 1,4-phenylene in which at least one of hydrogen is replaced by halogen, tetrahydropyran-2,5-diyl, or tetrahydropyran-2,5-diyl in which at least one of hydrogen is replaced by halogen, and in the rings, at least one of —(CH$_2$)$_2$— may be replaced by —CH═CH—, and at least one of ring $A^1$, ring $A^2$ and ring $A^3$ is represented by formula (A):

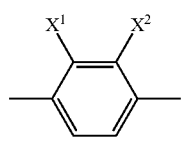

(A)

wherein, $X^1$ and $X^2$ are independently hydrogen or halogen.

Preferred examples of ring $A^1$, ring $A^2$ and ring $A^3$ include 1,4-cyclohexylene, 1,4-cyclohexenylene, 1,4-phenylene, 2-fluoro-1,4-phenylene, 2,3-difluoro-1,4-phenylene, tetrahydropyran-2,5-diyl or dihydropyrane-2,5-diyl, but at least one is a ring represented by formula (A):

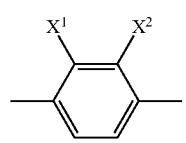

(A)

wherein, $X^1$ and $X^2$ are independently hydrogen or fluorine. Cis and trans configurations exist in 1,4-cyclohexylene. From a viewpoint of a high maximum temperature, the trans configuration is preferred.

Preferred examples of 1,4-phenylene in which at least one of hydrogen is replaced by halogen include rings (A-1) to (A-17). In order to have a large negative dielectric anisotropy, rings (A-1), (A-5), (A-6), (A-7), (A-8), (A-9), (A-10) and (A-11) are further preferred. Most preferred examples of 1,4-phenylene in which at least one of hydrogen is replaced by halogen include ring (A-1) and ring (A-6).

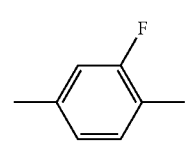

(A-1)

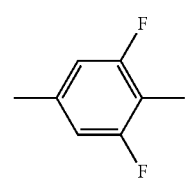

(A-2)

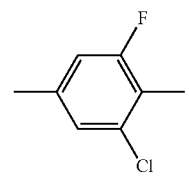

(A-3)

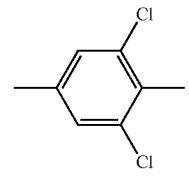

(A-4)

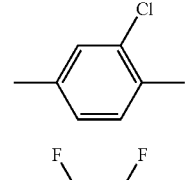

(A-5)

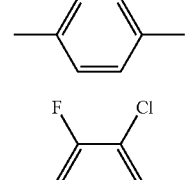

(A-6)

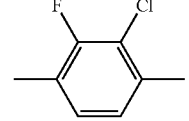

(A-7)

(A-8) 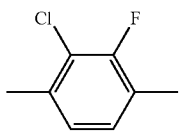

(A-9) 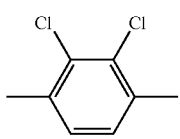

(A-10) 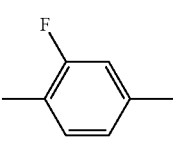

(A-11) 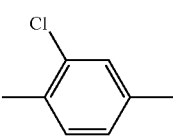

(A-12) 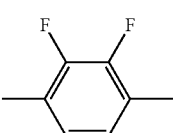

(A-13) 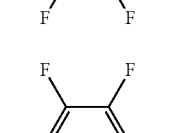

(A-14) 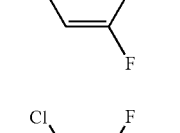

(A-15) 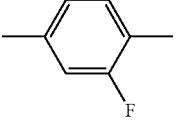

(A-16) 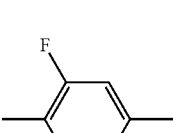

(A-17) 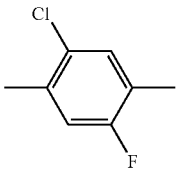

$Z^1$, $Z^2$ and $Z^3$ are independently a single bond, —(CH$_2$)$_2$—, —CH=CH—, —C≡C—, —COO—, —OCO—, —CH$_2$O—, —OCH$_2$—, —CF$_2$O—, —OCF$_2$— or —CF=CF—. Preferred examples of $Z^1$, $Z^2$ and $Z^3$ include a single bond, —(CH$_2$)$_2$—, —CH=CH—, —COO—, —OCO—, —CH$_2$O—, —OCH$_2$—, —CF$_2$O— or —OCF$_2$—. Further preferred examples include a single bond, —(CH$_2$)$_2$—, —CH=CH—, —CH$_2$O— or —OCH$_2$—. Most preferred examples of $Z^1$, $Z^2$ and $Z^3$ include a single bond, —(CH$_2$)$_2$—, —CH$_2$O— or —OCH$_2$—.

When ring $A^1$ is 2,3-difluoro-1,4-phenylene, $Z^1$ is preferably —(CH$_2$)$_2$—, —CH=CH—, —C≡C—, —COO—, —OCO—, —CH$_2$O—, —OCH$_2$—, —CF$_2$O—, —OCF$_2$— or —CF=CF—.

In formula (1), a, b and c are independently 0 or 1, and a sum of a, b and c is 1, 2 or 3. Examples of preferred combinations of a, b and c include a combination (a=1, b=0, c=0) and a combination (a=1, b=1, c=0).

1-2. Physical Properties of Compound (1)

In compound (1), physical properties such as a clearing point, optical anisotropy and dielectric anisotropy can be arbitrarily adjusted by suitably selecting a kind of $R^1$, $R^2$, ring $A^1$, ring $A^2$, $Z^1$ and $Z^2$, and a combination of a and b. Compound (1) may contain an isotope such as $^2$H (deuterium) and $^{13}$C in an amount larger than an amount of natural abundance because no significant difference exists in the physical properties of the compound. A main effect of kinds of $R^1$ or the like on the physical properties of compound (1) will be described below.

When $R^1$ or $R^2$ has a straight chain, the temperature range of the liquid crystal phase is wide and the viscosity is small. When $R^1$ or $R^2$ has a branched chain, compatibility with other liquid crystal compounds is good. A compound in which $R^1$ or $R^2$ is optically active is useful as a chiral dopant. A reverse twisted domain to be generated in the liquid crystal display device can be prevented by adding the compound to the composition. A compound in which both of $R^1$ and $R^2$ are not optically active is useful as a component of the composition. When $R^1$ or $R^2$ is alkenyl, a preferred configuration depends on the position of the double bond. An alkenyl compound having the preferred configuration has a small viscosity, the high maximum temperature or the wide temperature range of the liquid crystal phase. When $R^1$ or $R^2$ is alkoxy, the alkenyl compound has the high maximum temperature.

When at least one of ring $A^1$, ring $A^2$ and ring $A^3$ is 1,4-phenylene, or 1,4-phenylene in which at least one of hydrogen is replaced by halogen, the optical anisotropy is comparatively large and an orientational order parameter is comparatively large. When ring $A^1$, ring $A^2$ and ring $A^3$ are 1,4-phenylene, 1,4-phenylene in which at least one of hydrogen is replaced by halogen, or a combination thereof, the optical anisotropy is particularly large. When at least one of ring $A^1$, ring $A^2$ and ring $A^3$ is 2-fluoro-1,4-phenylene, 2-chloro-1,4-phenylene, 2,3-difluoro-1,4-phenylene, 2,3-dichloro-1,4-phenylene, 2-chloro-3-fluoro-1,4-phenylene, tetrahydropyran-2,5-diyl or dihydropyrane-2,5-diyl, the negative dielectric anisotropy is particularly large.

When at least one of $Z^1$, $Z^2$ and $Z^3$ is a single bond, —CH$_2$CH$_2$—, —CH=CH—, —CF$_2$O— or —OCF$_2$—, the viscosity is small. When at least one of $Z^1$, $Z^2$ and $Z^3$ is —CH=CH—, —CH$_2$O— or —OCH$_2$—, the temperature range of the liquid crystal phase is wide, and an elastic constant (K) is large. When at least one of $Z^1$, $Z^2$ and $Z^3$ is a single bond, —CH=CH—, —C≡C—, —COO—, —OCO— or —CF=CF—, the clearing point is high. When at least one of $Z^1$, $Z^2$ and $Z^3$ is —CH=CH—, —C≡C— or —CF=CF—, the optical anisotropy is large. When at least one of $Z^1$, $Z^2$ and $Z^3$ is —CH$_2$O— or —OCH$_2$—, the negative dielectric anisotropy is large. When all of $Z^1$, $Z^2$ and $Z^3$ are a single bond, —CH$_2$CH$_2$—, —CH$_2$O— or —OCH$_2$—, chemical stability is high.

When combinations of a, b and c include (a=1, b=0, c=0), (a=1, b=1, c=0) or (a=1, b=1, c=1), and at least one of ring A$^1$, ring A$^2$ and ring A$^3$ is 2-fluoro-1,4-phenylene, 2-chloro-1,4-phenylene, 2,3-difluoro-1,4-phenylene, 2,3-dichloro-1,4-phenylene, 2-chloro-3-fluoro-1,4-phenylene, tetrahydropyran-2,5-diyl or dihydropyrane-2,5-diyl, the negative dielectric anisotropy is large. When combinations of a, b and c include a combination (a=1, b=1, c=0) or a combination (a=1, b=1, c=1), the clearing point is high.

1-3. Preferred Compound

Specific examples of preferred compound (1) include compounds (1-1) to (1-3) described in item 2.

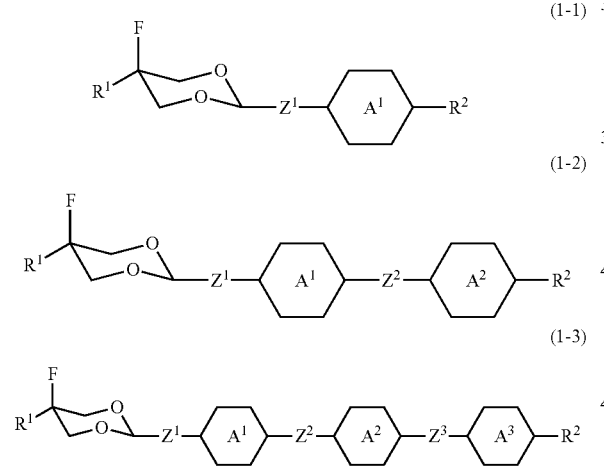

In formulas (1-1) to (1-3),

R$^1$ and R$^2$ are independently alkyl having 1 to 15 carbons, alkoxy having 1 to 14 carbons, alkenyl having 2 to 15 carbons and alkenyloxy having 2 to 14 carbons;

ring A$^1$, ring A$^2$ and ring A$^3$ are independently 1,4-cyclohexylene, 1,4-cyclohexenylene, 1,4-phenylene, 1,4-phenylene in which at least one of hydrogen is replaced by halogen, tetrahydropyran-2,5-diyl or dihydropyrane-2,5-diyl, but at least one is a ring represented by formula (A):

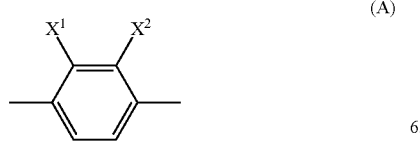

wherein, X$^1$ and X$^2$ are independently hydrogen or fluorine; and

Z$^1$, Z$^2$ and Z$^3$ are independently a single bond, —(CH$_2$)$_2$—, —CH=CH—, —COO—, —OCO—, —CH$_2$O—, —OCH$_2$—, —CF$_2$O— or —OCF$_2$—.

In compound (1), in the case where both X$^1$ and X$^2$ are fluorine when ring A$^1$ is represented by formula (A):

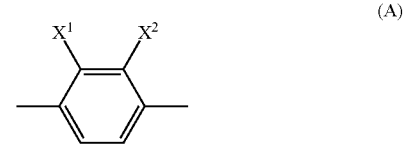

Z$^1$ is preferably —(CH$_2$)$_2$—, —CH=CH—, —CH$_2$O— or —OCH$_2$—.

Further preferred examples of compound (1) include compound (1-1-a), compound (1-1-b), compounds (1-2-a) to (1-2-k), compound (1-2-m), compounds (1-3-a) to (1-3-k) and compounds (1-3-m) to (1-3-t) described in item 5.

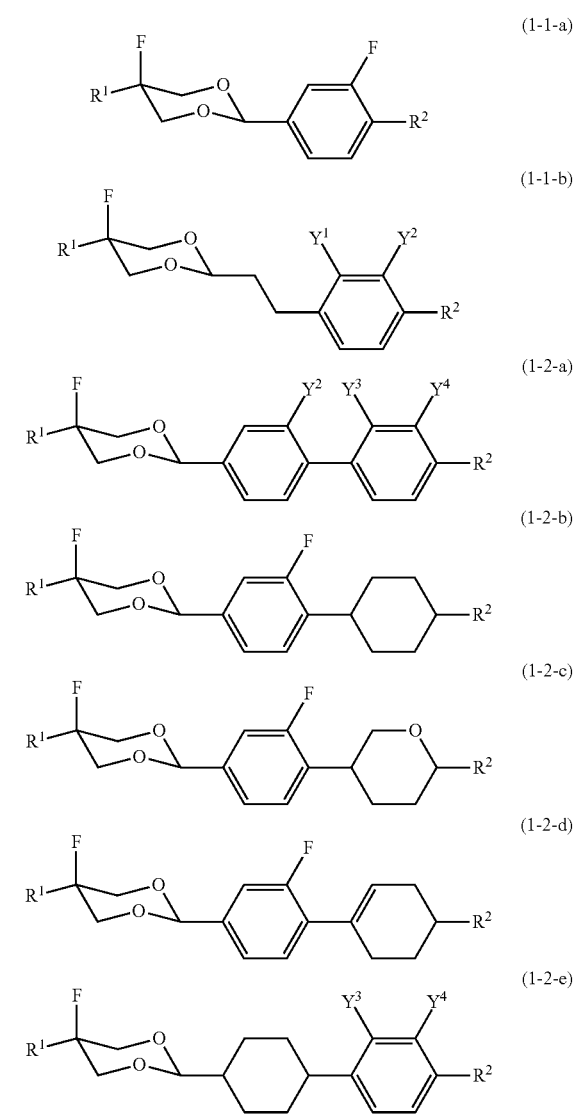

(1-2-f)
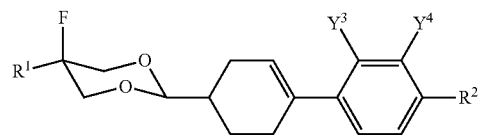
(1-2-g)
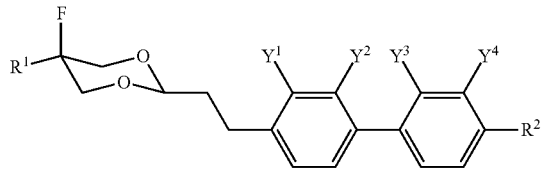
(1-2-h)
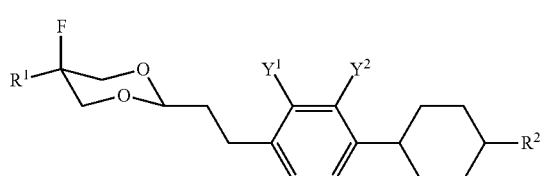
(1-2-i)
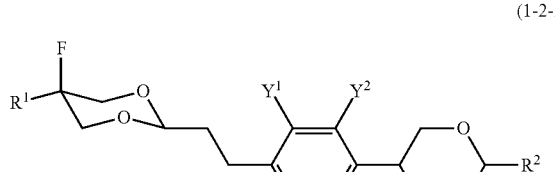
(1-2-j)
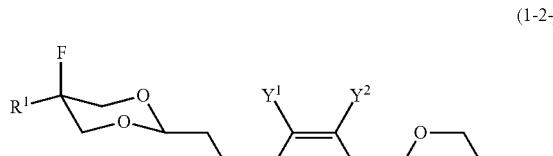
(1-2-k)
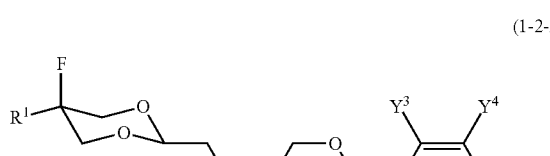
(1-2-m)
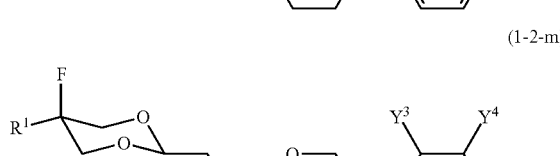
(1-3-a)
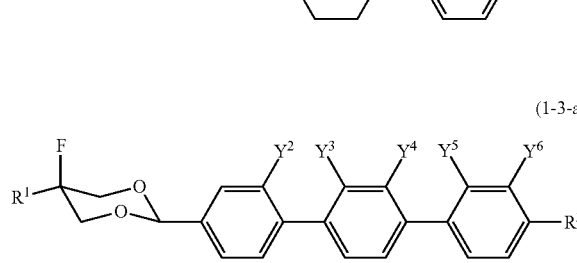
(1-3-b)
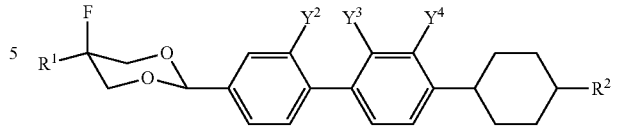
(1-3-c)
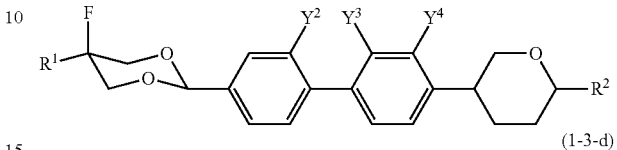
(1-3-d)
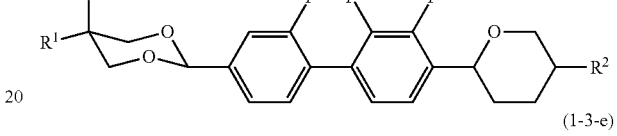
(1-3-e)
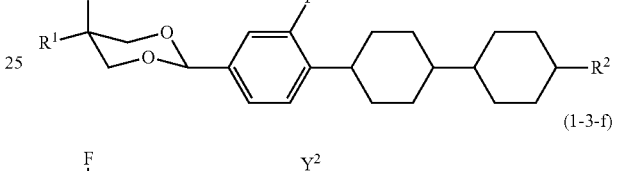
(1-3-f)
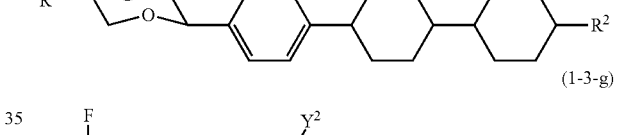
(1-3-g)
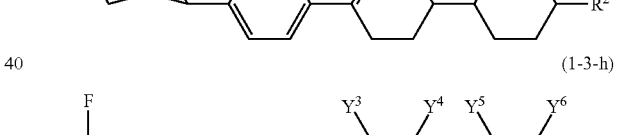
(1-3-h)
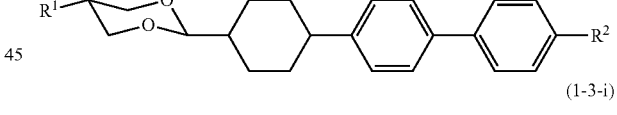
(1-3-i)
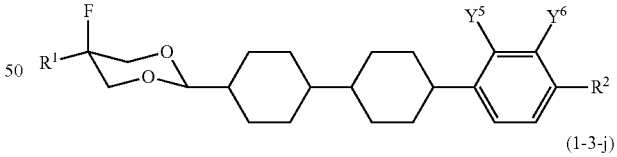
(1-3-j)
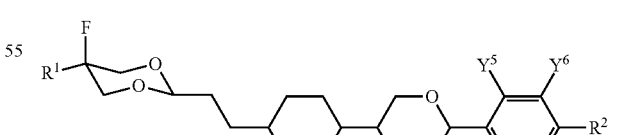
(1-3-k)
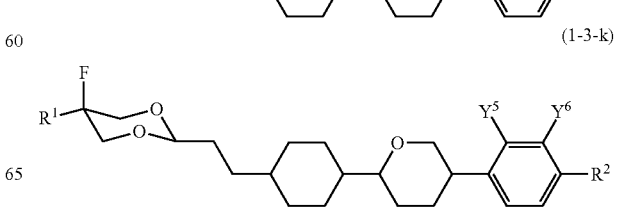

-continued

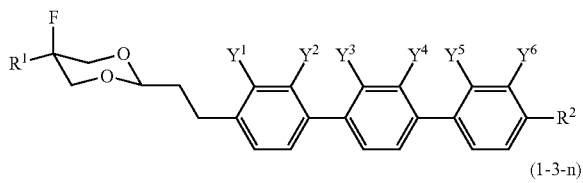
(1-3-m)

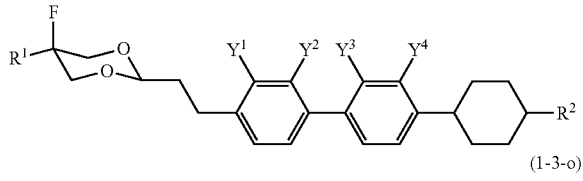
(1-3-n)

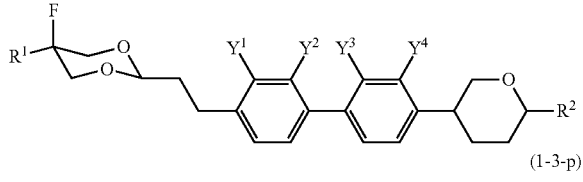
(1-3-o)

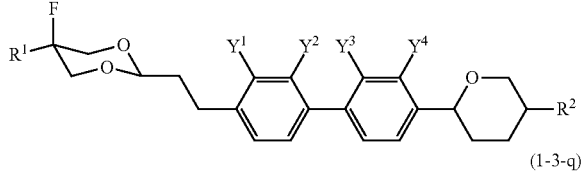
(1-3-p)

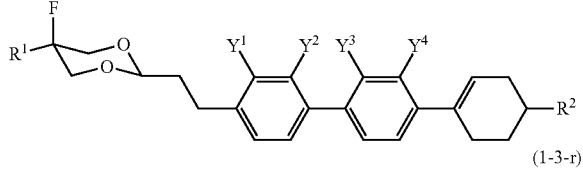
(1-3-q)

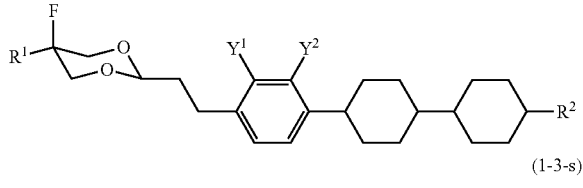
(1-3-r)

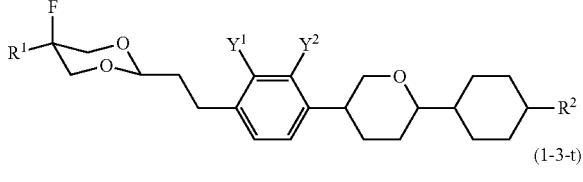
(1-3-s)

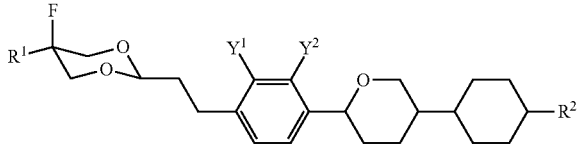
(1-3-t)

In compound (1-1-a), compound (1-1-b), compounds (1-2-a) to (1-2-k), compound (1-2-m), compounds (1-3-a) to (1-3-k) and compounds (1-3-m) to (1-3-t), $R^1$ and $R^2$ are independently alkyl having 1 to 10 carbons, alkoxy having 1 to 9 carbons, alkenyl having 2 to 10 carbons and alkenyloxy having 2 to 9 carbons; and $Y^1$ to $Y^6$ are independently hydrogen or fluorine.

1-4. Synthesis of Compound (1)

A method for preparing compound (1) will be described. Compound (1) can be prepared by suitably combining methods in synthetic organic chemistry. Methods for introducing an objective terminal group, ring and bonding group into a starting material are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.)

1-4-1. Formation of a Bonding Group

An example of a method for forming a bonding group in compound (1) is as described in the scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1G) correspond to compound (1) or an intermediate of compound (1)

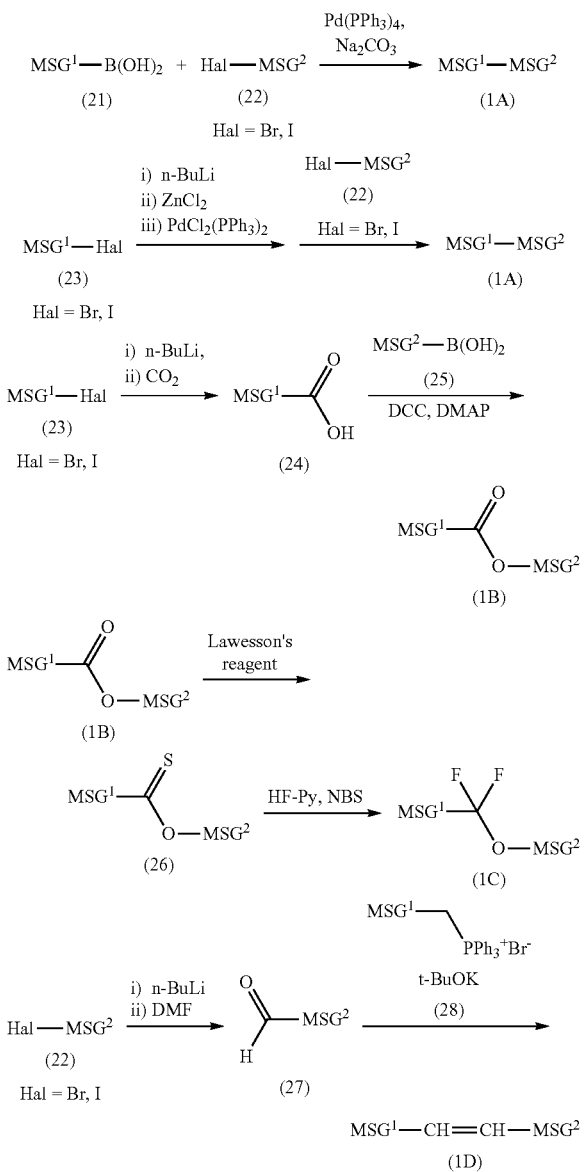

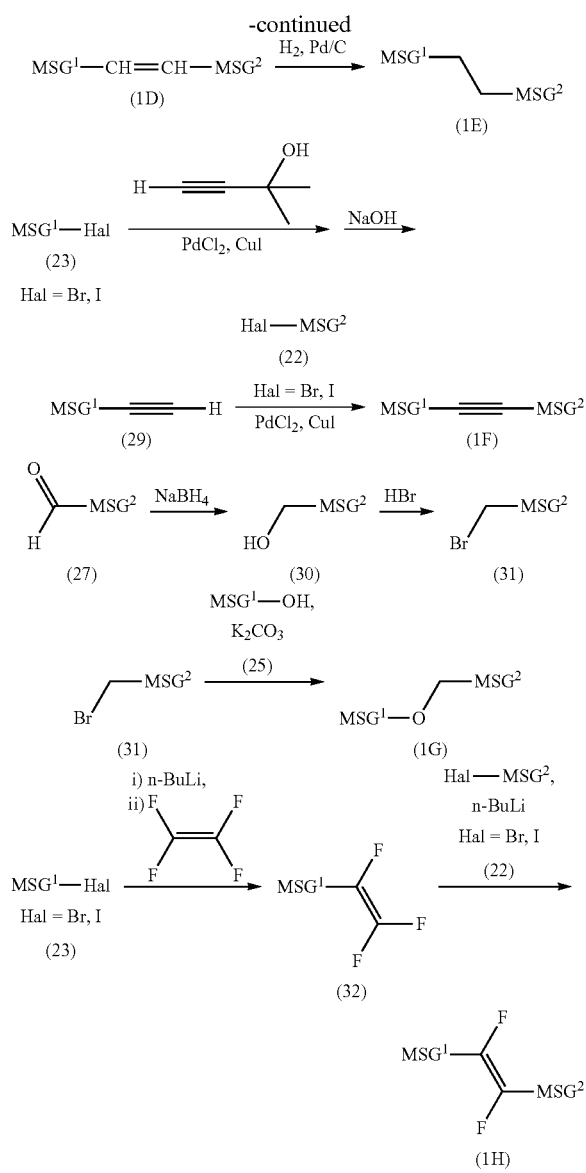

(I) Formation of a Single Bond

Compound (1A) is prepared by allowing aryl boronic acid (21) to react with compound (22) in the presence of carbonate and a catalyst such as tetrakis(triphenylphosphine)palladium. Compound (1A) is also prepared by allowing compound (23) to react with n-butyllithium and subsequently with zinc chloride, and further with compound (22) in the presence of a catalyst such as dichlorobis(triphenylphosphine)palladium.

(II) Formation of —COO— and —OCO—

Carboxylic acid (24) is obtained by allowing compound (23) to react with n-butyllithium and subsequently with carbon dioxide. Compound (1B) having —COO— is prepared by dehydrating carboxylic acid (24) and phenol (25) derived from compound (21) in the presence of 1,3-dicyclohexylcarbodiimide (DCC) and 4-dimethylaminopyridine (DMAP). A compound having —COO— is also prepared according to the method.

(III) Formation of —CF$_2$O— and —OCF$_2$—

Compound (26) is obtained by thionating compound (1B) with a Lawesson's reagent. Compound (10) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino) sulfur trifluoride (DAST). Refer to W. H. Bunnelle et al., J. Org. Chem. 1990, 55, 768. A compound having —OCF$_2$— is also prepared according to the method.

(IV) Formation of —CH=CH—

Aldehyde (27) is obtained by allowing compound (22) to react with n-butyllithium and subsequently with N,N-dimethylformamide (DMF). Compound (1D) is prepared by allowing phosphorus ylide generated by allowing phosphonium salt (28) to react with potassium tert-butoxide to react with aldehyde (27). A cis isomer is formed depending on reaction conditions, and therefore the cis isomer is isomerized into a trans isomer according to a publicly known method, when necessary.

(V) Formation of —CH$_2$CH$_2$—

Compound (1E) is prepared by hydrogenating compound (1D) in the presence of a catalyst such as palladium on carbon.

(VI) Formation of —C≡C—

Compound (29) is obtained by allowing compound (23) to react with 2-methyl-3-butyn-2-ol in the presence of a catalyst including dichloropalladium and copper iodide, and then deprotecting the resulting product under basic conditions. Compound (1F) is prepared by allowing compound (29) to react with compound (22) in the presence of a catalyst including dichlorobis(triphenylphosphine)palladium and copper halide.

(VII) Formation of —CH$_2$O— and —OCH$_2$—

Compound (30) is obtained by reducing compound (27) with sodium borohydride. Compound (31) is obtained by brominating the resulting product with hydrobromic acid. Compound (1G) is prepared by allowing compound (25) to react with compound (31) in the presence of potassium carbonate. A compound having —OCH$_2$— is also prepared according to the method.

(VIII) Formation of —CF=CF—

Compound (32) is obtained by treating compound (23) with n-butyllithium and then allowing the resulting treated material to react with tetrafluoroethylene. Compound (1H) is prepared by treating compound (22) with n-butyllithium and then allowing the resulting treated material to react with compound (32).

1-4-2. Formation of Ring A$^1$, Ring A$^2$ and Ring A$^3$

With regard to a ring such as 1,4-cyclohexylene, 1,4-cyclohexenylene, 1,4-phenylene, 2-fluoro-1,4-phenylene, 2,3-difluoro-1,4-phenylene, and tetrahydropyran-2,5-diyl, a starting materials is commercially available or a synthetic methods is well known.

1-4-3. Synthesis Examples

An example of a method for preparing compound (1) is as described below. In the compounds, R$^1$, R$^2$, ring A$^1$, ring A$^2$, ring A$^3$, Z$^1$, Z$^2$, Z$^3$, a, b and c are defined in a manner identical with the definitions in item 1.

An example of a method for preparing compound (1) is as described below. Compound (52) is obtained by allowing sodium hydride and Selectfluor to act on compound (51) that is commercially available or whose synthetic method is well known. Compound (53) is obtained by allowing sodium borohydride to act on compound (52). Compound (54) is obtained by allowing triethylamine and chlorotrimethylsilane to act on compound (53). Moreover, compound (1) can be obtained by allowing trimethylsilyl trifluoromethanesulfonate and compound (54) to act on compound (55) prepared according to a publicly known method.

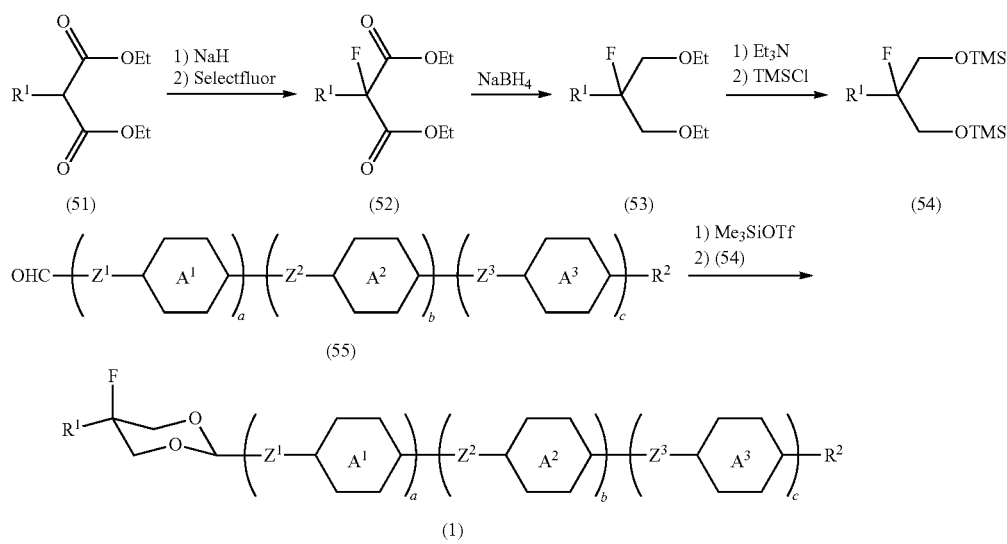

2. Composition (1)

Liquid crystal composition (1) of the invention will be described. Composition (1) contains at least one compound (1) as component A. Composition (1) may contain two or more compounds (1). A component in the liquid crystal compound may be compound (1) only. In order to develop excellent physical properties, composition (1) preferably contains at least one compound (1) in the range of approximately 1 to approximately 99% by weight. In a composition having a positive dielectric anisotropy, a preferred content of compound (1) is in the range of approximately 5 to approximately 60% by weight. In a composition having a negative dielectric anisotropy, a preferred content of compound (1) is approximately 30% by weight or less. Composition (1) may also contain compound (1) and various liquid crystal compounds that are not described herein.

A preferred composition contains a compound selected from components B, C, D and E shown below. When composition (1) is prepared, components can also be selected, for example, by taking dielectric anisotropy of compound (1) into consideration. A composition prepared by suitably selecting the components has the high maximum temperature of the nematic phase, the low minimum temperature of the nematic phase, the small viscosity, the suitable optical anisotropy, the large dielectric anisotropy and the suitable elastic constant.

Component B includes compounds (2) to (4). Component C includes compound (5). Component D includes compounds (6) to (12). Component E includes compounds (13) to (15). The components will be described in the order.

Component B is a compound having a halogen-containing group or a fluorine-containing group at a right terminal. Specific preferred examples of component B include compounds (2-1) to (2-16), compounds (3-1) to (3-113) and compounds (4-1) to (4-57).

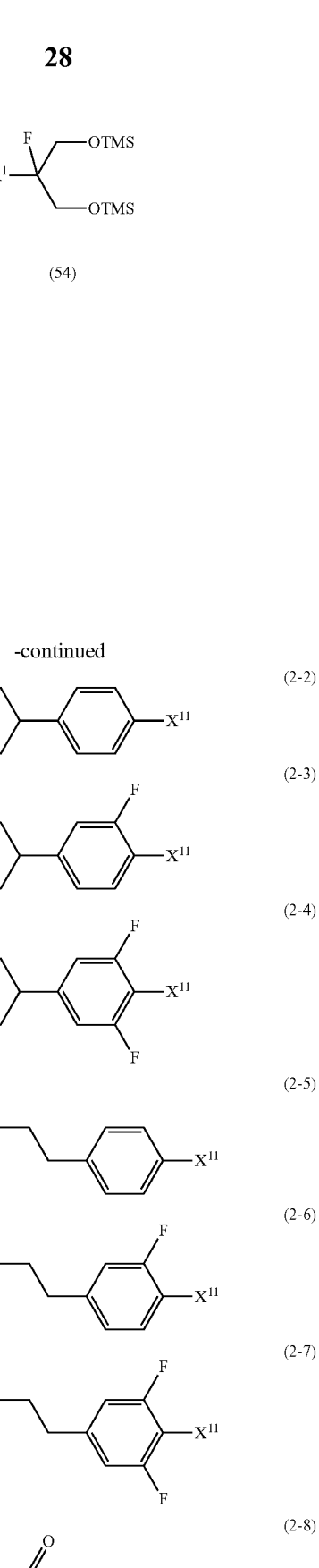

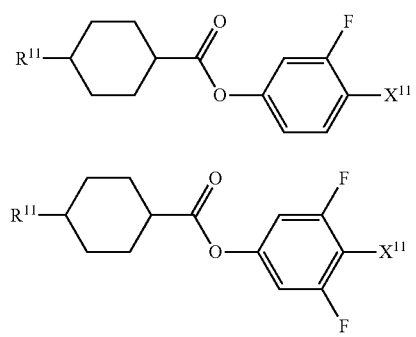
(2-9)
(2-10)
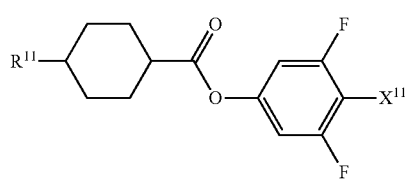
(2-11)
(2-12)
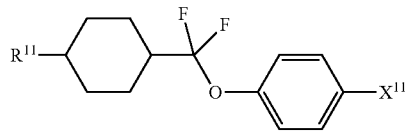
(2-13)
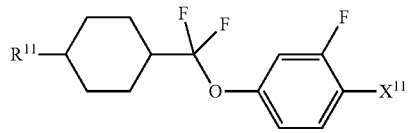
(2-14)
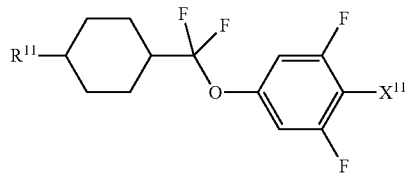
(2-15)
(2-16)
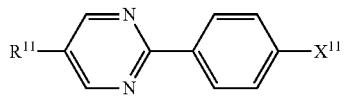
(3-1)
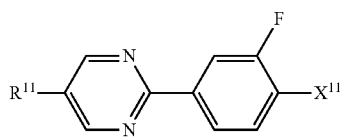
(3-2)
(3-3)
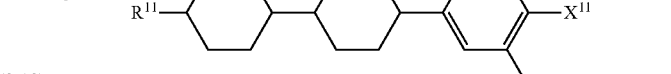
(3-4)
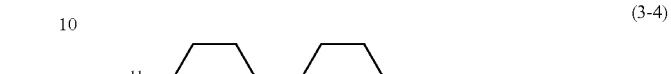
(3-5)
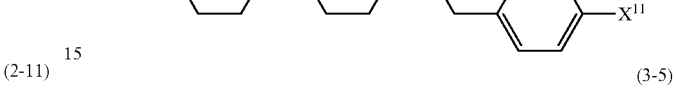
(3-6)
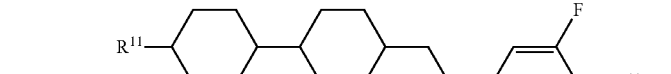
(3-7)
(3-8)
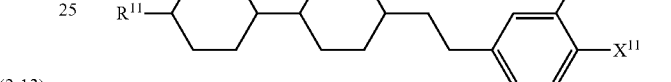
(3-9)
(3-10)
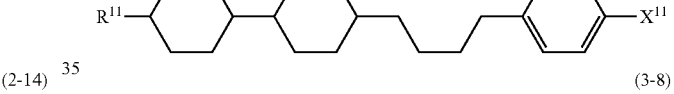
(3-11)

(3-12) 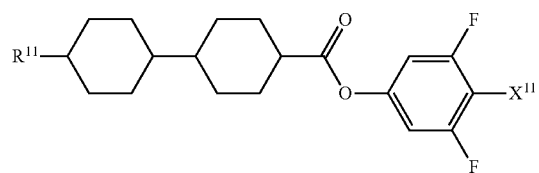
(3-13) 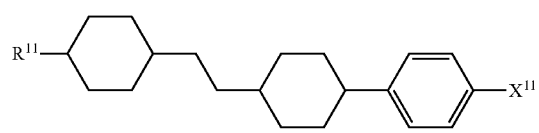
(3-14) 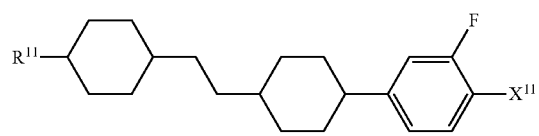
(3-15) 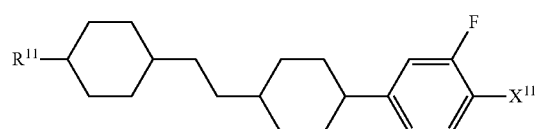
(3-16) 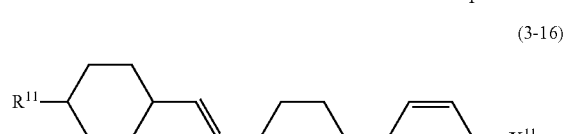
(3-17) 
(3-18) 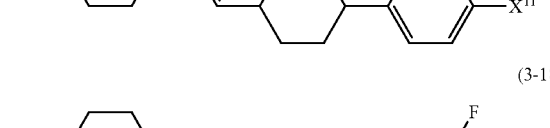
(3-19) 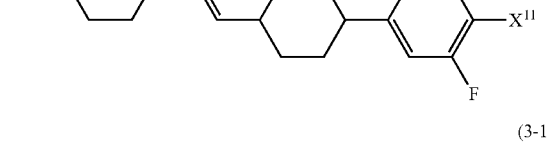
(3-20) 
(3-21) 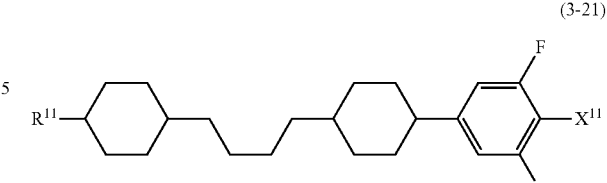
(3-22) 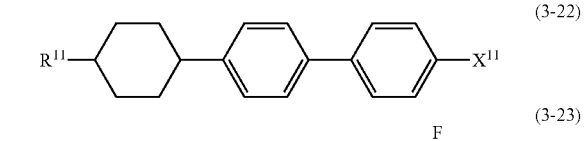
(3-23) 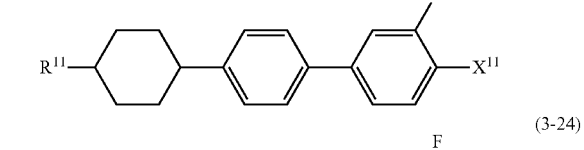
(3-24) 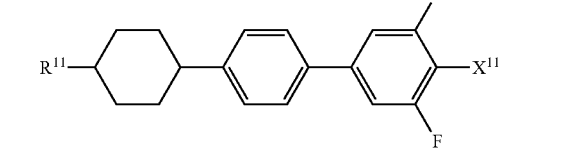
(3-25) 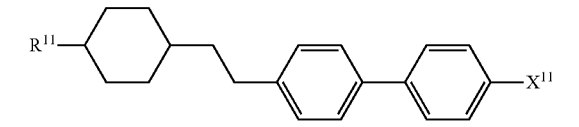
(3-26) 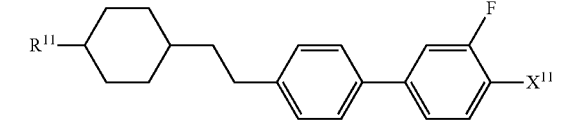
(3-27) 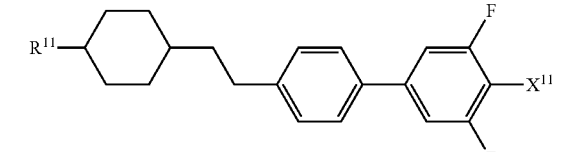
(3-28) 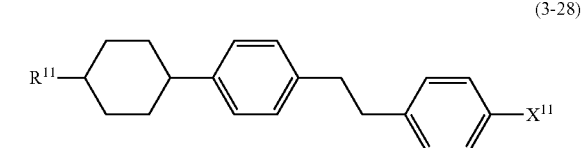
(3-29) 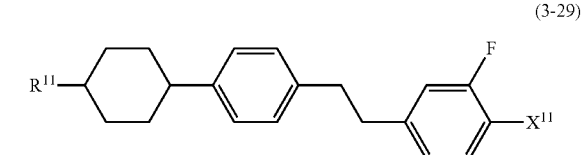
(3-30) 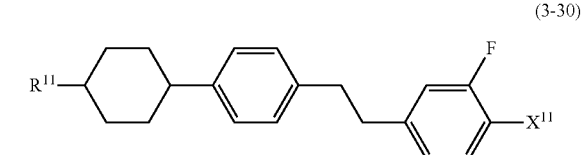

(3-31)
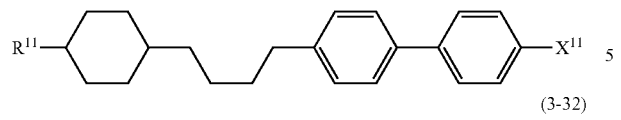
(3-32)
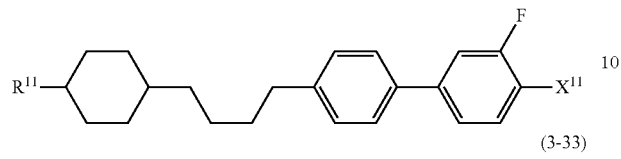
(3-33)
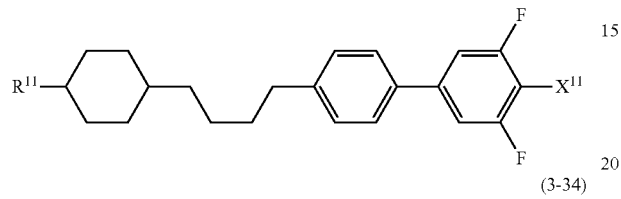
(3-34)
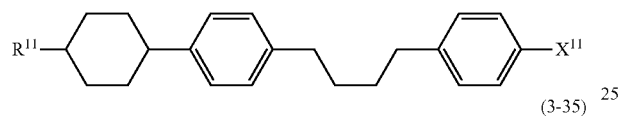
(3-35)
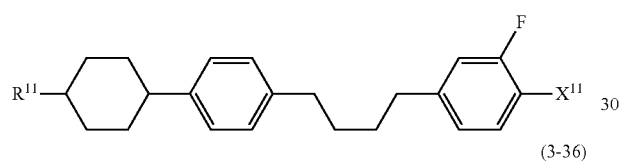
(3-36)
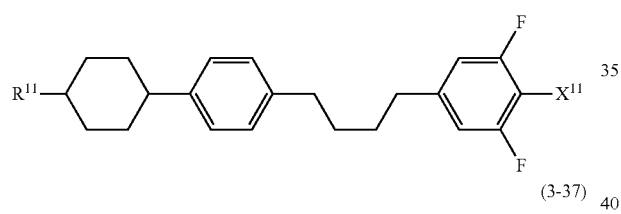
(3-37)
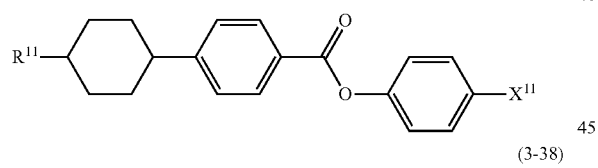
(3-38)
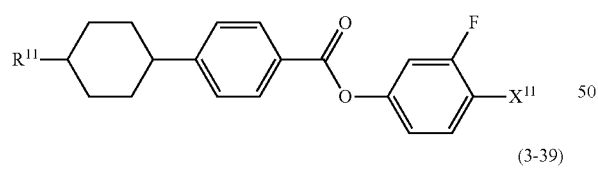
(3-39)
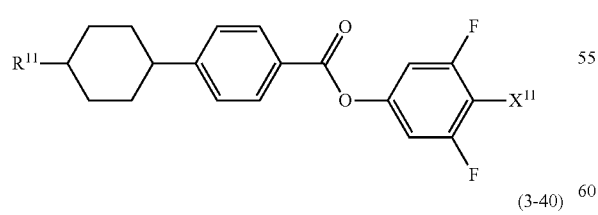
(3-40)
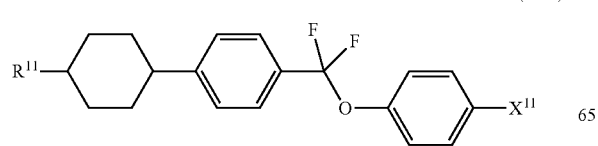
(3-41)
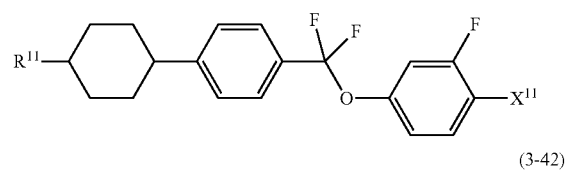
(3-42)
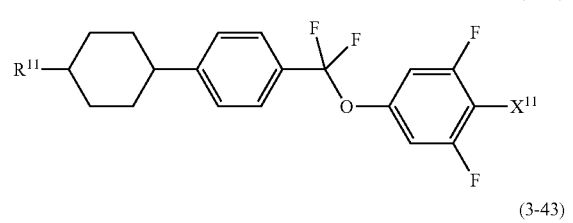
(3-43)
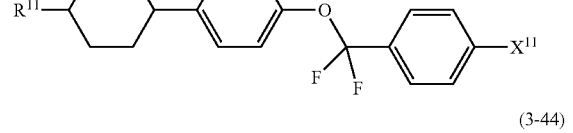
(3-44)
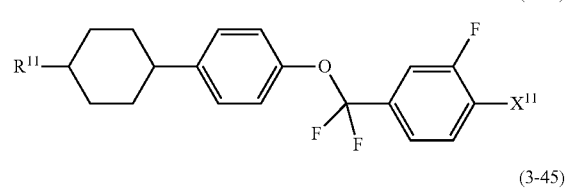
(3-45)
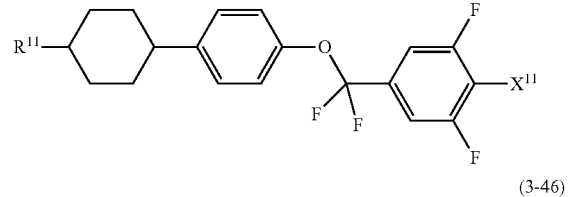
(3-46)
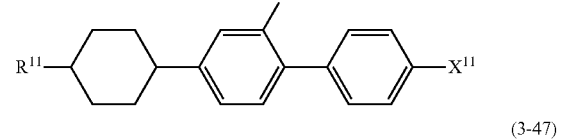
(3-47)
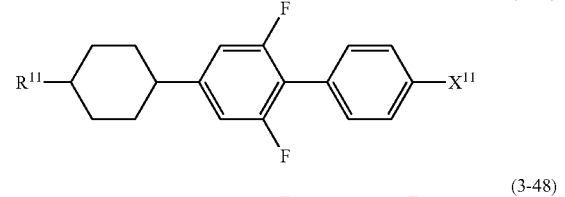
(3-48)
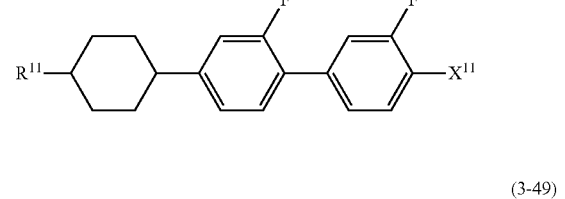
(3-49)

(3-50)
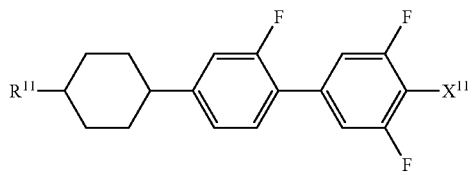
(3-51)
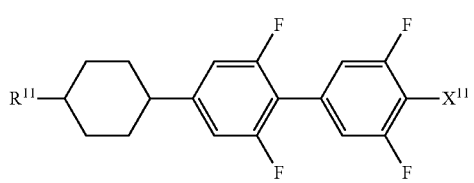
(3-52)
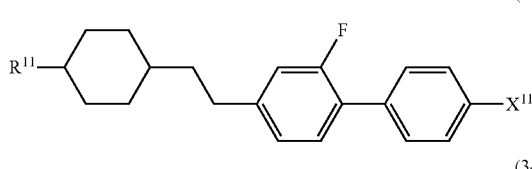
(3-53)
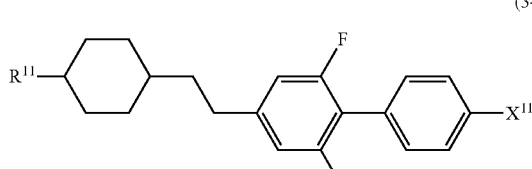
(3-54)
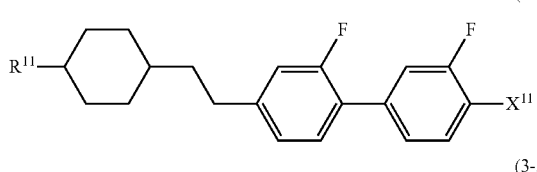
(3-55)
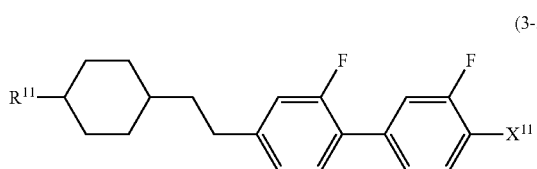
(3-56)
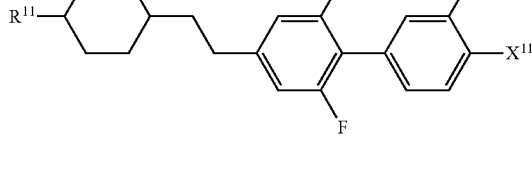
(3-57)
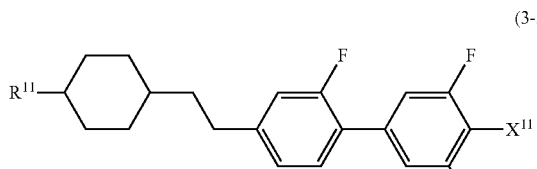
(3-58)
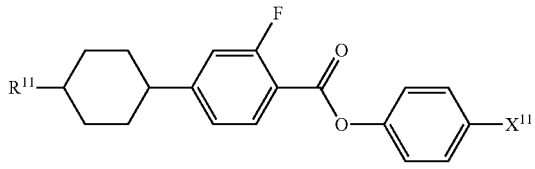
(3-59)
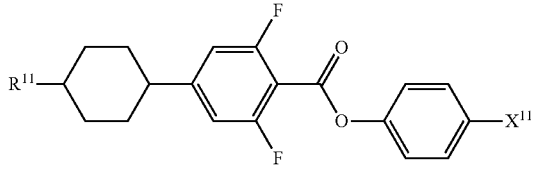
(3-60)
(3-61)
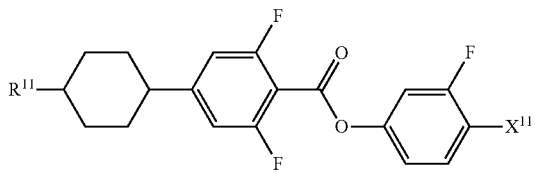
(3-62)
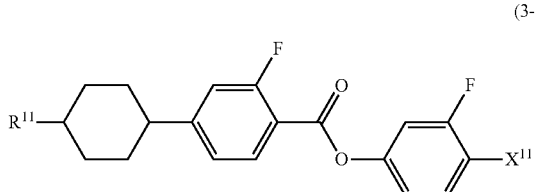
(3-63)
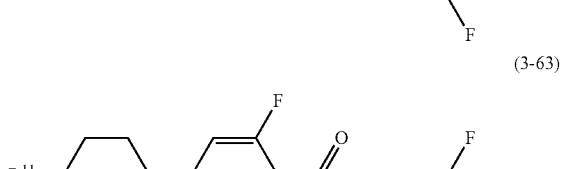
(3-64)
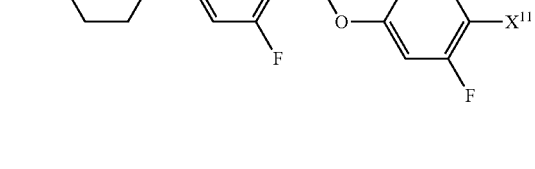
(3-65)
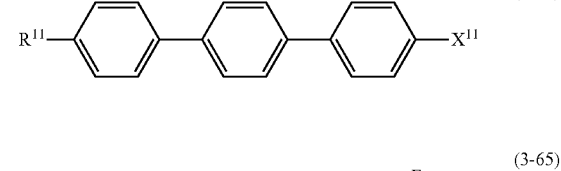

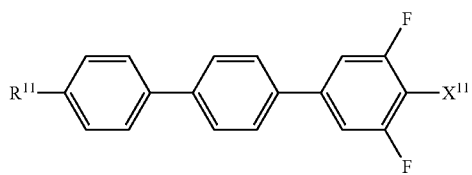
(3-66)
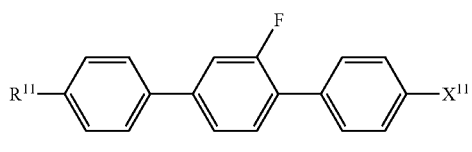
(3-67)
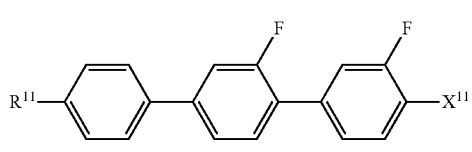
(3-68)
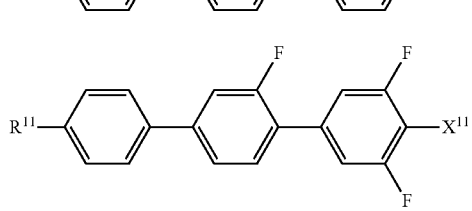
(3-69)
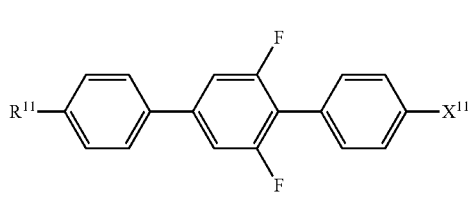
(3-70)
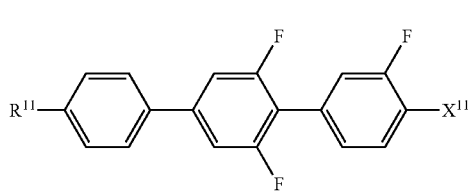
(3-71)
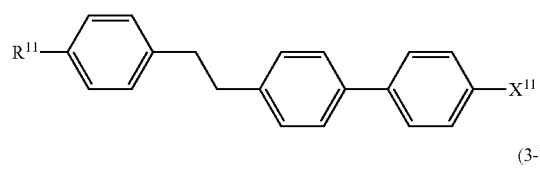
(3-72)
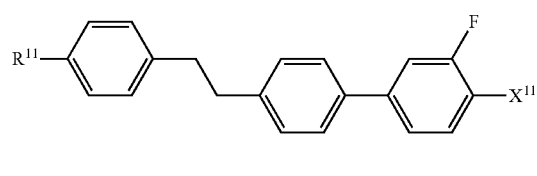
(3-73)
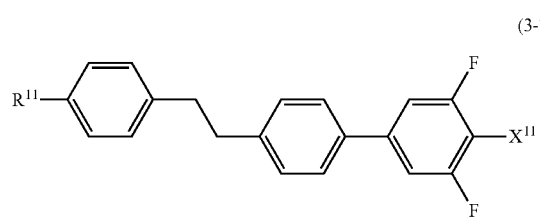
(3-74)
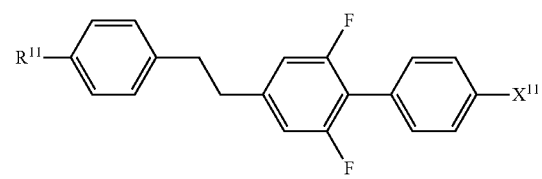
(3-75)
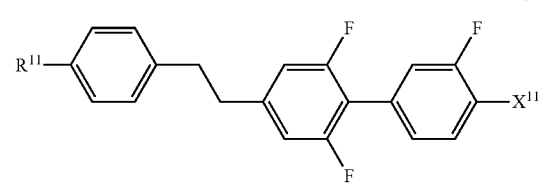
(3-76)
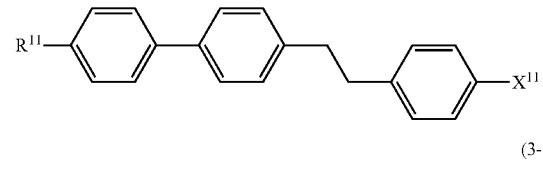
(3-77)
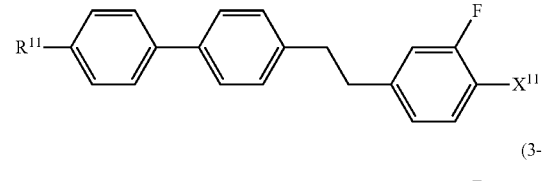
(3-78)
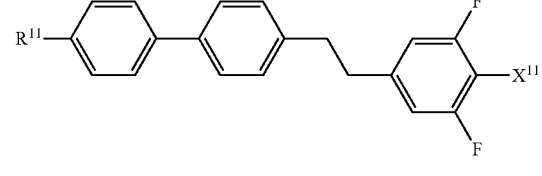
(3-79)
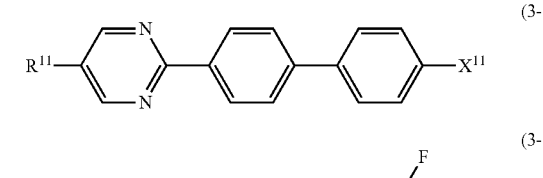
(3-80)
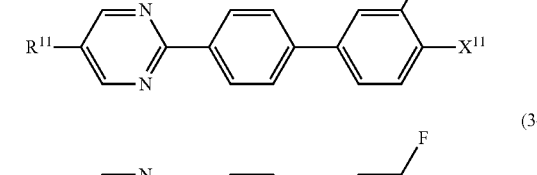
(3-81)
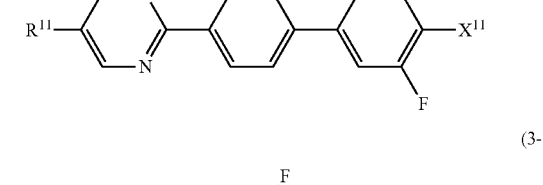
(3-82)
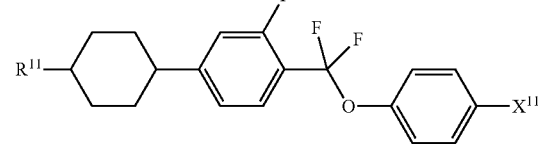
(3-83)

(3-84) 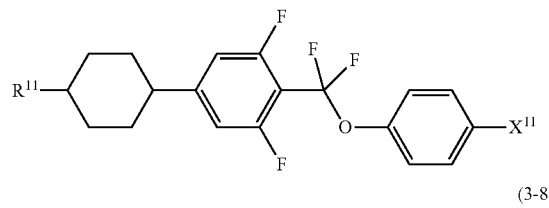
(3-85) 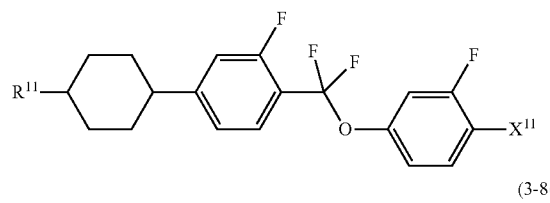
(3-86) 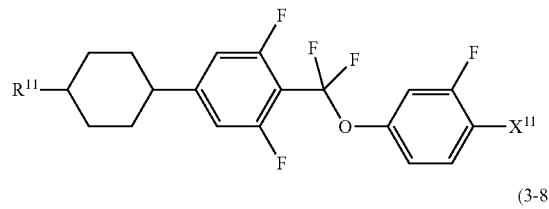
(3-87) 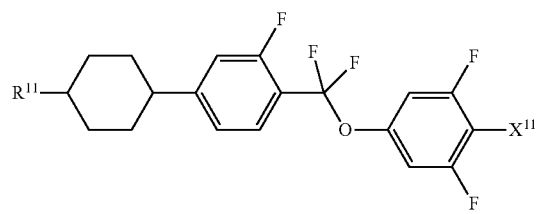
(3-88) 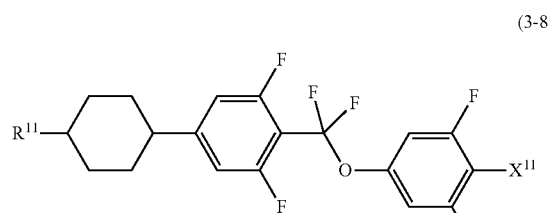
(3-89) 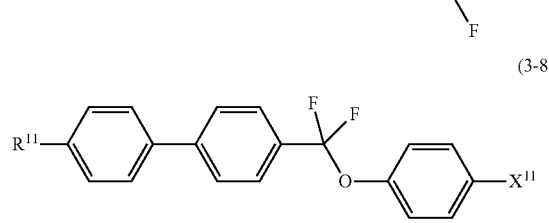
(3-90) 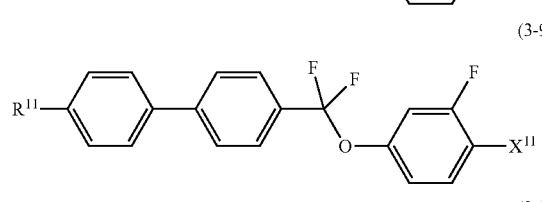
(3-91) 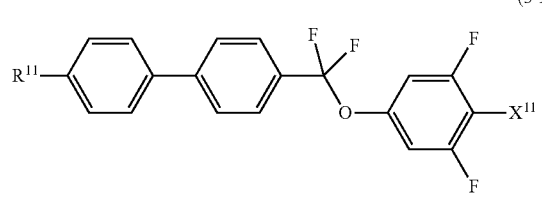
(3-92) 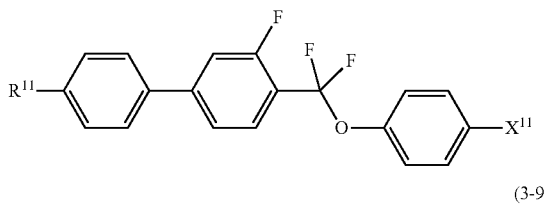
(3-93) 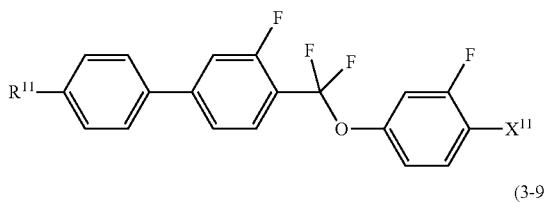
(3-94) 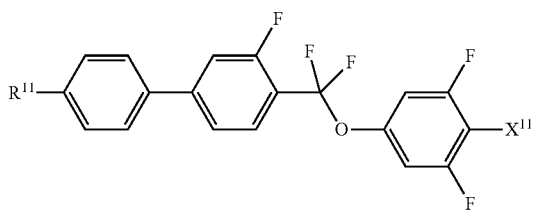
(3-95) 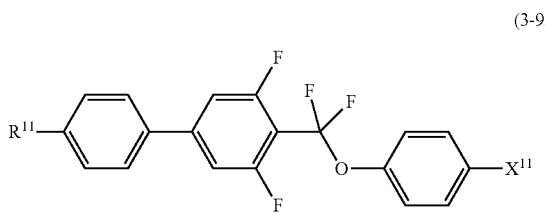
(3-96) 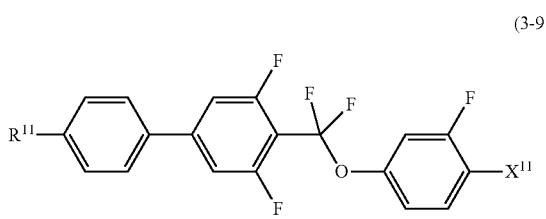
(3-97) 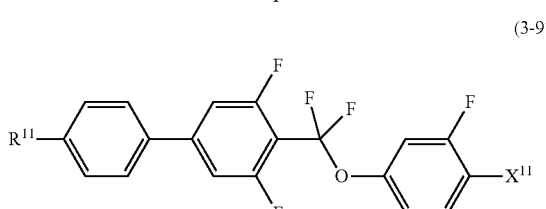
(3-98) 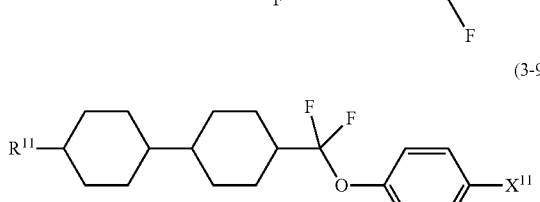
(3-99) 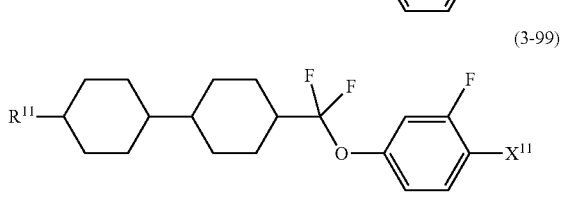

(3-100) 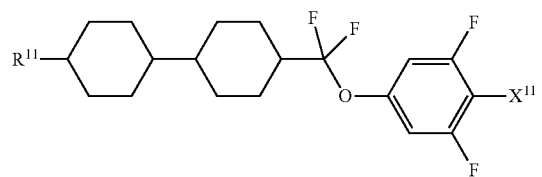
(3-101) 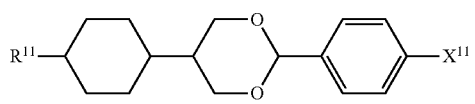
(3-102) 
(3-103) 
(3-104) 
(3-105) 
(3-106) 
(3-107) 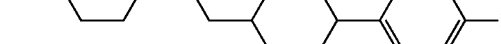
(3-108) 
(3-109) 
(3-110) 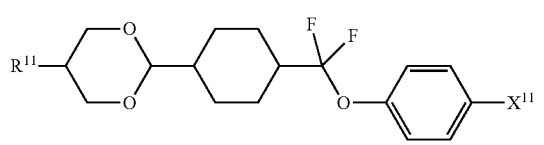
(3-111) 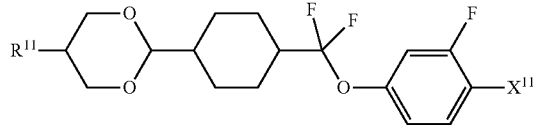
(3-112) 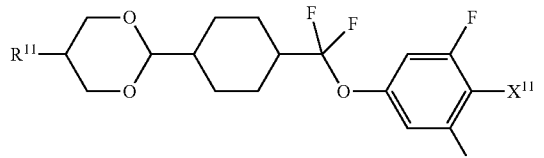
(3-113) 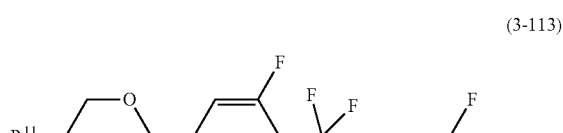
(4-1) 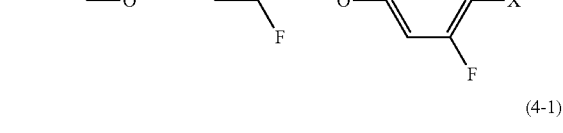
(4-2) 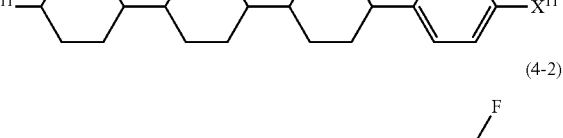
(4-3) 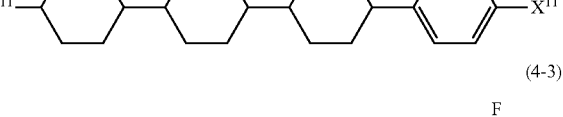
(4-4) 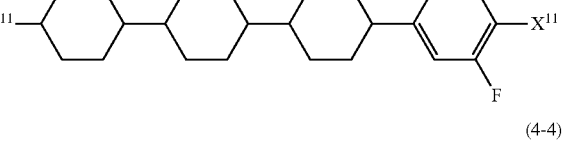
(4-5) 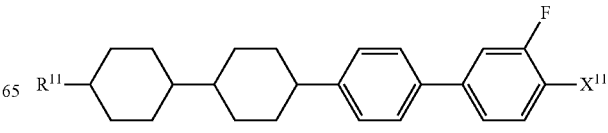

(4-6) 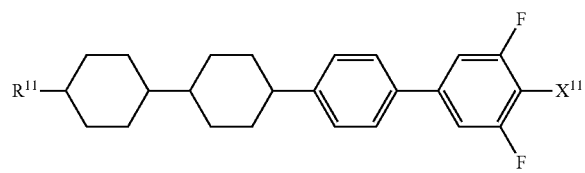
(4-7) 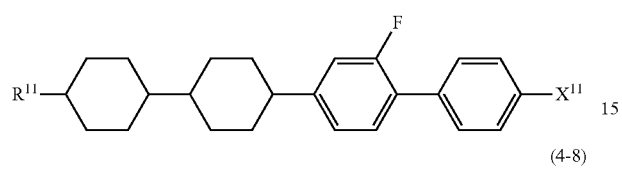
(4-8) 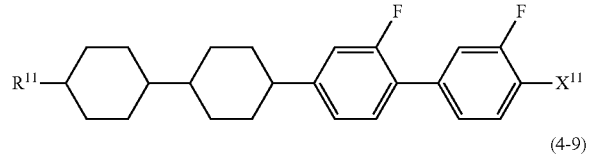
(4-9) 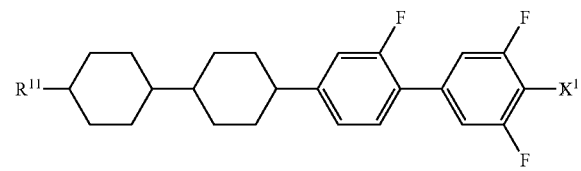
(4-10) 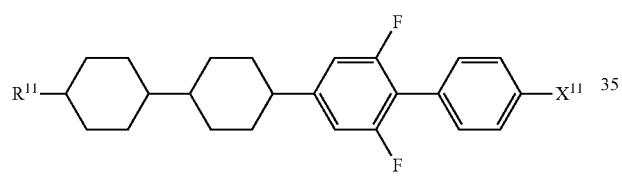
(4-11) 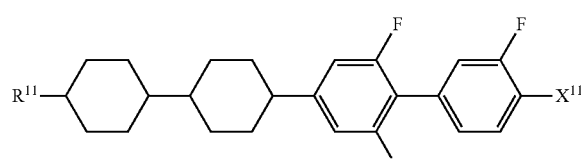
(4-12) 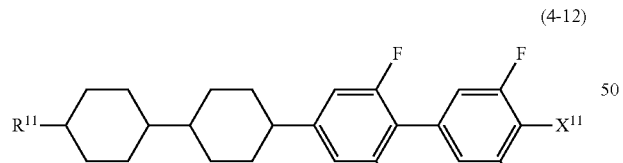
(4-13) 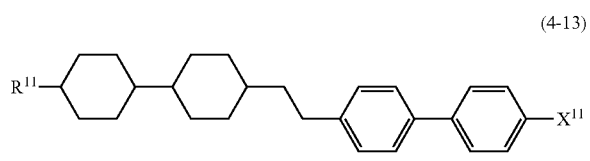
(4-14) 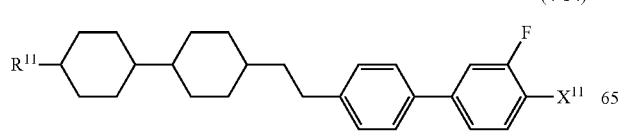
(4-15) 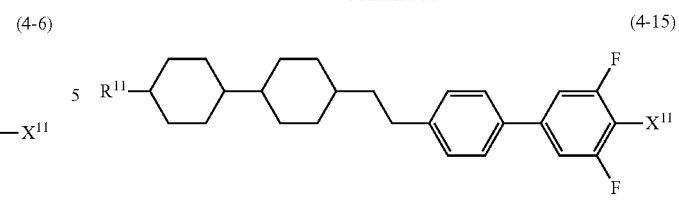
(4-16) 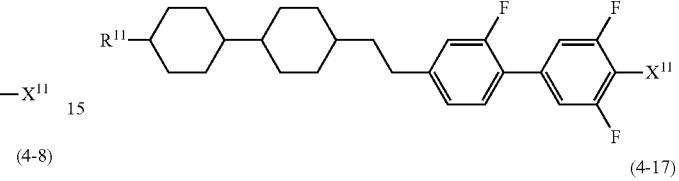
(4-17) 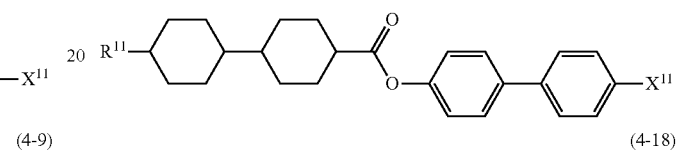
(4-18) 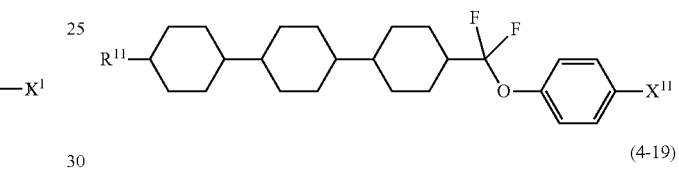
(4-19) 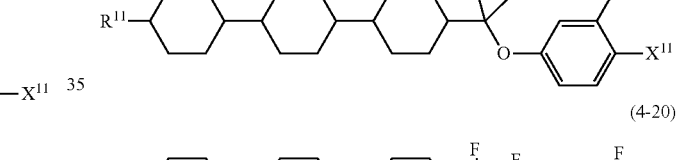
(4-20) 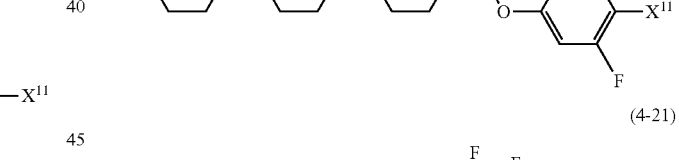
(4-21) 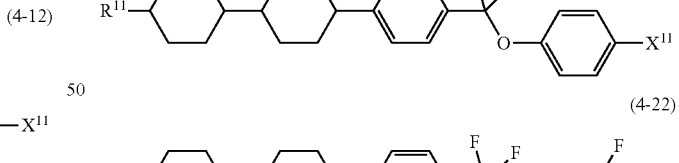
(4-22) 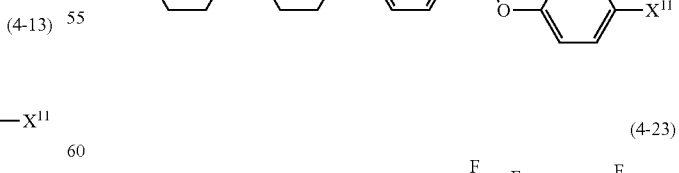
(4-23)

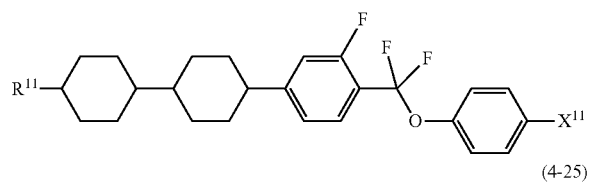 (4-24)
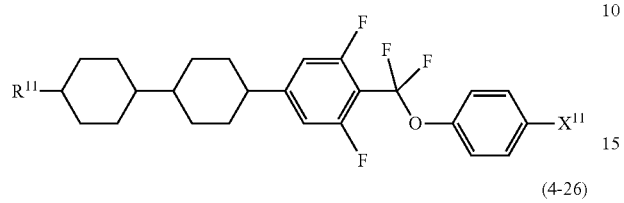 (4-25)
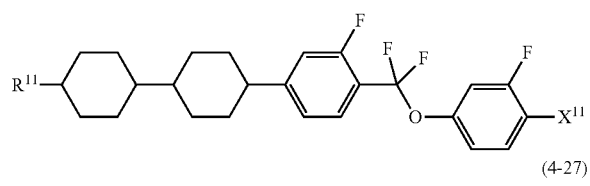 (4-26)
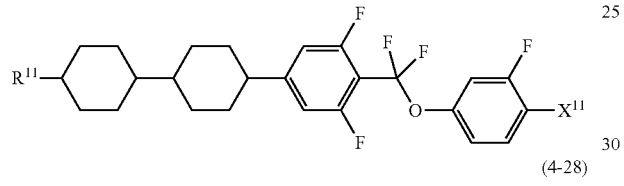 (4-27)
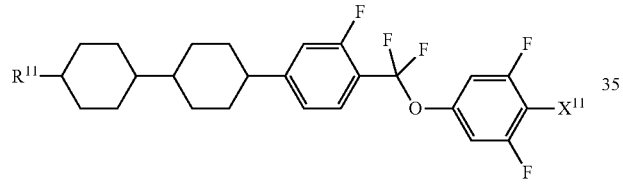 (4-28)
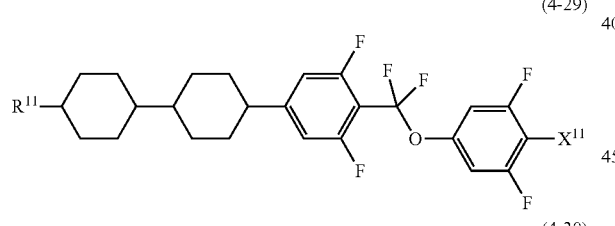 (4-29)
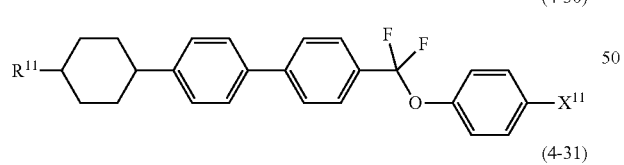 (4-30)
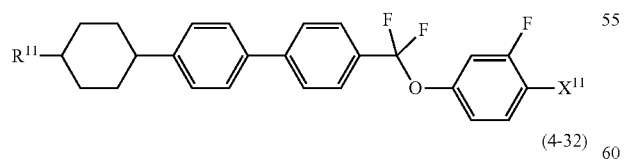 (4-31)
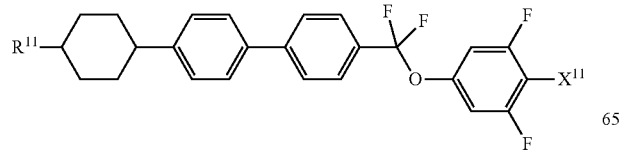 (4-32)
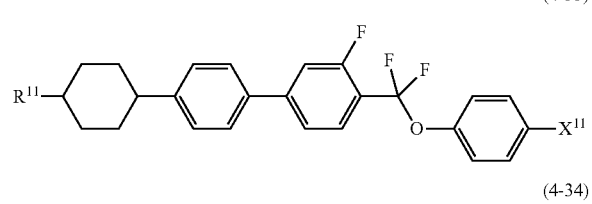 (4-33)
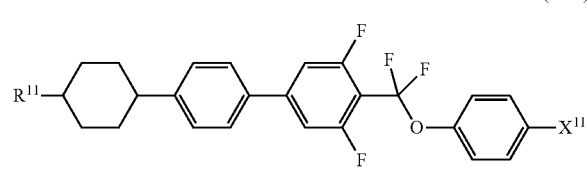 (4-34)
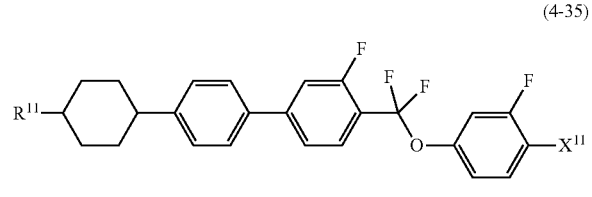 (4-35)
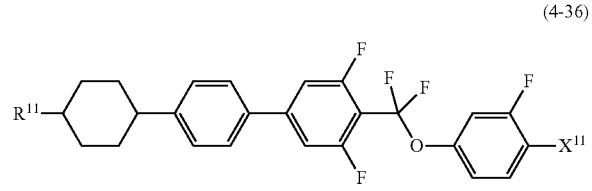 (4-36)
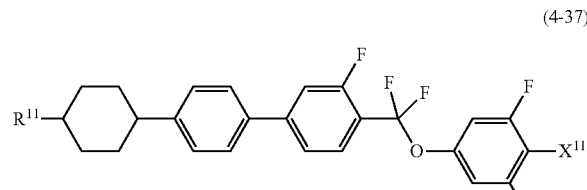 (4-37)
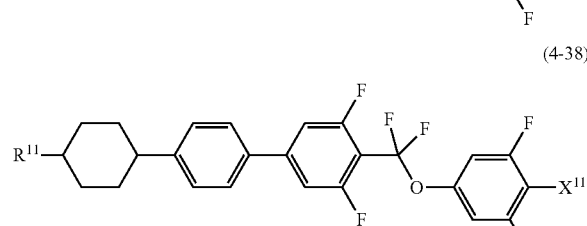 (4-38)
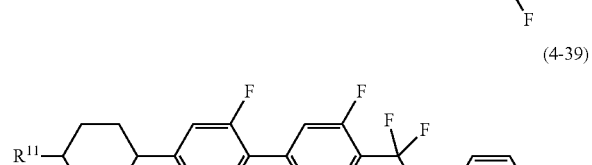 (4-39)
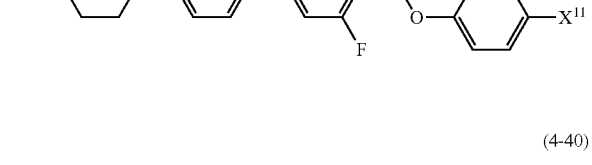 (4-40)
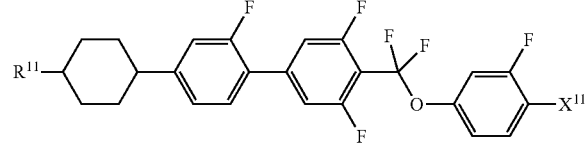

(4-41)
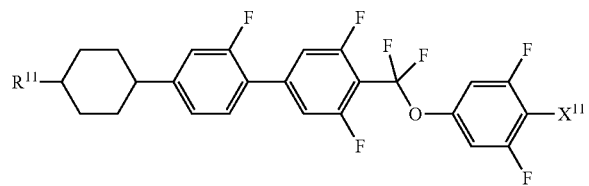
(4-42)
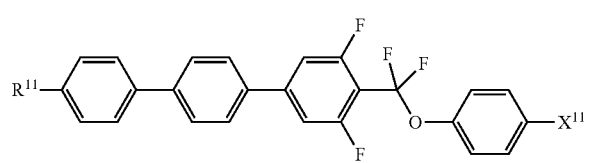
(4-43)
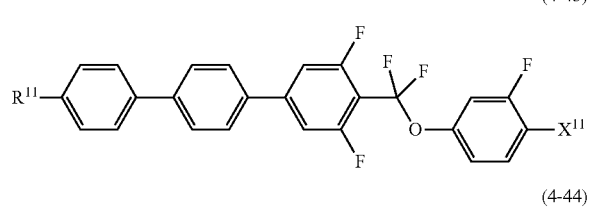
(4-44)
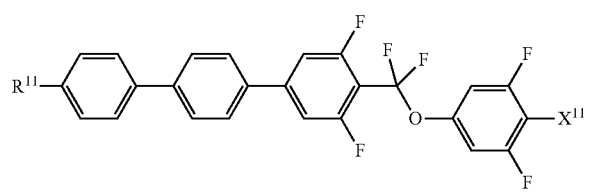
(4-45)
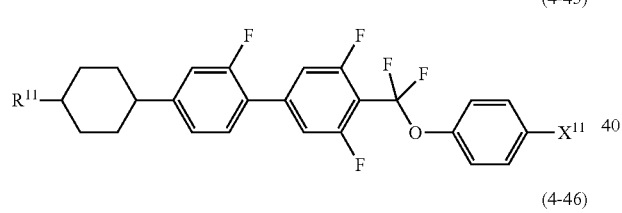
(4-46)
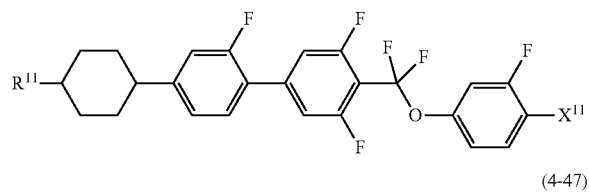
(4-47)
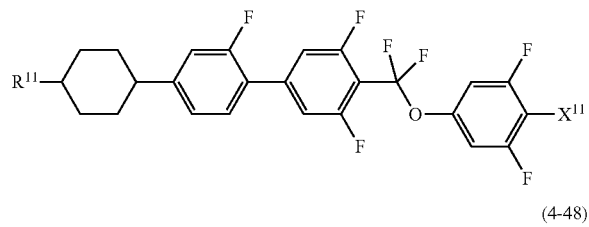
(4-48)
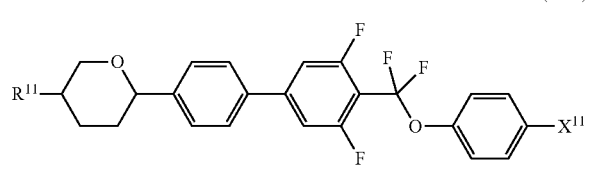
(4-49)
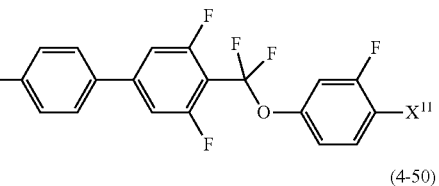
(4-50)
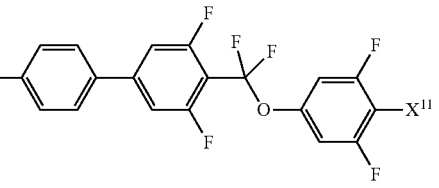
(4-51)
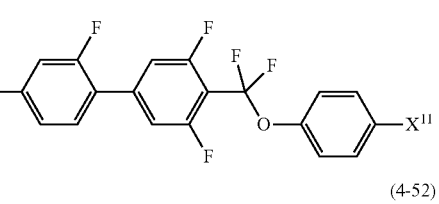
(4-52)
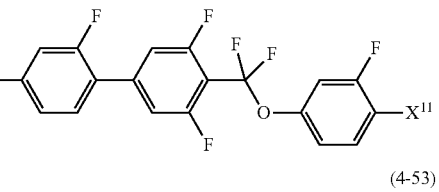
(4-53)
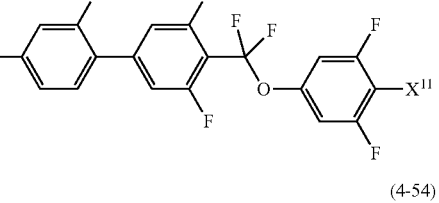
(4-54)
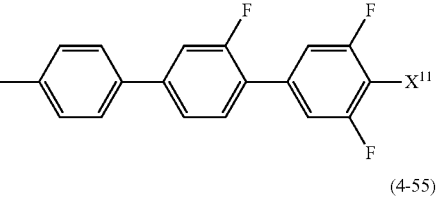
(4-55)
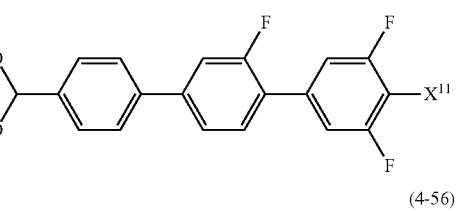
(4-56)
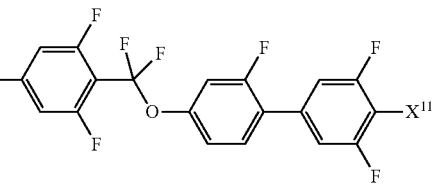

(4-57)

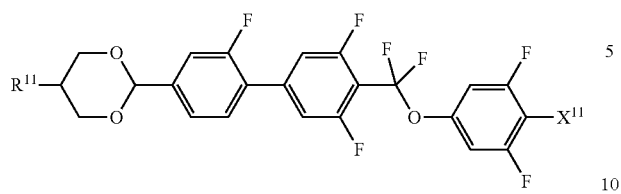

In the compounds (component B), $R^{11}$ and $X^{11}$ are defined in a manner identical with the definitions in formulas (2) to (4) described in item 11.

Component B has the positive dielectric anisotropy, and superb stability to heat, light and so forth, and therefore is used for preparing a composition for a TFT mode or a PSA mode. A content of component B is suitably in the range of approximately 1 to approximately 99% by weight, preferably in the range of approximately 10 to approximately 97% by weight, and further preferably in the range of approximately 40 to approximately 95% by weight, based on the total weight of the composition. The viscosity of the composition can be adjusted by further adding compounds (12) to (14) (component E).

Component C is compound (5) in which a right terminal group is —C≡N or —C≡C—C≡N. Preferred examples of component C include compounds (5-1) to (5-64).

(5-1)
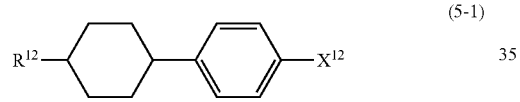

(5-2)
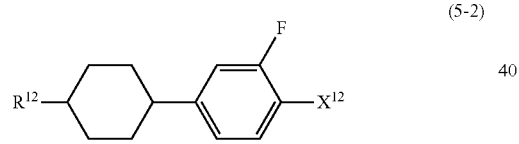

(5-3)
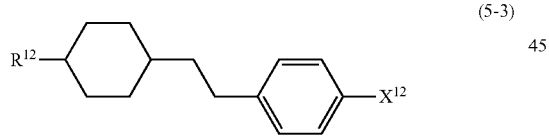

(5-4)
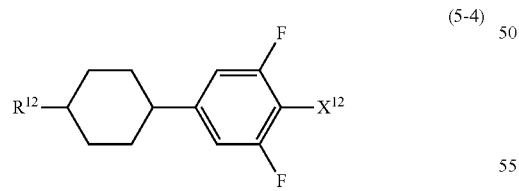

(5-5)
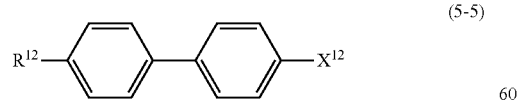

(5-6)
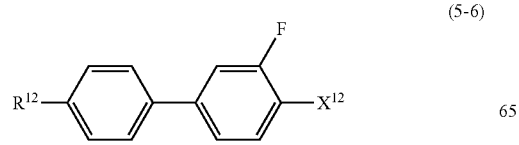

(5-7)
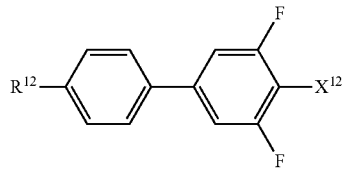

(5-8)
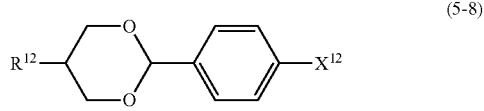

(5-9)
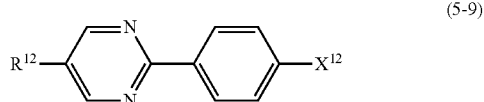

(5-10)
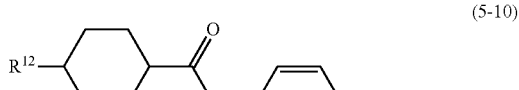

(5-11)
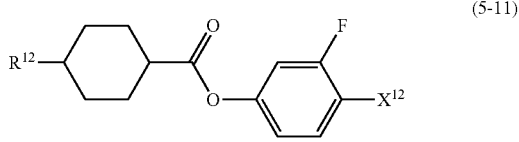

(5-12)
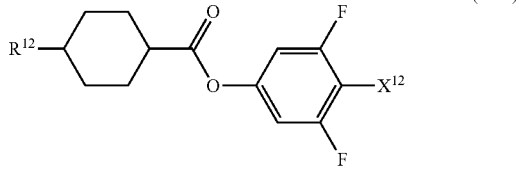

(5-13)
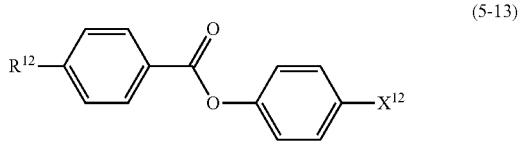

(5-14)
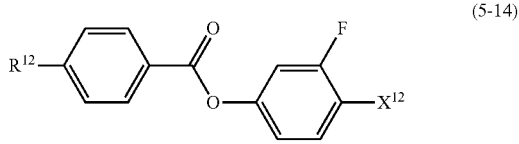

(5-15)
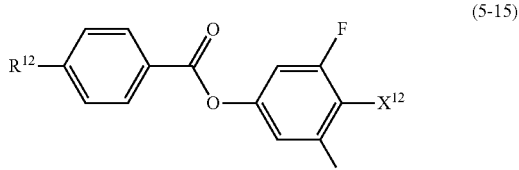

(5-16)
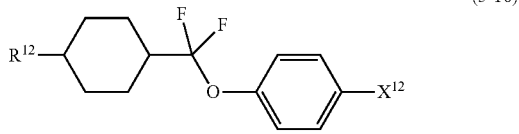

(5-17)
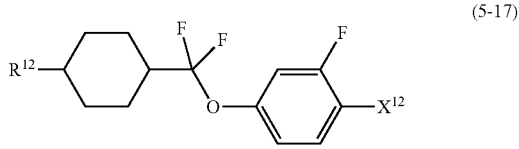

(5-18) 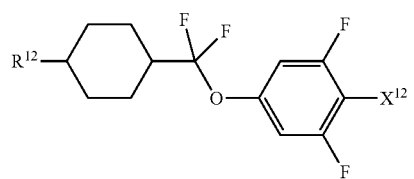
(5-19) 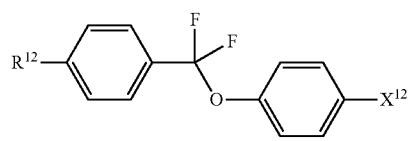
(5-20) 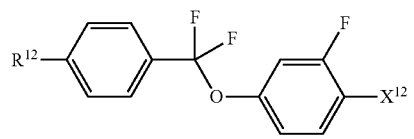
(5-21) 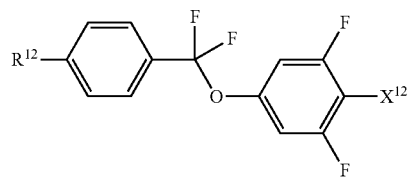
(5-22) 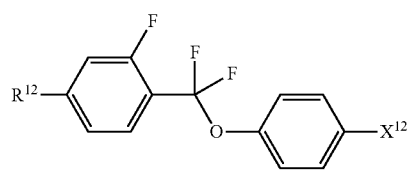
(5-23) 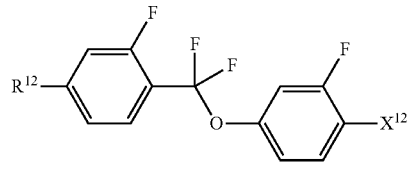
(5-24) 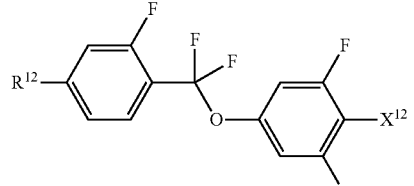
(5-25) 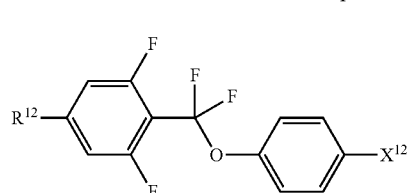
(5-26) 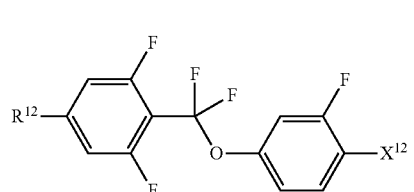
(5-27) 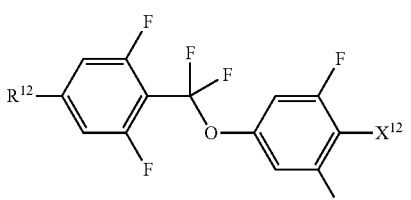
(5-28) 
(5-29) 
(5-30) 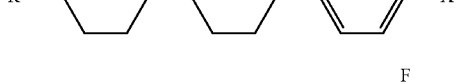
(5-31) 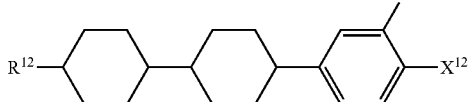
(5-32) 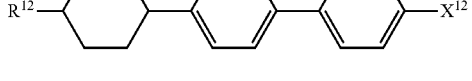
(5-33) 
(5-34) 
(5-35) 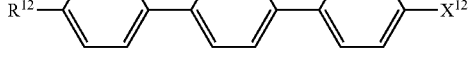
(5-36) 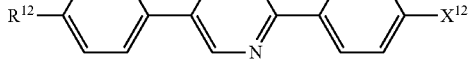
(5-37) 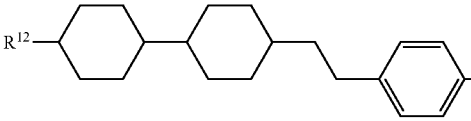

(5-38) 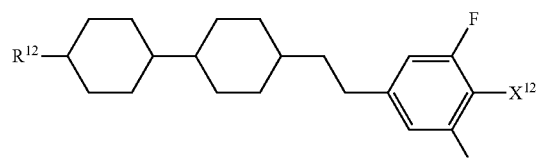
(5-39) 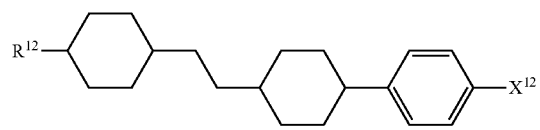
(5-40) 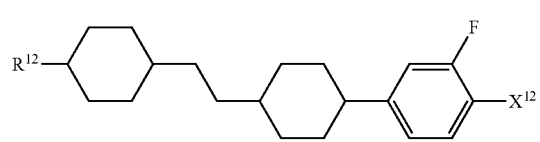
(5-41) 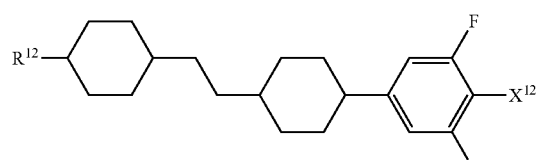
(5-42) 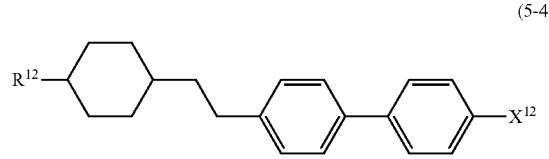
(5-43) 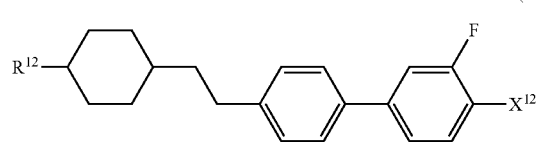
(5-44) 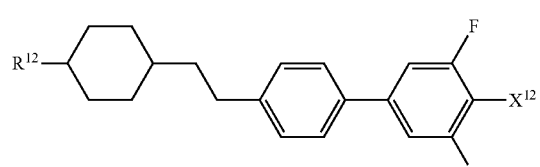
(5-45) 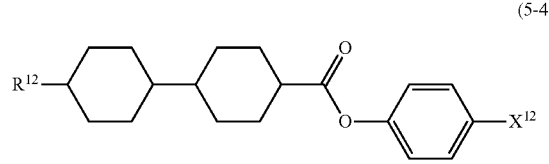
(5-46) 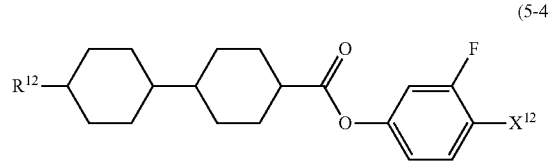
(5-47) 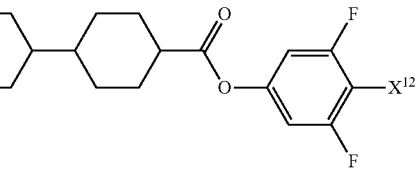
(5-48) 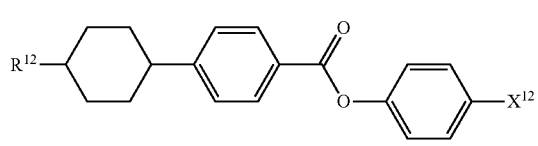
(5-49) 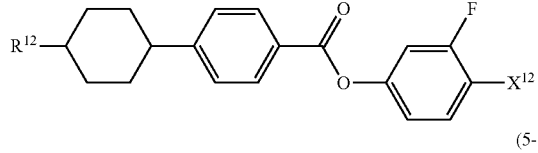
(5-50) 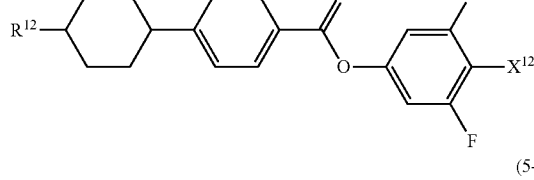
(5-51) 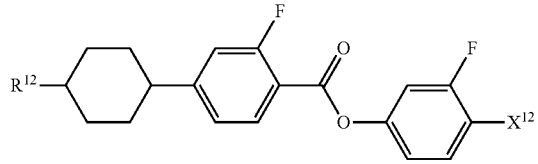
(5-52) 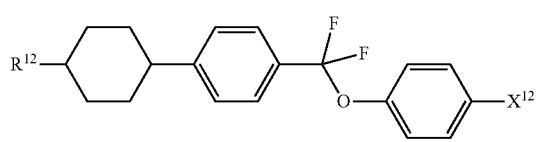
(5-53) 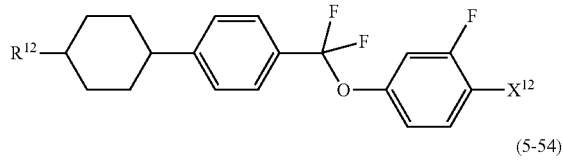
(5-54) 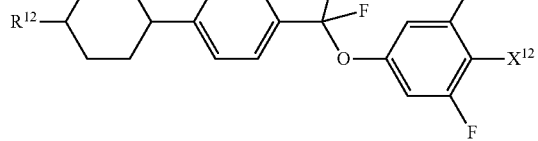
(5-55) 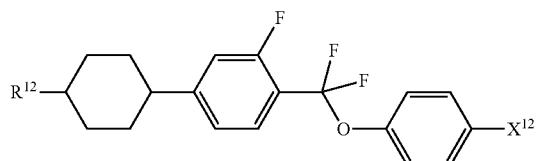

In the compounds (component C), $R^{12}$ and $X^{12}$ are defined in a manner identical with the definition in formula (5) described in item 12.

Component C has the positive dielectric anisotropy a value of which is large, and therefore is mainly used for preparing a composition for an STN mode, a TN mode or the PSA mode. The dielectric anisotropy of the composition can be increased by adding component C. Component C is effective in extending the temperature range of the liquid crystal phase, adjusting the viscosity or adjusting the optical anisotropy. Component C is also useful for adjusting a voltage-transmittance curve of the device.

When a composition for the STN mode or the TN mode is prepared, a content of component C is suitably in the range of approximately 1 to approximately 99% by weight, preferably in the range of approximately 10 to approximately 97% by weight, and further preferably in the range of approximately 40 to approximately 95% by weight, based on the total weight of the composition. In the composition, the temperature range of the liquid crystal phase, the viscosity, the optical anisotropy, the dielectric anisotropy and so forth can be adjusted by adding component E.

Component D includes compounds (6) to (12). The compounds have a benzene ring in which hydrogen in a lateral position are replaced by two halogen atoms, such as 2,3-difluoro-1,4-phenylene. Preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3).

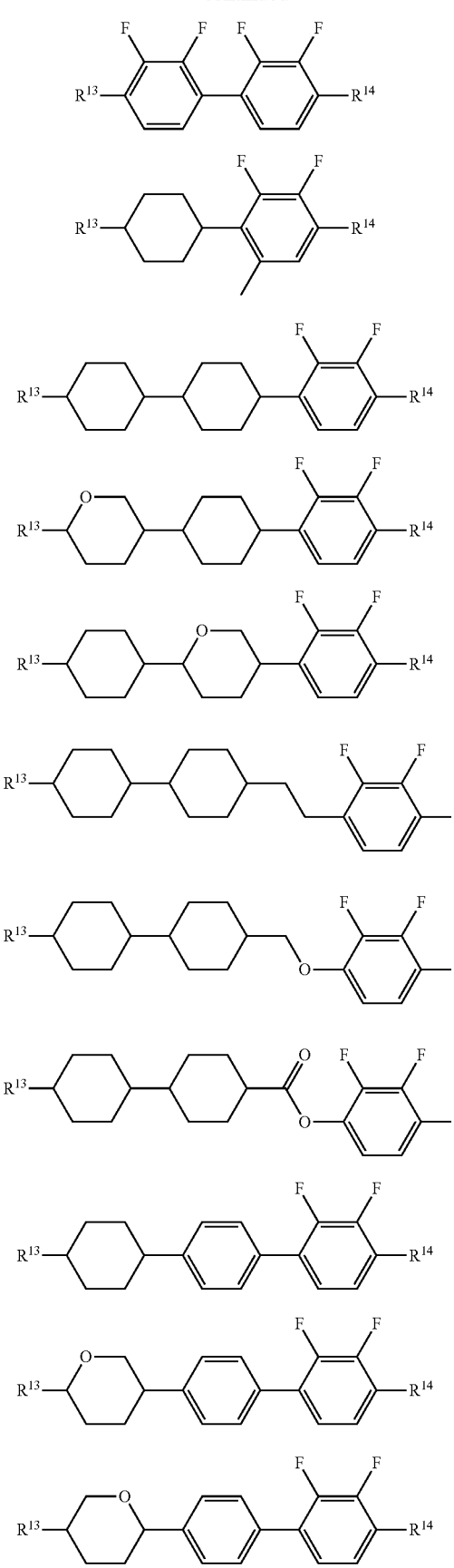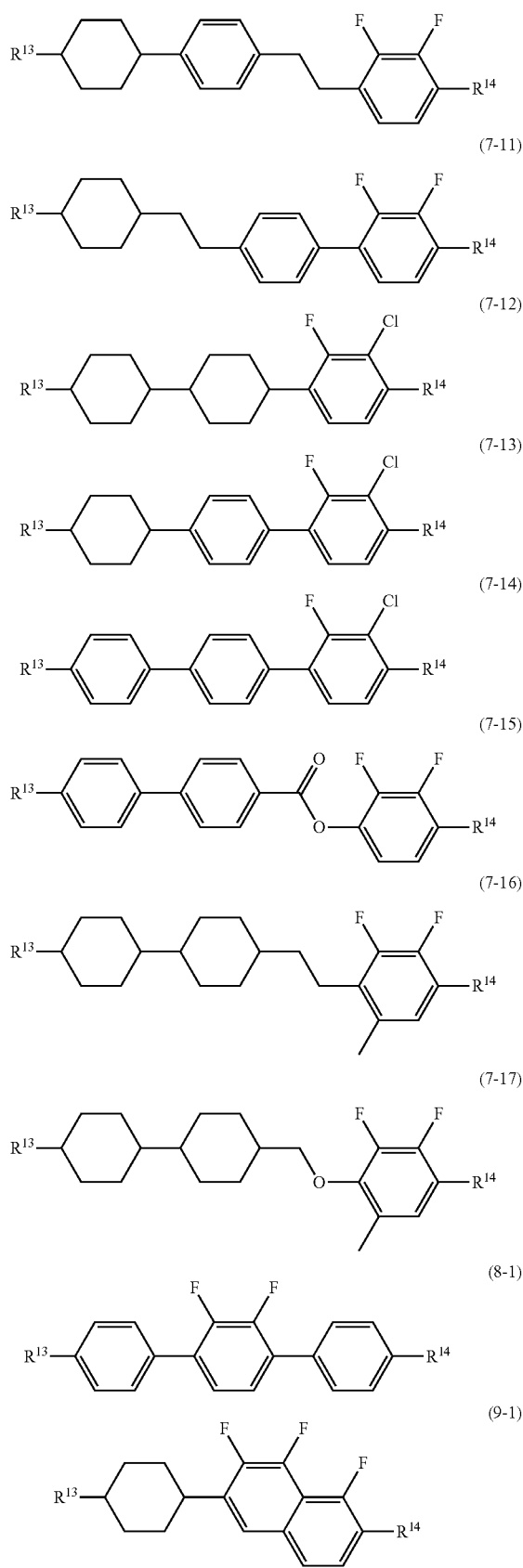

(9-2)
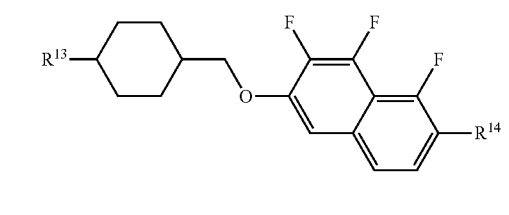
(9-3)
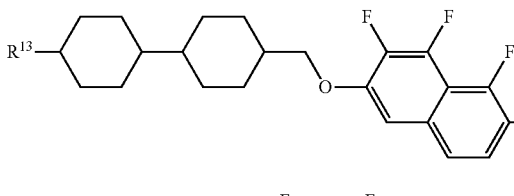
(10-1)
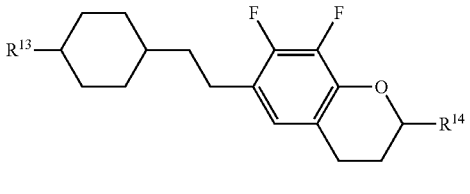
(10-2)
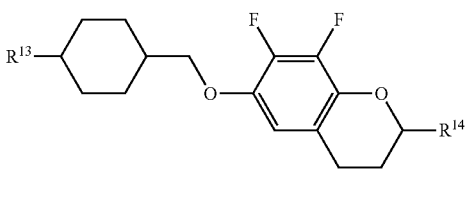
(10-3)
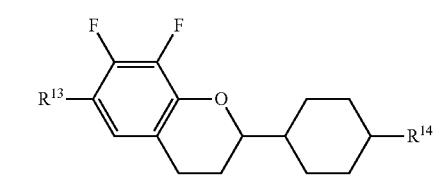
(10-4)
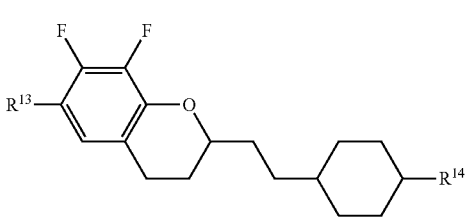
(10-5)
(10-6)
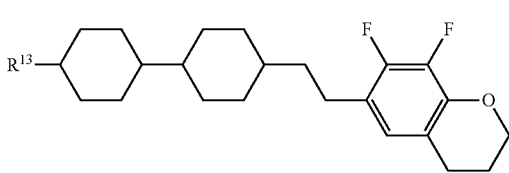
(10-7)
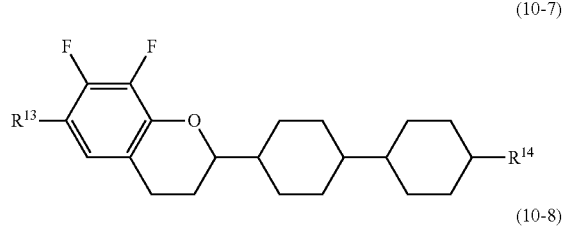
(10-8)
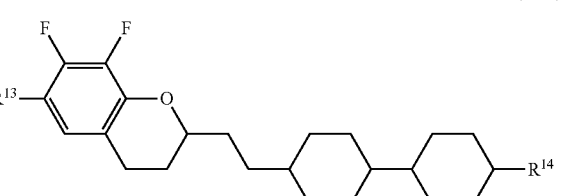
(10-9)
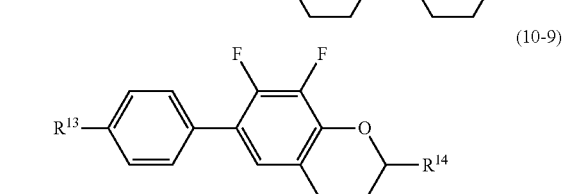
(10-10)
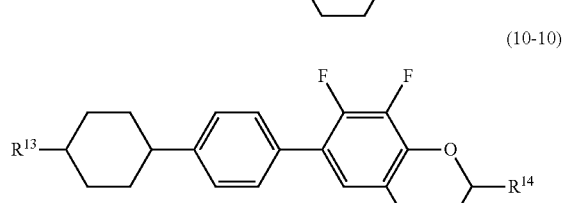
(10-11)
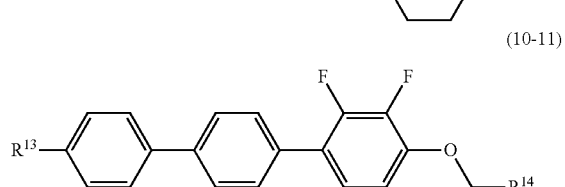
(11-1)
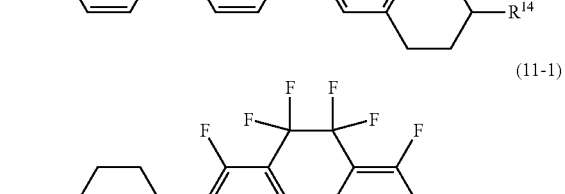
(11-2)
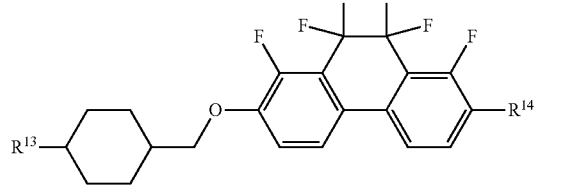
(11-3)
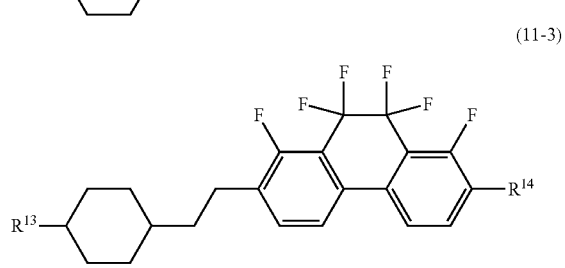

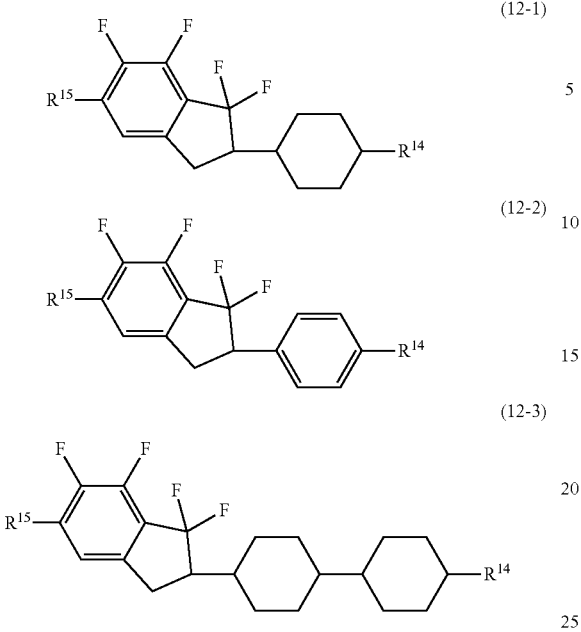

(12-1)
(12-2)
(12-3)

In the compounds (component D), $R^{13}$, $R^{14}$ and $R^{15}$ are defined in a manner identical with the definitions in formulas (6) to (12) described in item 9.

Component D is a compound having the negative dielectric anisotropy. Component D is mainly used for preparing a composition for a VA mode or the PSA mode. Among types of component D, compound (6) is a bicyclic compound, and therefore is effective mainly in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When the composition for the VA mode or the PSA mode is prepared, a content of component D is preferably approximately 40% by weight or more, and further preferably in the range of approximately 50 to approximately 95% by weight, based on the total weight of the composition. When component D is added to the composition having the positive dielectric anisotropy, a content of component D is preferably approximately 30% by weight or less based on the total weight of the composition. Addition of component D allows adjustment of the elastic constant of the composition and the voltage-transmittance curve of the device.

Component E is a compound in which two terminal groups are alkyl or the like. Preferred examples of component E include compounds (13-1) to (13-11), compounds (14-1) to (14-19) and compounds (15-1) to (15-7)

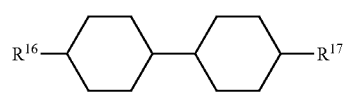
(13-1)

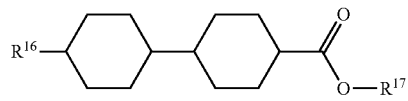
(13-2)

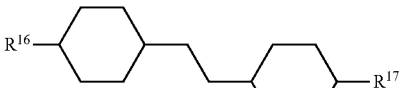
(13-3)

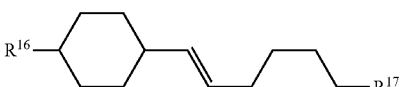
(13-4)

(13-5)
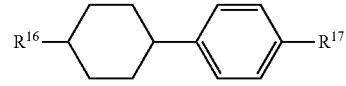

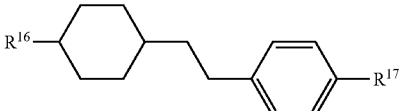
(13-6)

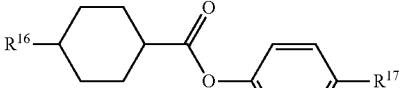
(13-7)

(13-8)
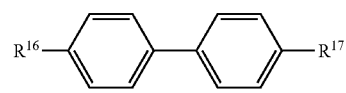

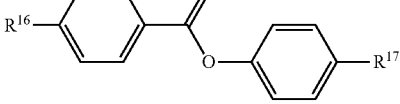
(13-9)

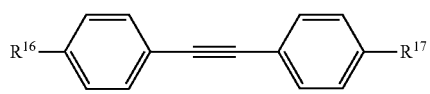
(13-10)

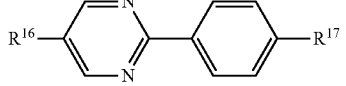
(13-11)

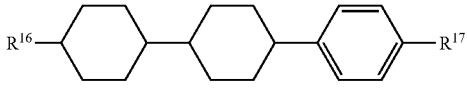
(14-1)

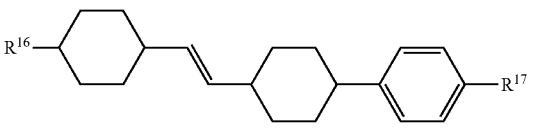
(14-2)

(14-3)

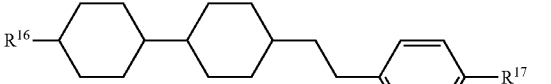
(14-4)

(14-5) (14-6) (14-7) (14-8) (14-9) (14-10) (14-11) (14-12) (14-13) (14-14) (14-15) (14-16) (14-17) (14-18) (14-19) (15-1) (15-2) (15-3) (15-4) (15-5) (15-6) (15-7)

In the compounds (component E), $R^{16}$ and $R^{17}$ are defined in a manner identical with the definitions in formulas (13) to (15) described in item 10.

Component E has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or effective in adjusting the optical anisotropy.

When a content of component E is increased, the viscosity of the composition decreases, but the dielectric anisotropy also decreases. Then, the content is desirably as large as possible, as long as a desired value of threshold voltage of the device is met. Therefore, when a composition for the VA mode or the PSA mode is prepared, the content of component E is preferably approximately 30% by weight or more, and further preferably approximately 40% by weight or more, based on the total weight of the composition.

Preparation of composition (1) is performed by a method for dissolving required components at a high temperature, or the like. According to an application, an additive may be added to the composition. Examples of the additive include an optically active compound, a polymerizable compound, a polymerization initiator, an antioxidant, an ultraviolet light absorber, a light stabilizer, a heat stabilizer and a defoaming agent. Such additives are well known to those skilled in the art, and described in literature.

Composition (1) may further contain at least one optically active compound. A publicly known chiral dopant can be added as the optically active compound. The chiral dopant is effective in inducing helical structure in liquid crystal molecules to give a necessary twist angle, thereby preventing a reverse twist. Preferred examples of the chiral dopant include compounds (Op-1) to (Op-18) described below. In compound (Op-18), ring J is 1,4-cyclohexylene or 1,4-phenylene, and $R^{24}$ is alkyl having 1 to 10 carbons.

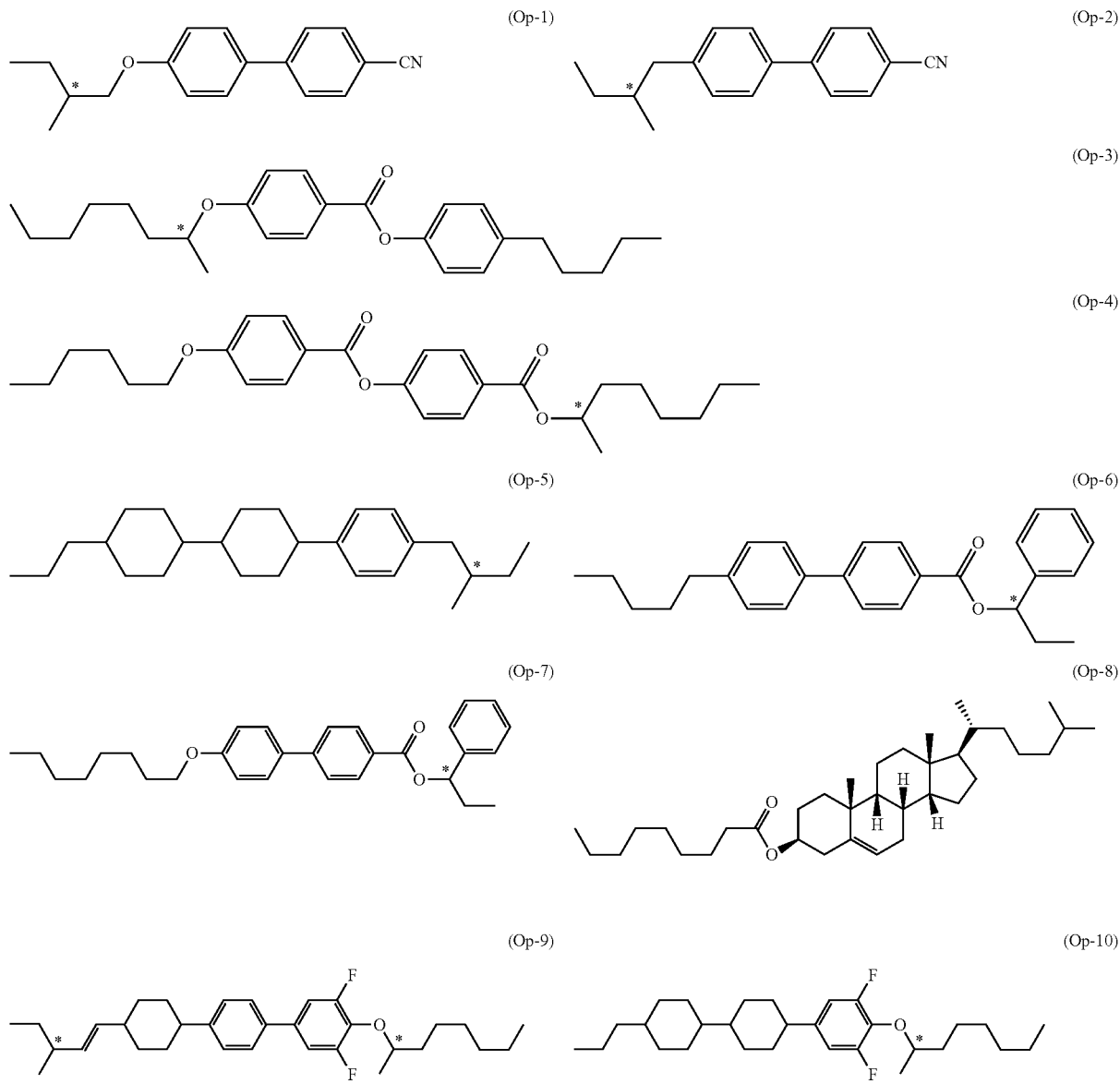

-continued

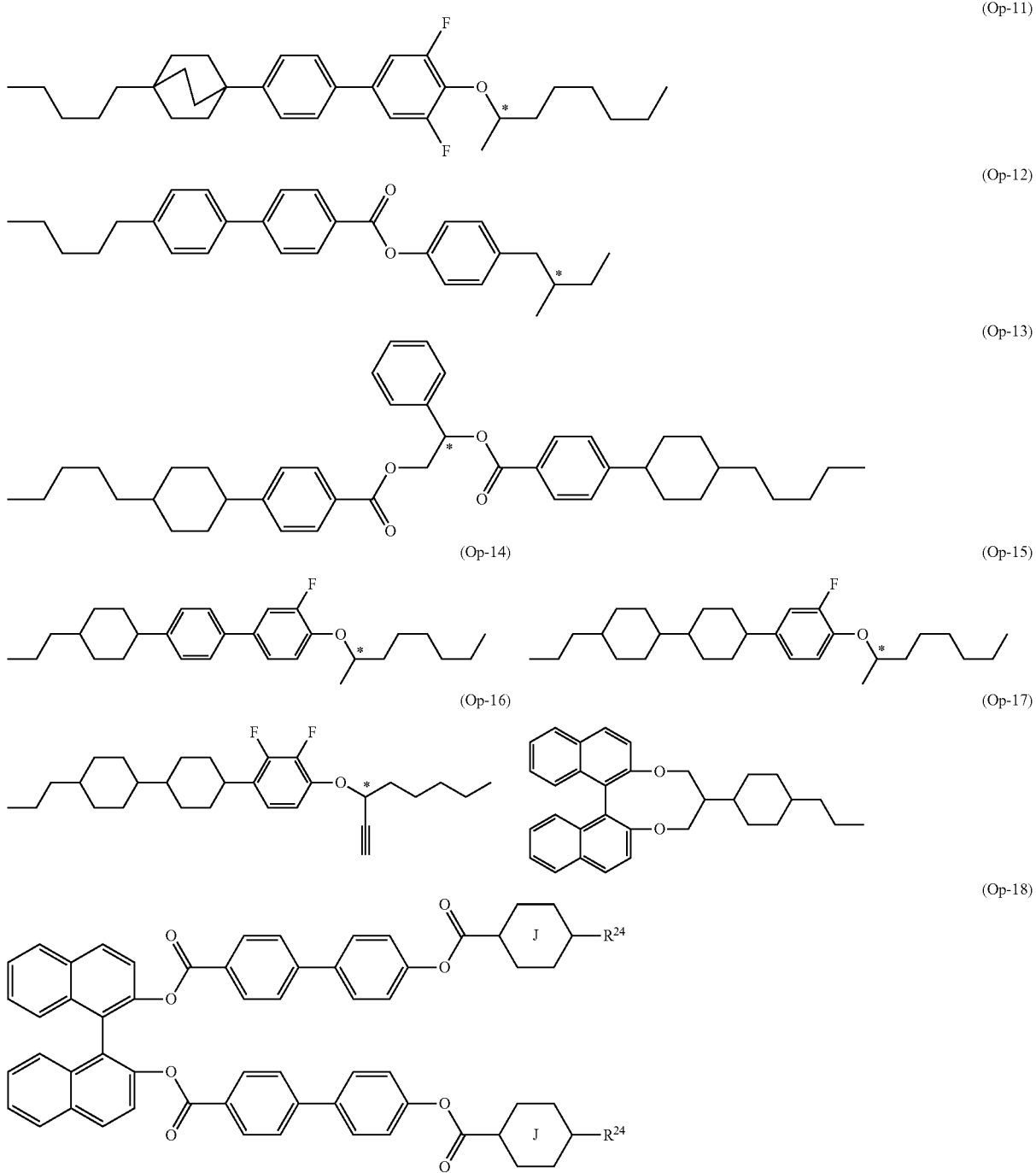

In composition (1), a helical pitch is adjusted by adding such an optically active compound. The helical pitch is preferably adjusted in the range of approximately 40 to approximately 200 micrometers in a composition for the TFT mode and the TN mode. In a composition for the STN mode, the helical pitch is preferably adjusted in the range of approximately 6 to approximately 20 micrometers. In the case of a composition for a BTN mode, the helical pitch is preferably adjusted in the range of approximately 1.5 to approximately 4 micrometers. For the purpose of adjusting temperature dependence of the helical pitch, two or more optically active compounds may be added thereto.

Composition (1) can also be used for the PSA mode by adding the polymerizable compound. Examples of the polymerizable compound include acrylate, methacrylate, a vinyl compound, a vinyloxy compound, propenyl ether, an epoxy compound (oxirane, oxetane) and vinyl ketone. Preferred examples include compounds (M-1) to (M-12) described below. The polymerizable compound is polymerized by irradiation with ultraviolet light or the like. The compound may be polymerized in the presence of a suitable initiator such as a photopolymerization initiator. Suitable conditions for polymerization, suitable types of the initiator and suitable amounts thereof are known to those skilled in the art and are described in literature.
In compounds (M-1) to (M-12), $R^{20}$ is hydrogen or methyl; s is 0 or 1; and t and u are independently an integer from 1 to 10. Parenthesized symbol F means hydrogen or fluorine.
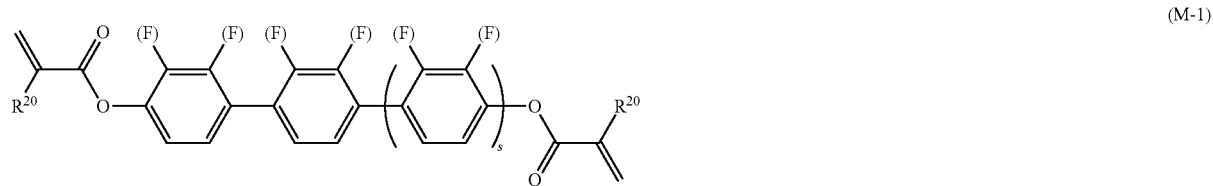
(M-1)
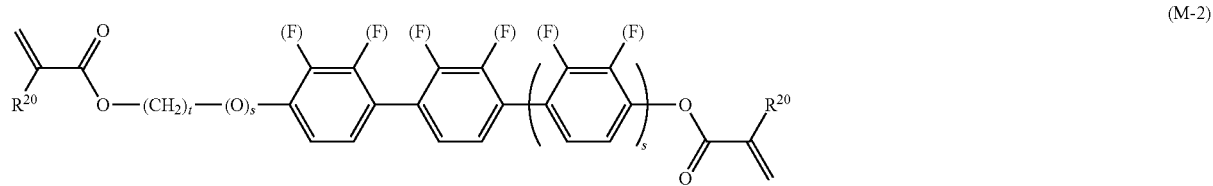
(M-2)
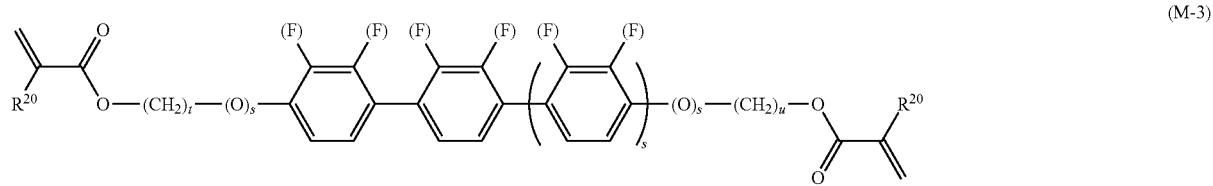
(M-3)
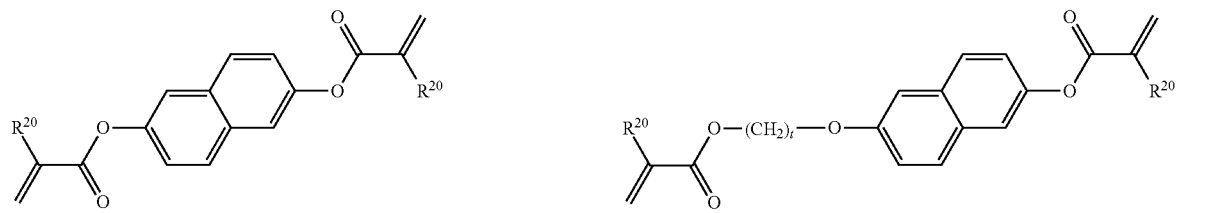
(M-4) (M-5)
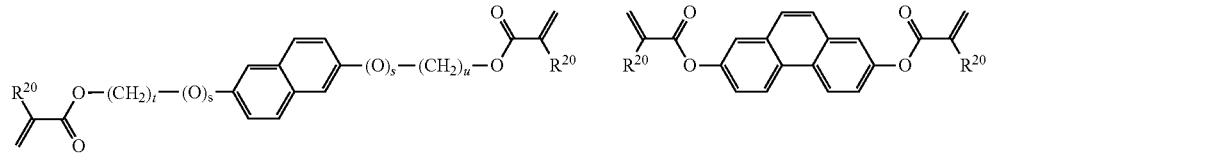
(M-6) (M-7)
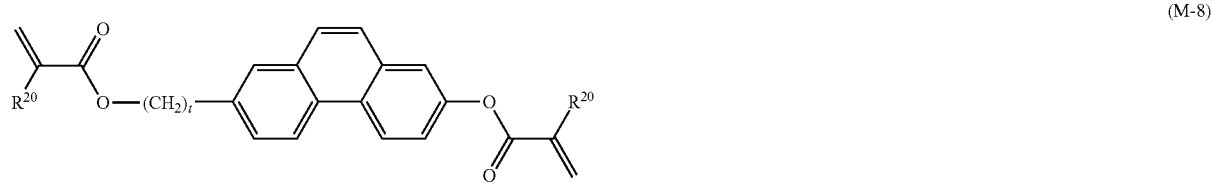
(M-8)
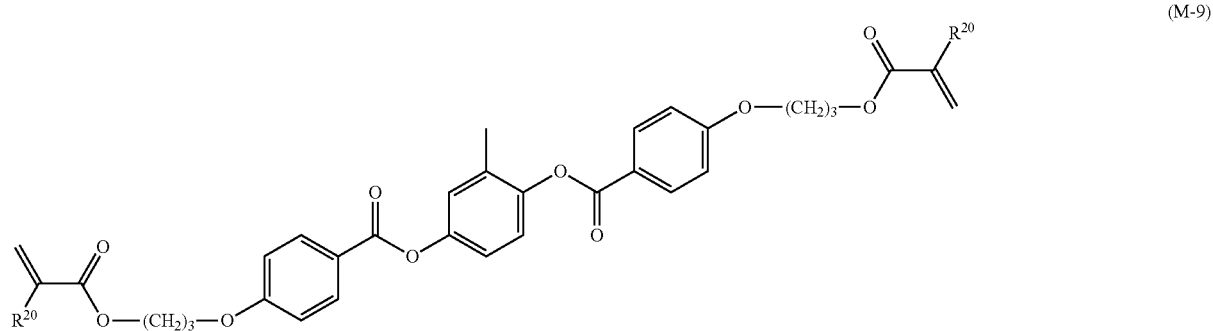
(M-9)

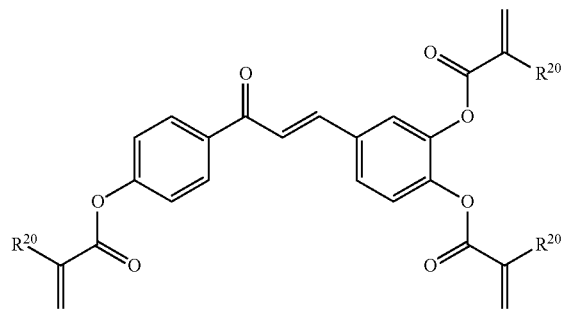
(M-10)

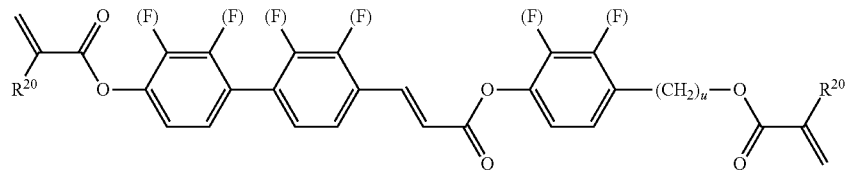
(M-11)

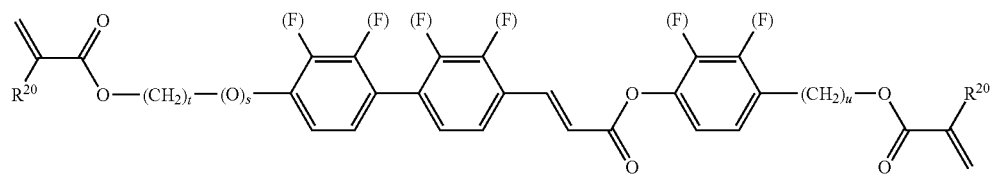
(M-12)

The antioxidant is effective for maintaining a large voltage holding ratio. Preferred examples of the antioxidant include compounds (AO-1) and (AO-2) described below; and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease in the maximum temperature. Preferred examples of the ultraviolet light absorber include a benzophenone derivative, a benzoate derivative and a triazole derivative. Specific examples include compounds (AO-3) and (AO-4) described below; TINUVIN329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO)

A light stabilizer such as an amine having steric hindrance is preferred for maintaining the large voltage holding ratio. Preferred examples of the light stabilizer include compounds (AO-5) and (AO-6) described below; and TINUVIN 144, TINUVIN 765 and TINUVIN 77055 (trade names: BASF SE). The heat stabilizer is also effective for maintaining the large voltage holding ratio, and preferred examples include Irgafos 168 (trade name: BASF SE). The defoaming agent is effective for preventing foam formation. Preferred examples of the defoaming agent include dimethyl silicone oil and methylphenyl silicone oil.

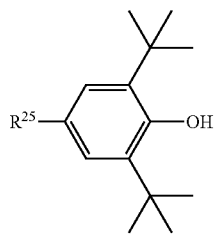
(AO-1)

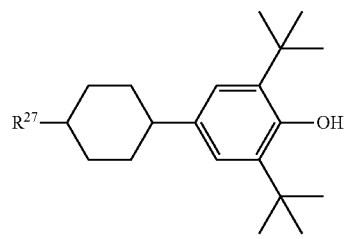
(AO-2)

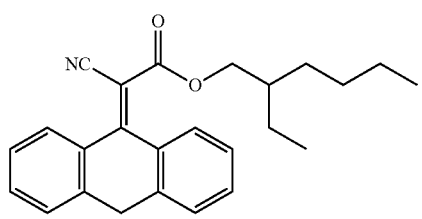
(AO-3)

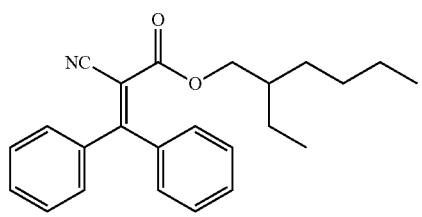
(AO-4)

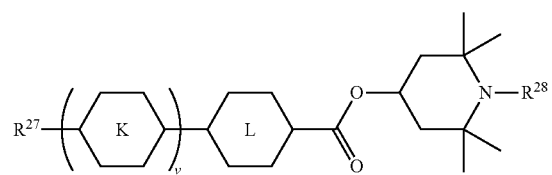
(AO-5)

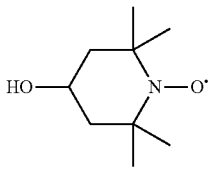
(AO-6)

In compound (AO-1), $R^{25}$ is alkyl having 1 to 20 carbons, alkoxy having 1 to 20 carbons, —COOR$^{26}$ or —CH$_2$CH$_2$COOR$^{26}$; and R$^{26}$ is alkyl having 1 to 20 carbons. In compounds (AO-2) and (AO-5), $R^{27}$ is alkyl having 1 to 20 carbons. In compound (AO-5), ring K and ring L are 1,4-cyclohexylene or 1,4-phenylene, v is 0, 1 or 2, and $R^{28}$ is hydrogen, methyl or O. (oxygen radical).

Composition (1) can also be used for a guest host (GH) mode by addition of a dichroic dye such as a merocyanine type, a styryl type, an azo type, an azomethine type, an azoxy type, a quinophthalone type, an anthraquinone type and a tetrazine type.

In composition (1), the maximum temperature can be adjusted to approximately 70° C. or higher and the minimum temperature can be adjusted to approximately −10° C. or lower by suitably adjusting a kind and a ratio of component compounds, and therefore the temperature range of the nematic phase is wide. Accordingly, a liquid crystal display device including the composition can be used in the wide temperature range.

In composition (1), the optical anisotropy can be adjusted to the range of approximately 0.10 to approximately 0.13 or approximately 0.05 to approximately 0.18 by suitably adjusting a kind and a ratio of the component compounds. In a similar manner, the dielectric anisotropy can be adjusted to the range of approximately −5.0 to approximately −2.0. A preferred dielectric anisotropy is in the range of approximately −4.5 to approximately −2.5. Composition (1) having the dielectric anisotropy in the above range can be preferably used in a liquid crystal display device that operates in an IPS mode, the VA mode or the PSA mode.

3. Liquid Crystal Display Device

Composition (1) can be used for an AM device. The composition can also be used for a PM device. The composition can be used for an AM device and a PM device each having a mode such as PC, TN, STN, ECB, OCB, IPS, FFS, VA, PSA or FPA. Use for an AM device having the TN, OCB, IPS or FFS mode is particularly preferred. In an AM device having the IPS or FFS mode, alignment of liquid crystal molecules in a state in which no voltage is applied may be parallel or perpendicular to a panel substrate. The device may be of a reflective type, a transmissive type or a transflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, and for a polymer dispersed (PD) device in which a three-dimensional network polymer is formed in the composition.

Composition (1) has the negative dielectric anisotropy, and therefore can be preferably used for a liquid crystal display device that has an operating mode such as the VA mode, the IPS mode or the PSA mode and is driven by an AM mode. The composition can be particularly preferably used for a liquid crystal display device that has the VA mode and is driven by the AM mode.

In a liquid crystal display device that operates in the TN mode, the VA mode or the like, a direction of an electric field is perpendicular to a direction of a liquid crystal layer. On the other hand, in a liquid crystal display device that operates in the IPS mode or the like, the direction of the electric field is parallel to the direction of the liquid crystal layer. A structure of a liquid crystal display device that operates in the VA mode is reported by K. Ohmuro, S. Kataoka, T. Sasaki and Y. Koike, SID '97 Digest of Technical Papers, 28, 845 (1997). A structure of a liquid crystal display device that operates in the IPS mode is reported in WO 91/10936 A (family: U.S. Pat. No. 5,576,867 B).

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. However, the invention is not limited by the Examples.

1-1. Example of Compound (1-1)

Compound (1-1) was prepared according to procedures described below. The prepared compound was identified by a method such as an NMR analysis. Physical properties of the compound were measured by the method described below.

NMR Analysis

As a measuring apparatus, DRX-500 (made by Bruker BioSpin Corporation) was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In measurement of $^{19}$F-NMR, measurement was carried out using CFCl$_3$ as an internal standard and under conditions of 24 times of accumulation. In explanation of nuclear magnetic resonance spectra, symbols s, d, t, q, quin, sex, m and br stand for a singlet, a doublet, a triplet, a quartet, a quintet, a sextet, a multiplet, and being broad, respectively.

Sample for Measurement

When phase structure and transition temperature were measured, a liquid crystal compound itself was used as a sample. When physical properties such as a maximum temperature of a nematic phase, viscosity, optical anisotropy and dielectric anisotropy were measured, a composition prepared by mixing the compound with a base liquid crystal was used as a sample.

When the sample in which the compound was mixed with the base liquid crystal was used, measurement was carried out according to a method described below. The sample was prepared by mixing 15% by weight of the compound and 85% by weight of the base liquid crystal. Then, extrapolated values were calculated from measured values of the sample, according to an extrapolation method represented by an equation below, and the extrapolated values were described. {Extrapolated value}={100×(measured value of a sample)−(% by weight of base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal was changed in the order of (10% by weight: 90% by weight), (5% by weight: 95% by weight) and (1% by weight: 99% by weight), and physical properties of the sample were measured at a ratio at which no crystals (or no smectic phase) precipitated at 25° C. In addition, unless otherwise noted, the ratio of the compound to the base liquid crystal was 15% by weight: 85% by weight.

As the base liquid crystal, base liquid crystal (i) described below was used. Ratios of components of base liquid crystal (i) are expressed in terms of % by weight.

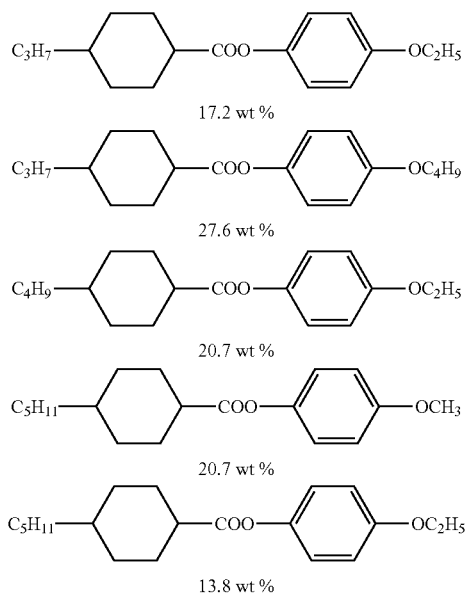

Measurement Methods

Physical properties were measured according to methods described below. Most of the methods are applied as described in the Standard of the Japan Electronics and Information Technology Industries Association (hereinafter, abbreviated as JEITA) (JEITA ED-2521A) discussed and established by JEITA, or as modified thereon. No TFT was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

A sample was heated and then cooled at a rate of 3° C. per minute using a differential scanning calorimeter, DSC-7 System or Diamond DSC System, made by PerkinElmer, Inc., and a starting point of an endothermic peak or an exothermic peak caused by a change of phases of the sample was determined by extrapolation, and thus a transition temperature was determined. Temperature at which a compound undergoes transition from a solid to a liquid crystal phase such as a smectic phase and a nematic phase may be occasionally abbreviated as "minimum temperature of the liquid crystal phase." Temperature at which a compound undergoes transition from the liquid crystal phase to a liquid may be occasionally abbreviated as "clearing point."

Crystals were expressed as C. When kinds of the crystals were distinguishable, each of the crystals was expressed as $C_1$ or $C_2$. The smectic phase was expressed as S, and the nematic phase was expressed as N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. The transition temperature was expressed as "C 50.0 N 100.0 I," for example. The expression indicates that the transition temperature from the crystal to the nematic phase is 50.0° C., and the transition temperature from the nematic phase to the liquid is 100.0° C.

(3) Compatibility at a Low Temperature

Samples in which the base liquid crystal and the compound were mixed such that a ratio of the compound was 20% by weight, 15% by weight, 10% by weight, 5% by weight, 3% by weight or 1% by weight were prepared, and placed in glass vials. After the glass vials were kept in freezers at −10° C. or −20° C. for a predetermined period of time, whether or not crystals (or a smectic phase) precipitated was observed.

(4) Maximum Temperature of Nematic Phase ($T_{NI}$ or NI; ° C.)

A sample was placed on a hot plate in a melting point apparatus equipped with a polarizing microscope and was heated at a rate of 1° C. per minute. Temperature was measured when part of the sample began to change from a nematic phase to an isotropic liquid. A higher limit of a temperature range of the nematic phase may be occasionally abbreviated as "maximum temperature." When the sample was a mixture of a compound and a base liquid crystal, the maximum temperature was expressed using a symbol $T_{NI}$. When the sample was a mixture of a compound, component B and so forth, the maximum temperature was expressed using a symbol NI.

(5) Minimum Temperature of Nematic Phase ($T_C$; ° C.)

Samples each having a nematic phase were kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_c$ was expressed as $T_c \leq -20°$ C. A lower limit of the temperature range of the nematic phase may be occasionally abbreviated as "minimum temperature."

(6) Viscosity (Bulk Viscosity; η; Measured at 20° C.; mPa·s)

Measurement was carried out using a cone-plate (E type) rotational viscometer.

(7) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a VA device in which a distance (cell gap) between two glass substrates was 20 micrometers. Voltage was applied stepwise to the device in the range of 30 V to 50 V at an increment of 1 V. After a period of 0.2 second with no voltage application, voltage was applied repeatedly under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. As a value of dielectric anisotropy necessary for the calculation, a value measured in a section of dielectric anisotropy as described below was used.

(8) Optical Anisotropy (Refractive Index Anisotropy; Measured at 25° C.; Δn)

Measurement was carried out by an Abbe refractometer having a polarizing plate mounted on an ocular by using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥–n⊥.

(9) Dielectric Anisotropy (Δ∈; Measured at 25° C.)

A value of dielectric anisotropy was calculated from an equation: Δ∈=∈∥–∈⊥. Dielectric constants (∈∥ and ∈⊥) were measured as described below.

(1) Measurement of dielectric constant (∈∥): An ethanol (20 mL) solution of octadecyl triethoxysilane (0.16 mL) was applied to a well-cleaned glass substrate. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (d) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(10) Elastic Constant ($K_{11}$ and $K_{33}$; Measured at 25° C.; pN)

For measurement, Elastic Constant Measurement System Model EC-1 made by TOYO Corporation was used. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was antiparallel, and the device was sealed with an ultraviolet-curable adhesive. A voltage (60 Hz, rectangular waves) applied to the device was increased stepwise from 0 V to 20 V at an increment of 0.02 V. On the occasion, the device was irradiated with light from a direction perpendicular to the device, and an amount of light transmitted through the device was measured. A voltage-transmittance curve was prepared, in which the maximum value of the amount of light corresponded to 100% transmittance and the minimum value of the amount of light corresponded to 0% transmittance. A threshold voltage was voltage at 10% transmittance.

(12) Voltage Holding Ratio (VHR-1; Measured at 25° C.; %)

A TN device used for measurement had a polyimide alignment film, in which a distance (cell gap) between two glass substrates was 5 micrometers. A sample was put in the device, and then the device was sealed with an ultraviolet-curable adhesive. The TN device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio was a percentage of area A to area B.

(13) Voltage Holding Ratio (VHR-2; Measured at 80° C.; %)

A TN device used for measurement had a polyimide alignment film, in which a distance (cell gap) between two glass substrates was 5 micrometers. A sample was put in the device, and then the device was sealed with an ultraviolet-curable adhesive. The TN device was charged by applying a pulse voltage (60 microseconds at 5 V). A decaying voltage was measured for 16.7 milliseconds with a high-speed voltmeter, and area A between a voltage curve and a horizontal axis in a unit cycle was obtained. Area B was an area without decay. A voltage holding ratio was a percentage of area A to area B.

Raw Material

Solmix (registered trademark) A-11 is a mixture of ethanol (85.5%), methanol (13.4%) and isopropanol (1.10), and was obtained from Japan Alcohol Trading Co., Ltd.

Example 1

Synthesis of Compound (1-1-1)

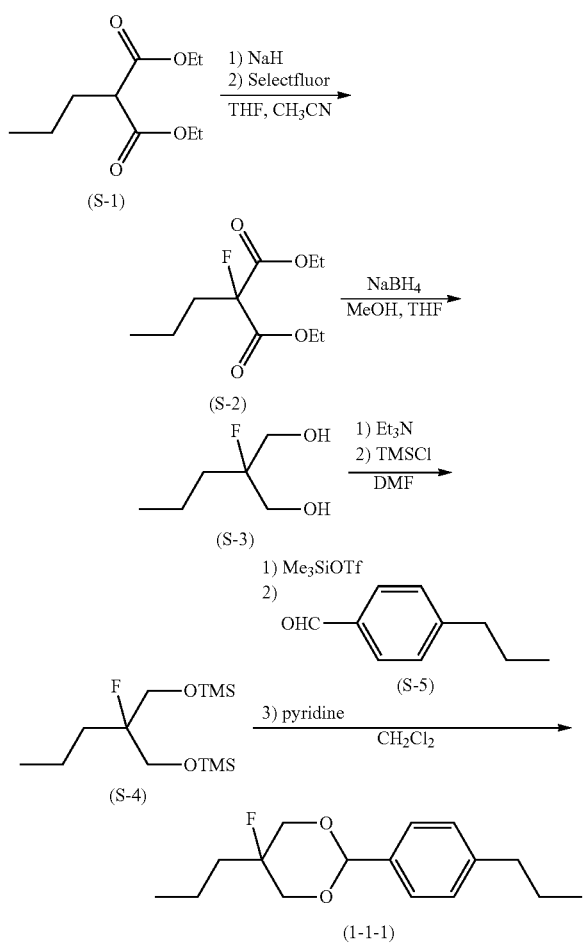

First Step

Under a nitrogen atmosphere, sodium hydride (3.24 g) and THF (80 mL) were put in a reaction vessel, and the resulting mixture was cooled to 0° C. A THF (20 mL) solution of compound (S-1) (10.0 g) was slowly added thereto, and the resulting mixture was stirred for 2 hours. The resulting reaction mixture was heated to 45° C., and then stirred at room temperature for 18 hours. The resulting reaction mixture was cooled to 0° C., an acetonitrile (100 mL) suspension of Selectfluor (22.7 g) was added thereto, and the resulting mixture was stirred for 2 hours, and then heated to room temperature. The resulting reaction mixture was poured into water, and an aqueous layer was subjected to extraction with ethyl acetate. Organic layers combined were washed with water, a 1 N hydrochloric acid solution, saturated sodium bicarbonate water and saturated brine, and dried over anhydrous magnesium sulfate. The resulting solution was concentrated under reduced pressure, and the residue was purified by silica gel column chromatography (heptane:ethyl acetate=4:1 in a volume ratio) to give compound (S-2) (7.79 g; 72%).

Second Step

Under a nitrogen atmosphere, compound (S-2) (7.29 g), methanol (40 mL) and THF (10 mL) were put in a reaction vessel, and the resulting mixture was stirred at room temperature. Sodium borohydride (6.26 g) was added little by little thereto, and the resulting mixture was stirred for 2 hours. The resulting reaction mixture was poured into a saturated aqueous solution of ammonium chloride, and an aqueous layer was subjected to extraction with ether. Organic layers combined were washed with saturated brine, and dried over anhydrous magnesium sulfate. The resulting solution was concentrated under reduced pressure to give a crude product of compound (S-3) (2.05 g; 670).

Third Step

Under a nitrogen atmosphere, compound (S-3) (3.21 g), triethylamine (18.1 mL) and N,N-dimethylformamide (30 mL) were put in a reaction vessel, and the resulting mixture was stirred at room temperature. Chlorotrimethylsilane (8.28 mL) was slowly added thereto, and the resulting mixture was stirred for 1 hour. The resulting reaction mixture was poured into water, and an aqueous layer was subjected to extraction with ether. Organic layers combined were washed with water and saturated brine, and dried over anhydrous magnesium sulfate. The resulting solution was concentrated under reduced pressure to give a crude product of compound (S-4) (3.12 g; 69%).

Fourth Step

Under a nitrogen atmosphere, compound (S-4) (2.88 g), trimethylsilyl trifluoromethanesulfonate (0.17 mL) and dichloromethane (15 mL) were put in a reaction vessel, and the resulting mixture was cooled to −70° C. A dichloromethane (5 mL) solution of compound (S-5) (1.73 g) prepared according to a publicly known method was slowly added thereto, and the resulting mixture was stirred for 2 hours. Pyridine (1.08 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (heptane:ethyl acetate=10:1 in a volume ratio). The residue was further purified by recrystallization from a mixed solvent of heptane and 2-propanol (1:1 in a volume ratio) to give compound (1-1-1) having fluorine atom in axial position (1.31 g; 48%).

Chemical shifts δ (ppm; CDCl$_3$): 7.42 (d, J=8.1 Hz, 2H), 7.18 (d, J=8.1, 2H), 5.45 (s, 1H), 4.23 (dd, J=12.6, J=11.6, 2H), 3.86 (dd, J=35.1, J=12.6, 2H), 2.58 (t, J=7.7 Hz, 2H), 1.65-1.41 (m, 6H), 0.98-0.89 (m, 6H).

Physical properties of compound (1-1-1) were as described below.

Transition temperature: C 82.7 I.

Maximum temperature ($T_{NI}$)=−7.4° C.; optical anisotropy (Δn)=0.0657; dielectric anisotropy (Δ∈)=−3.98; and viscosity (η)=57.4 mPa·s.

Example 2

Synthesis of Compound (1-1-4)

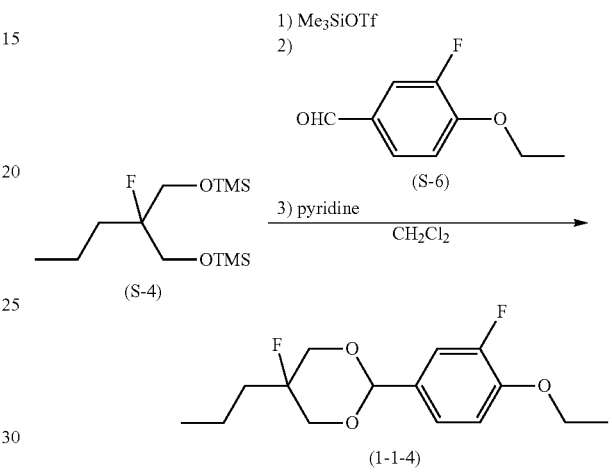

First Step

Under a nitrogen atmosphere, compound (S-4) (2.42 g), trimethylsilyl trifluoromethanesulfonate (0.14 mL) and dichloromethane (15 mL) were put in a reaction vessel, and the resulting mixture was cooled to −70° C. A dichloromethane (10 mL) solution of compound (S-6) (1.65 g) prepared according to a publicly known method was slowly added thereto, and the resulting mixture was stirred for 2 hours. Pyridine (0.91 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (toluene:ethyl acetate=4:1 in a volume ratio). The residue was further purified by recrystallization from a mixed solvent of heptane and ethyl acetate (1:1 in a volume ratio) to give compound (1-1-4) having fluorine atom in axial position (0.86 g; 35%).

Chemical shifts δ (ppm; CDCl$_3$): 7.27 (dd, J=10.3 Hz, J=1.95, 1H), 7.21 (d, J=8.4, 1H), 6.93 (t, J=8.5 Hz, 1H), 5.40 (s, 1H), 4.22 (dd, J=12.7, J=11.9, 2H), 4.10 (q, J=7.1 Hz, 2H), 3.90-3.77 (m, 2H), 1.54-1.41 (m, 7H), 0.99-0.93 (m, 3H).

Physical properties of compound (1-1-4) were as described below. In addition, for measurement of maximum temperature, optical anisotropy, dielectric anisotropy and viscosity, a sample in which a ratio of the compound to the base liquid crystal was 5% by weight: 95% by weight was used.

Transition temperature: C 107.3 I.

Maximum temperature ($T_{NI}$)=24.6° C.; optical anisotropy (Δn)=0.107; dielectric anisotropy (Δ∈)=−4.84; and viscosity (η)=77.0 mPa·s.

Example 3

Synthesis of Compound (1-2-1)

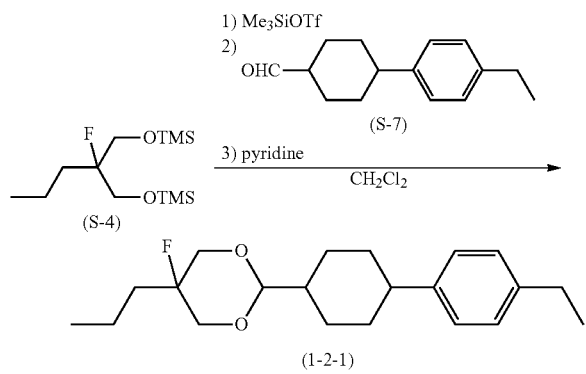

First Step

Under a nitrogen atmosphere, compound (S-4) (4.00 g), trimethylsilyl trifluoromethanesulfonate (0.23 mL) and dichloromethane (25 mL) were put in a reaction vessel, and the resulting mixture was cooled to −70° C. A dichloromethane (15 mL) solution of compound (S-7) (3.52 g) prepared according to a publicly known method was slowly added thereto, and the resulting mixture was stirred for 2 hours. Pyridine (1.50 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (heptane:ethyl acetate=10:1 in a volume ratio). The residue was further purified by recrystallization from heptane to give compound (1-2-1) having fluorine atom in axial position (0.95 g; 20%).

Chemical shifts δ (ppm; CDCl$_3$): 7.12 (s, 4H), 4.25 (d, J=5.7, 1H), 4.09 (dd, J=12.5, J=11.7, 2H), 3.63 (dd, J=35.3, J=12.6, 2H), 2.61 (q, J=7.6 Hz, 2H), 2.44 (tt, J=12.2, J=3.4, 1H), 2.04-1.90 (m, 4H), 1.73-1.64 (m, 1H), 1.49-1.37 (m, 6H), 1.29-1.18 (m, 5H), 0.94 (t, J=6.6 Hz, 3H).

Physical properties of compound (1-2-1) were as described below. In addition, for measurement of maximum temperature, optical anisotropy, dielectric anisotropy and viscosity, a sample in which a ratio of the compound to the base liquid crystal was 10% by weight: 90% by weight was used.

Transition temperature: C 131.4 I.

Maximum temperature (T$_{NI}$)=97.6° C.; optical anisotropy (Δn)=0.100; dielectric anisotropy (Δ∈)=−3.05; and viscosity (η)=64.2 mPa·s.

Example 4

Synthesis of Compound (1-2-30)

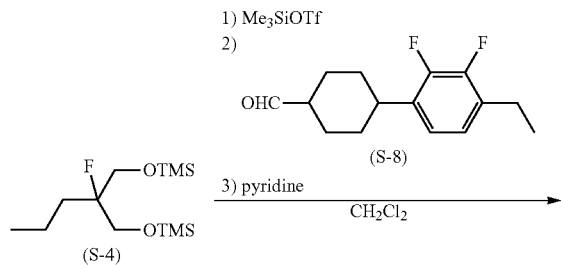

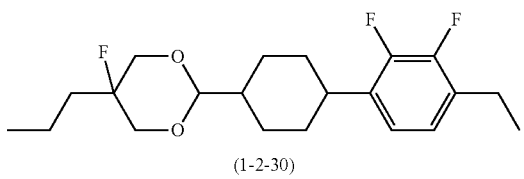

First Step

Under a nitrogen atmosphere, compound (S-4) (2.25 g), trimethylsilyl trifluoromethanesulfonate (0.13 mL) and dichloromethane (15 mL) were put in a reaction vessel, and the resulting mixture was cooled to −70° C. A dichloromethane (5 mL) solution of compound (S-8) (2.25 g) prepared according to a publicly known method was slowly added thereto, and the resulting mixture was stirred for 2 hours. Pyridine (0.84 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (heptane:ethyl acetate=9:1 in a volume ratio). The residue was further purified by recrystallization from a mixed solvent of heptane and ethyl acetate (1:1 in a volume ratio) to give compound (1-2-30) having fluorine atom in axial position (1.38 g; 47%).

Chemical shifts δ (ppm; CDCl$_3$): 7.60 (d, J=8.3, 2H), 7.56-7.52 (m, 2H), 7.11-7.06 (m, 1H), 7.02-6.97 (m, 1H), 5.53 (s, 1H), 4.26 (dd, J=12.5, J=11.7, 2H), 3.89 (dd, J=34.9, J=12.7, 2H), 2.73 (q, J=7.6 Hz, 2H), 1.57-1.43 (m, 4H), 1.27 (t, J=7.6 Hz, 3H), 1.00-0.94 (m, 3H).

Physical properties of compound (1-2-30) were as described below. In addition, for measurement of maximum temperature, optical anisotropy, dielectric anisotropy and viscosity, a sample in which a ratio of the compound to the base liquid crystal was 10% by weight: 90% by weight was used.

Transition temperature: C 119.3 I.

Maximum temperature (T$_{NI}$)=109° C.; optical anisotropy (Δn)=0.157; dielectric anisotropy (Δ∈)=−4.87; and viscosity (η)=97.5 mPa·s.

Example 5

Synthesis of Compound (1-2-31)

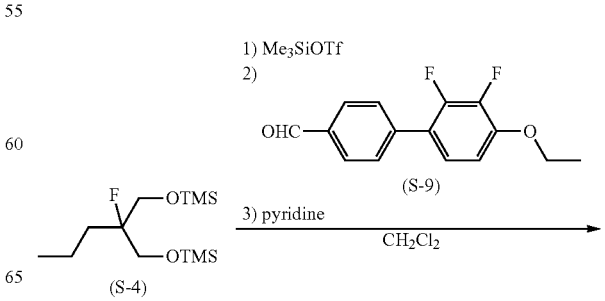

83

-continued

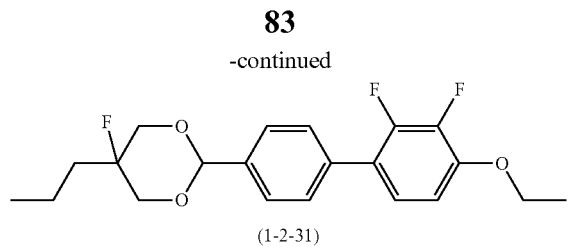

(1-2-31)

First Step

Under a nitrogen atmosphere, compound (S-4) (2.12 g), trimethylsilyl trifluoromethanesulfonate (0.12 mL) and dichloromethane (15 mL) were put in a reaction vessel, and the resulting mixture was cooled to −70° C. A dichloromethane (5 mL) solution of compound (S-9) (2.26 g) prepared according to a publicly known method was slowly added thereto, and the resulting mixture was stirred for 2 hours. Pyridine (0.79 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (heptane:toluene=1:2 in a volume ratio). The residue was further purified by recrystallization from a mixed solvent of heptane and ethyl acetate (1:1 in a volume ratio) to give compound (1-2-31) having fluorine atom in axial position (1.06 g; 37%).

Chemical shifts δ (ppm; CDCl$_3$): 7.59 (d, J=8.3, 2H), 7.51 (dd, J=8.2, J=1.5, 2H), 7.08 (dt, J=8.5, J=2.5, 1H), 6.81-6.75 (m, 1H), 5.52 (s, 1H), 4.26 (dd, J=12.3, 2H), 4.16 (q, J=7.0 Hz, 2H), 3.95-3.83 (m, 2H), 1.56-1.44 (m, 7H), 0.99-0.94 (m, 3H).

Physical properties of compound (1-2-31) were as described below. In addition, for measurement of maximum temperature, optical anisotropy, dielectric anisotropy and viscosity, a sample in which a ratio of the compound to the base liquid crystal was 5% by weight: 95% by weight was used.

Transition temperature: C 130 N 167 I.

Maximum temperature ($T_{NI}$)=163° C.; optical anisotropy (Δn)=0.207; dielectric anisotropy (Δ∈)=−6.25; and viscosity (η)=95.6 mPa·s.

Example 6

Synthesis of Compound (1-1-15)

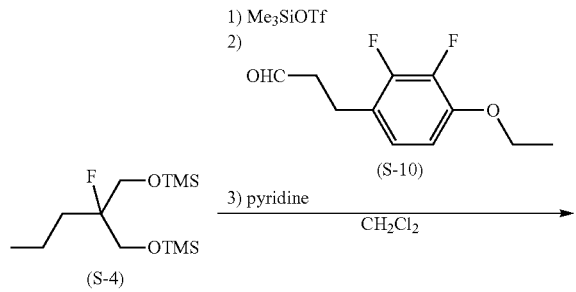

84

-continued

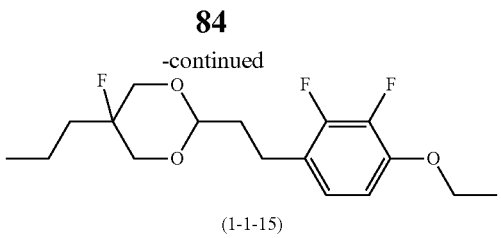

(1-1-15)

First Step

Under a nitrogen atmosphere, compound (S-4) (7.57 g), trimethylsilyl trifluoromethanesulfonate (3.56 mL) and dichloromethane (50 mL) were put in a reaction vessel, and the resulting mixture was cooled to −70° C. A dichloromethane (10 mL) solution of compound (S-10) (4.44 g) prepared according to a publicly known method was slowly added thereto, and the resulting mixture was stirred for 2 hours. Pyridine (2.07 mL) was added thereto. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (heptane:ethyl acetate=5:1 in a volume ratio). The residue was further purified by recrystallization from heptane to give compound (1-1-15) having fluorine atom in axial position (0.31 g; 4.7%).

Chemical shifts δ (ppm; CDCl$_3$): 6.82 (dt, J=8.5, J=2.0, 1H), 6.67-6.62 (m, 1H), 4.46 (t, J=5.3, 1H), 4.13-4.04 (m, 4H), 3.63 (dd, J=35.4, J=12.6, 2H), 2.73 (t, J=7.4, 2H), 1.99-1.93 (m, 2H), 1.45-1.36 (m, 7H), 0.93 (t, J=6.7, 3H).

Physical properties of compound (1-1-15) were as described below. In addition, for measurement of maximum temperature, optical anisotropy and dielectric anisotropy, a sample in which a ratio of the compound to the base liquid crystal was 10% by weight: 90% by weight was used.

Transition temperature: C 74.5 (SA 45.8) I.

Maximum temperature ($T_{NI}$)=−20.4° C.; optical anisotropy (611)=0.077; and dielectric anisotropy (Δ∈)=−5.45.

Example 7

Synthesis of Compound (1-2-182)

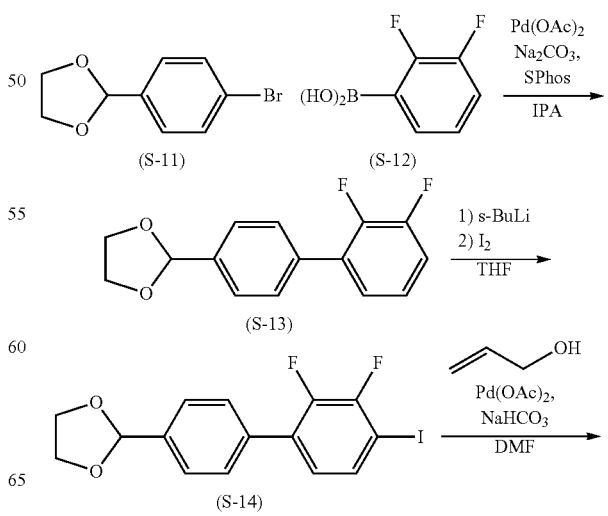

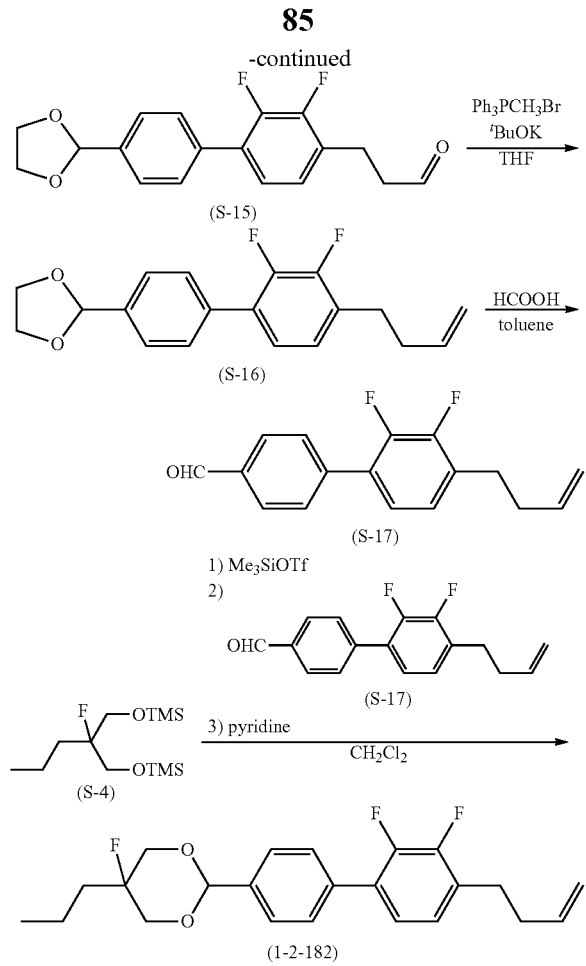

First Step

Under a nitrogen atmosphere, compound (S-11) (8.00 g), compound (S-12) (8.27 g), sodium carbonate (7.40 g), palladium acetate (7.84 mg), an SPhos ligand (28.7 mg) and 2-propanol (80 mL) were put in a reaction vessel, and the resulting mixture was stirred, and heated under refluxing for 9 hours. The resulting reaction mixture was poured into water, and an aqueous layer was subjected to extraction with toluene. Organic layers combined were washed with water and saturated brine, and then dried over anhydrous magnesium sulfate. The resulting solution was concentrated under reduced pressure, and the residue was purified by silica gel column chromatography (heptane:ethyl acetate=4:1 in a volume ratio). The residue was further purified by recrystallization from Solmix to give compound (S-13) (7.49 g; 820).

Second Step

Under a nitrogen atmosphere, compound (S-13) (3.17 g) and THF (25 mL) were put in a reaction vessel, and the resulting mixture was cooled to −70° C. Then, s-butyllithium (1.08 M cyclohexane solution, 13.4 mL) was slowly added thereto, and the resulting mixture was stirred for 1 hour, and then a THF (7 mL) solution of iodine (3.83 g) was slowly added thereto, and then the resulting mixture was heated to room temperature. The resulting reaction mixture was poured into water, and an aqueous layer was subjected to extraction with ethyl acetate. Organic layers combined were washed with an aqueous solution of sodium sulfite, water and saturated brine, and dried over anhydrous magnesium sulfate. The resulting solution was concentrated under reduced pressure, and the residue was purified by silica gel column chromatography (toluene) to give compound (S-14) (3.79 g; 81%).

Third Step

Under a nitrogen atmosphere, compound (S-14) (4.82 g), allyl alcohol (1.69 mL), tetrabutylammonium chloride (3.80 g), palladium acetate (55.8 mg), sodium hydrogencarbonate (3.13 g) and N,N'-dimethylformamide (50 mL) were put in a reaction vessel, and the resulting mixture was heated to 40° C. and stirred for 3 hours. The resulting reaction mixture was poured into water, and an aqueous layer was subjected to extraction with toluene. Organic layers combined were washed with water and saturated brine, and then dried over anhydrous magnesium sulfate. The resulting solution was concentrated under reduced pressure, and the residue was purified by silica gel column chromatography (heptane:ethyl acetate=2:1 in a volume ratio) to give compound (S-15) (3.43 g; 87%).

Fourth Step

Under a nitrogen atmosphere, ethyltriphenylphosphonium bromide (5.20 g) and THF (20 mL) were put in a reaction vessel, and the resulting mixture was cooled to −20° C. Potassium t-butoxide (1.57 g) was added little by little thereto, and the resulting mixture was stirred for 1 hour, and then a THF (20 mL) solution of compound (S-15) (3.71 g) was slowly added thereto, and the resulting mixture was heated to room temperature. The resulting reaction mixture was poured into water, and an aqueous layer was subjected to extraction with toluene. Organic layers combined were washed with water and saturated brine, and then dried over anhydrous magnesium sulfate. The resulting solution was concentrated under reduced pressure, and the residue was purified by silica gel column chromatography (eluate: toluene) to give compound (S-16) (3.05 g; 83%).

Fifth Step

Under a nitrogen atmosphere, compound (S-16) (3.05 g), formic acid (0.93 mL) and toluene (8 mL) were put in a reaction vessel, and the resulting mixture was stirred, and heated under refluxing for 8 hours. The resulting reaction mixture was poured into water, and an aqueous layer was subjected to extraction with toluene. Organic layers combined were washed with water and saturated brine, and then dried over anhydrous magnesium sulfate. The resulting solution was concentrated under reduced pressure, and the residue was purified by silica gel column chromatography (heptane: ethyl acetate=10:1 in a volume ratio) to give compound (S-17) (2.16 g; 82%).

Sixth Step

Under a nitrogen atmosphere, compound (S-4) (5.16 g), trimethylsilyl trifluoromethanesulfonate (1.55 mL) and dichloromethane (10 mL) were put in a reaction vessel, and the resulting mixture was cooled to −70° C. A dichloromethane (10 mL) solution of compound (S-17) (1.67 g) was slowly added thereto, and the resulting mixture was stirred for 2 hours. Pyridine (2.07 mL) was added thereto. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (toluene). The residue was further purified by recrystallization from a mixed solvent of heptane and THF (1:1 in a volume ratio) to give compound (1-2-182) having fluorine atom in axial position (0.70 g; 29%).

Chemical shifts δ (ppm; CDCl₃): 7.61 (d, J=8.3, 2H), 7.56-7.53 (m, 2H), 7.11-7.07 (m, 1H), 7.00-6.96 (m, 1H), 5.91-5.82 (m, 1H), 5.53 (s, 1H), 5.09-5.00 (m, 2H), 4.26 (t, J=12.0, 2H), 3.89 (dd, J=34.9, J=12.7, 2H), 2.79 (t, J=7.6, 2H), 2.43-2.37 (m, 2H), 1.56-1.43 (m, 4H), 0.99-0.95 (m, 3H)

Physical properties of compound (1-2-182) were as described below. In addition, for measurement of maximum temperature, optical anisotropy and dielectric anisotropy, a sample in which a ratio of the compound to the base liquid crystal was 5% by weight: 95% by weight was used.

Transition temperature: C 127 (N 120) I.

Maximum temperature (T$_{NI}$)=122° C.; optical anisotropy (Δn)=0.187; and dielectric anisotropy (Δε)=−3.21.

Compounds (1-1-1) to (1-1-50), compounds (1-2-1) to (1-2-211) and compounds (1-3-1) to (1-3-109) described below can be prepared according to the method for preparing compound (1) described above and preparation procedures described in Examples 1 to 5.

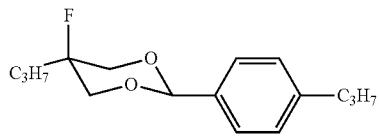
(1-1-1)
C 82.7 I
T$_{NI}$ = -7.4° C., Δε = -3.98, Δn = 0.0657

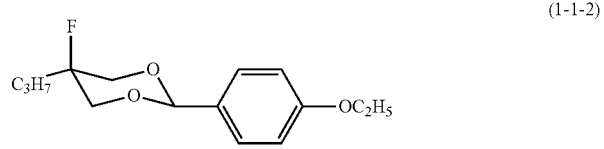
(1-1-2)

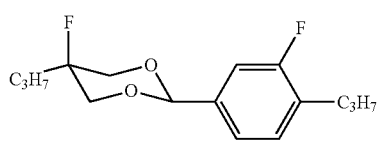
(1-1-3)

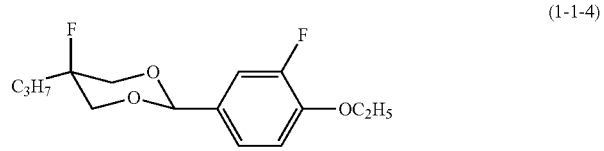
(1-1-4)
C 107 I
T$_{NI}$ = -24.6° C., Δε = -4.84, Δn = 0.107

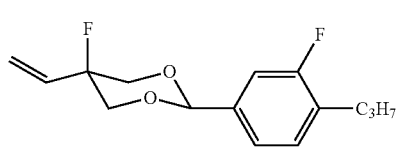
(1-1-5)

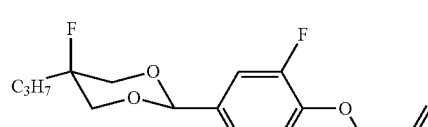
(1-1-6)

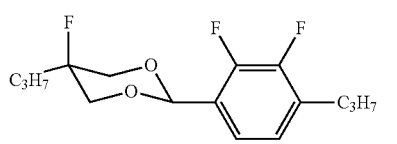
(1-1-7)

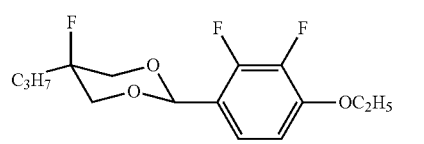
(1-1-8)

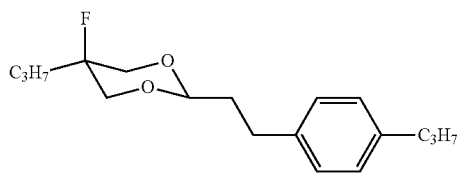
(1-1-9)

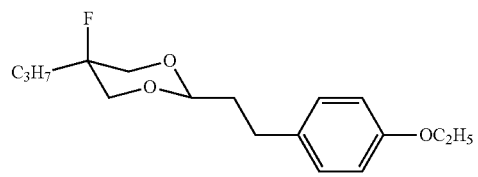
(1-1-10)

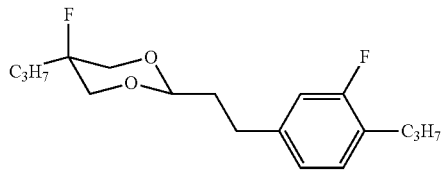
(1-1-11)

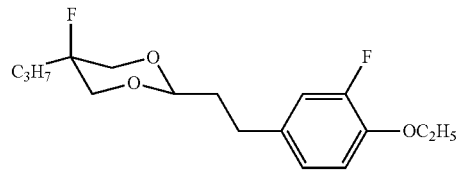
(1-1-12)

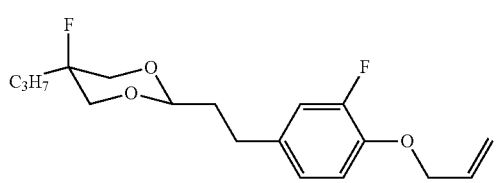
(1-1-13)

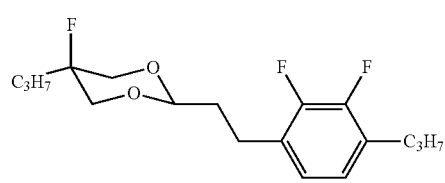
(1-1-14)

-continued
(1-1-15)
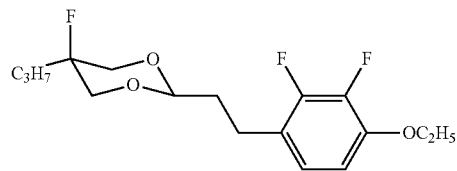
C 74.5 (S$_A$ 45.8) I
T$_{NI}$ = -20.4° C., Δε = -5.45, Δn = 0.077
(1-1-16)
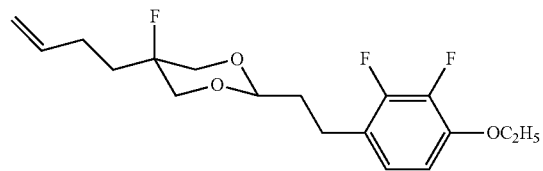
(1-1-17)
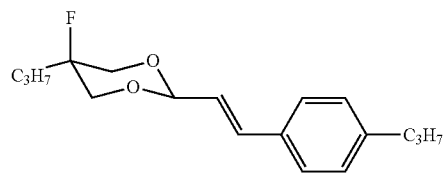
(1-1-18)
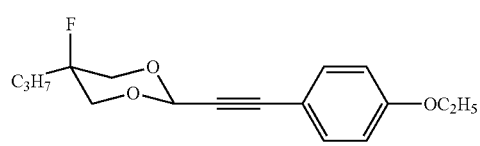
(1-1-19)
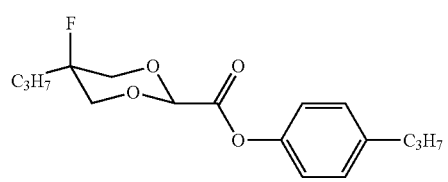
(1-1-20)
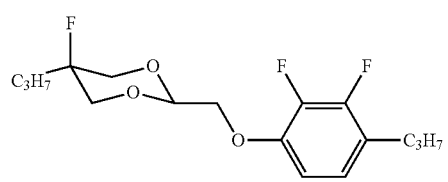
(1-1-21)
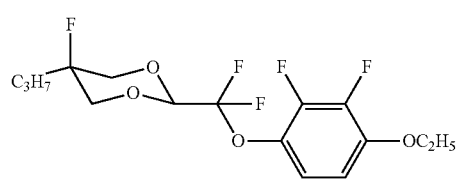
(1-1-22)
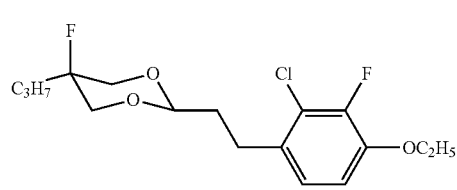
(1-1-23)
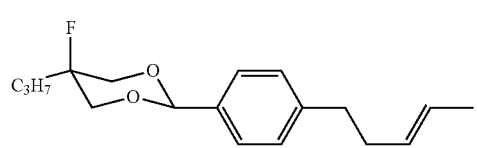
(1-1-24)
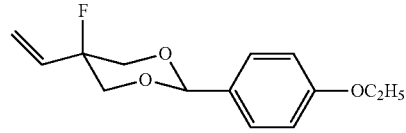
(1-1-25)
(1-1-26)
(1-1-27)
(1-1-28)
(1-1-29)
(1-1-30)

-continued
(1-1-31) 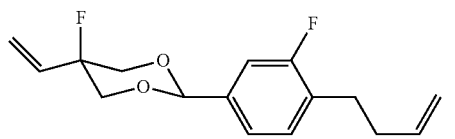
(1-1-32) 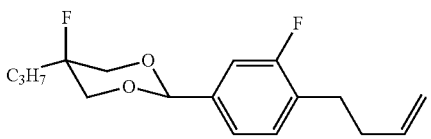
(1-1-33) 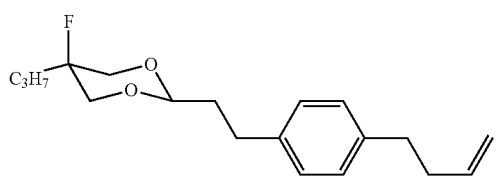
(1-1-34) 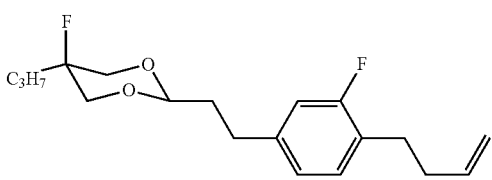
(1-1-35) 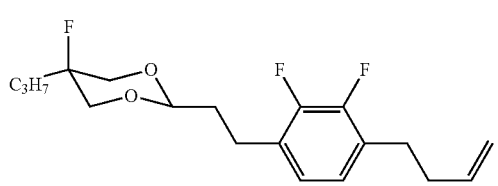
(1-1-36) 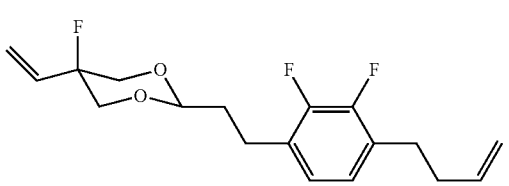
(1-1-37) 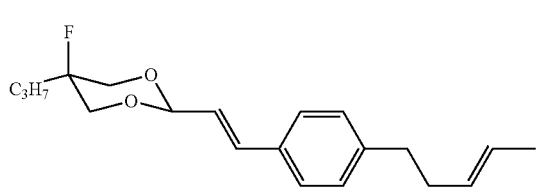
(1-1-38) 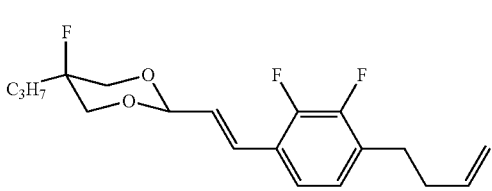
(1-1-39) 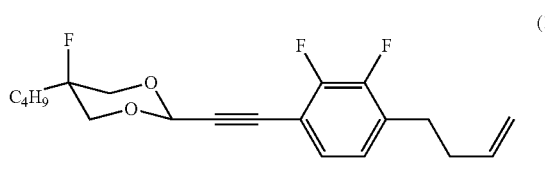
(1-1-40) 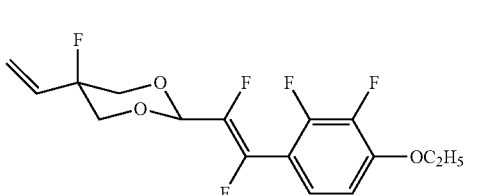
(1-1-41) 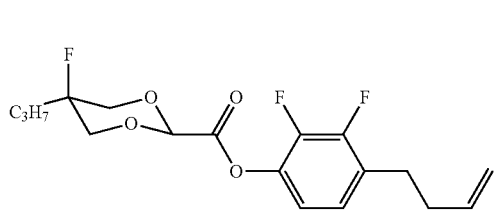
(1-1-42) 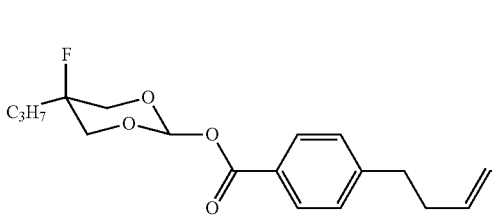
(1-1-43) 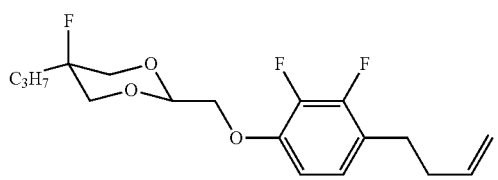
(1-1-44) 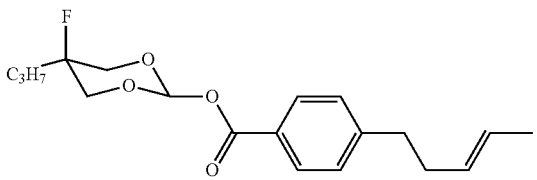
(1-1-45) 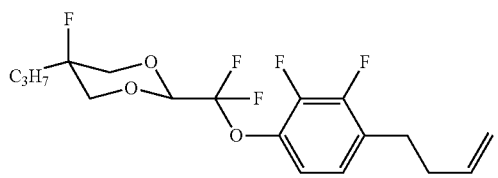
(1-1-46) 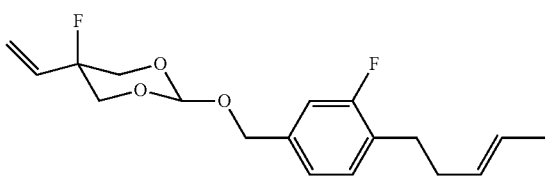

-continued
(1-1-47)
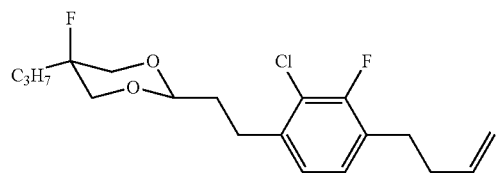
(1-1-48)
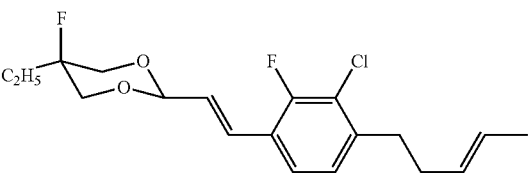
(1-1-49)
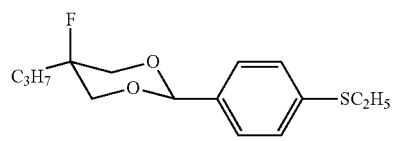
(1-1-50)
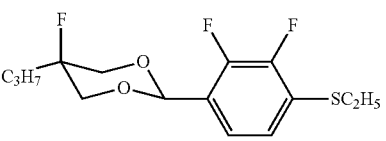
(1-2-1)
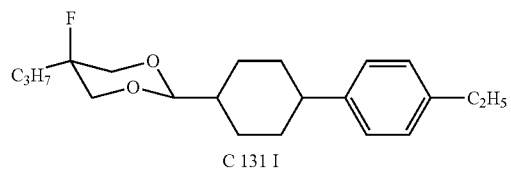
C 131 I
$T_{NI}$ = 97.6° C., Δε = -3.05, Δn = 0.100
(1-2-2)
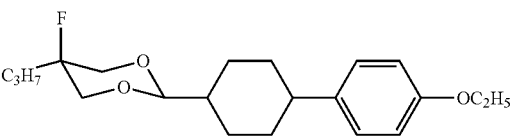
(1-2-3)
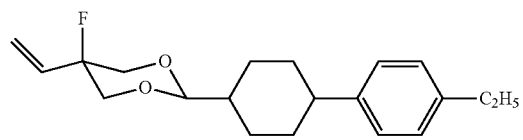
(1-2-4)
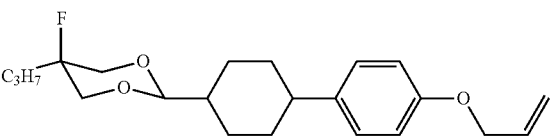
(1-2-5)
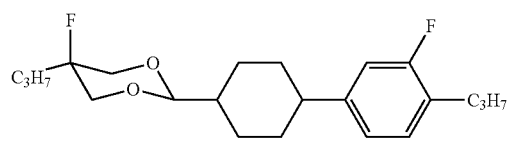
(1-2-6)
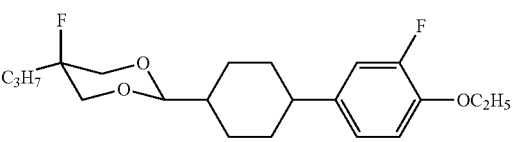
(1-2-7)
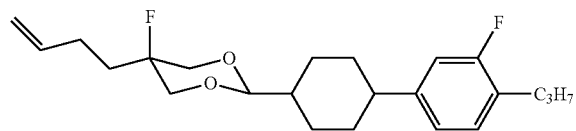
(1-2-8)
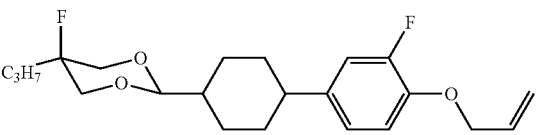
(1-2-9)
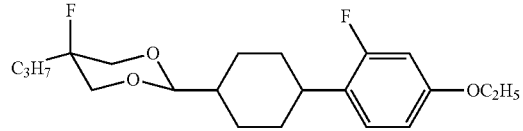
(1-2-10)
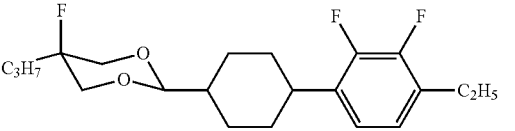
(1-2-11)
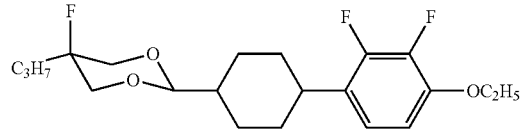
(1-2-12)
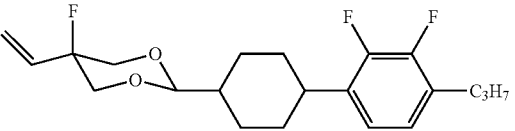
(1-2-13)
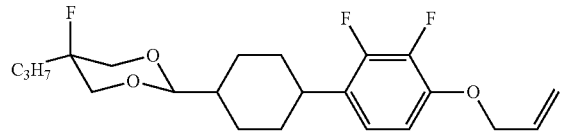
(1-2-14)
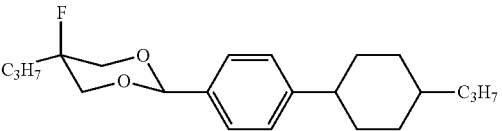

-continued
(1-2-15)
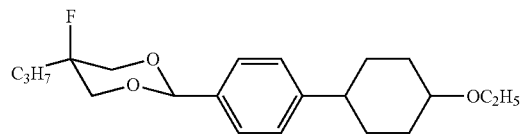
(1-2-16)
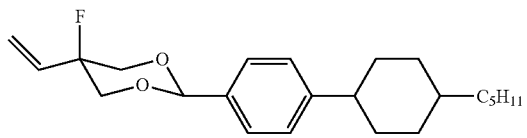
(1-2-17)
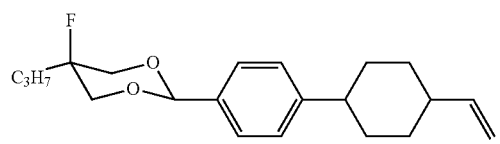
(1-2-18)
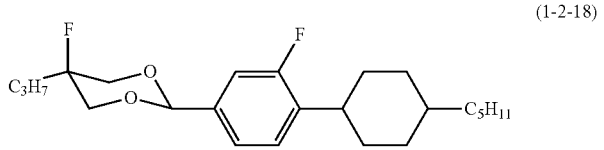
(1-2-19)
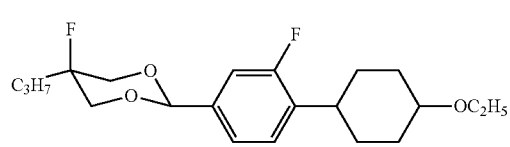
(1-2-20)
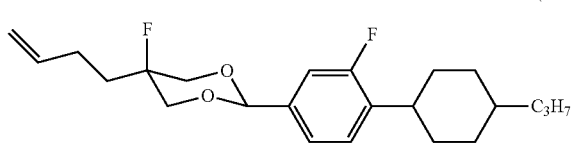
(1-2-21)
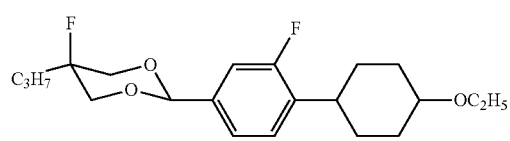
(1-2-22)
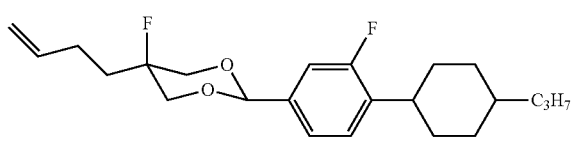
(1-2-23)
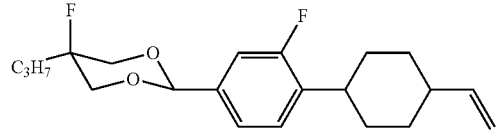
(1-2-24)
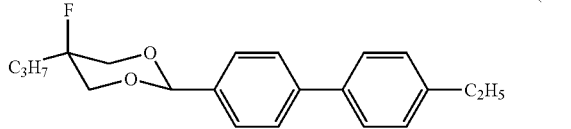
(1-2-25)
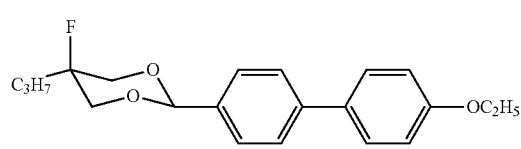
(1-2-26)
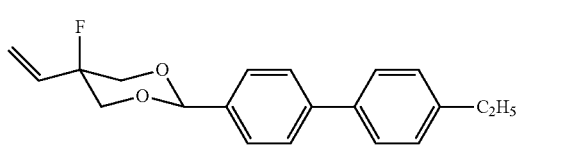
(1-2-27)
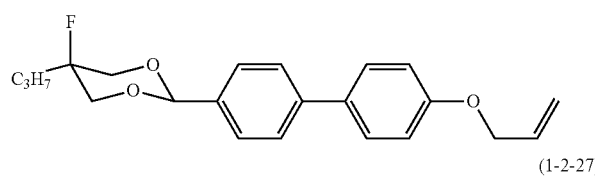
(1-2-28)
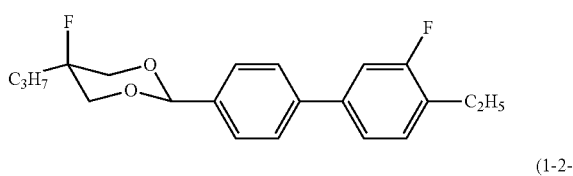
(1-2-29)
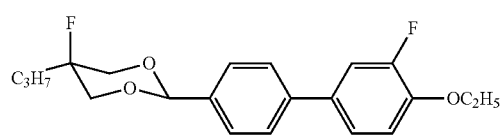
(1-2-30)
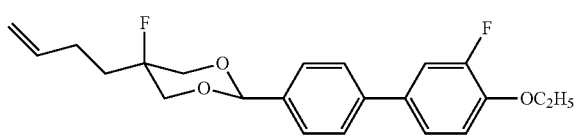
C 119 I
$T_{NI}$ = 109° C., Δε = −4.87, Δn = 0.157
(1-2-31)
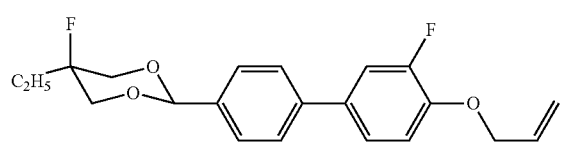
(1-2-32)
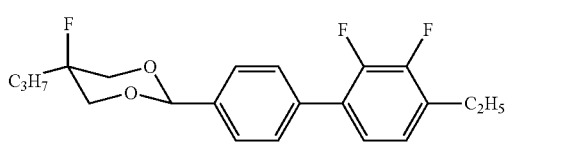
C 130 N 167 I
$T_{NI}$ = 163° C., Δε = −6.25, Δn = 0.207

-continued (1-2-33)
(1-2-34)
(1-2-35)
(1-2-36)
(1-2-37)
(1-2-38)
(1-2-39)
(1-2-40)
(1-2-41)
(1-2-42)
(1-2-43)
(1-2-44)
(1-2-45)
(1-2-46)
(1-2-47)
(1-2-48)
(1-2-49)
(1-2-50)

-continued
(1-2-51) 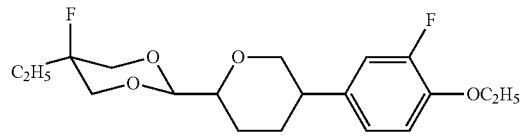
(1-2-52) 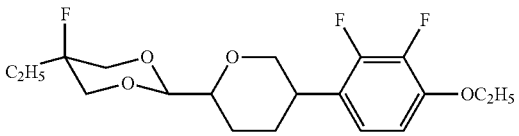
(1-2-53) 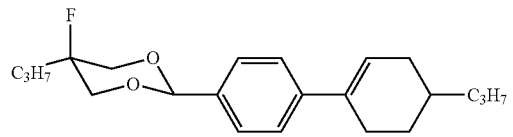
(1-2-54) 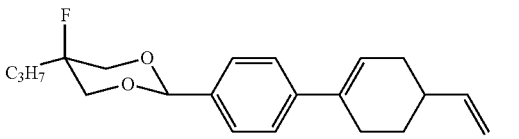
(1-2-55) 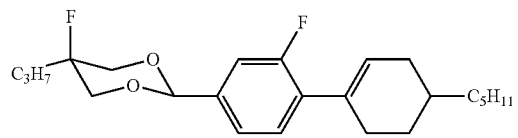
(1-2-56) 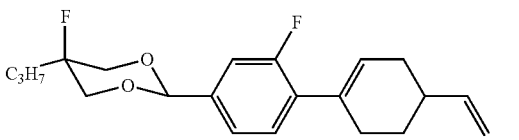
(1-2-57) 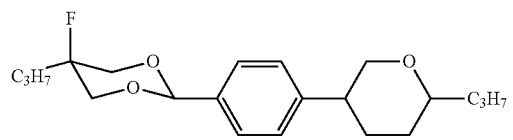
(1-2-58) 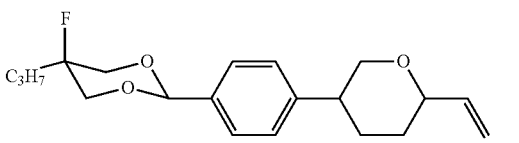
(1-2-59) 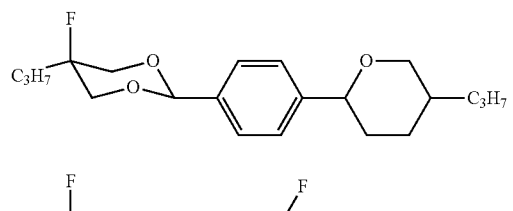
(1-2-60) 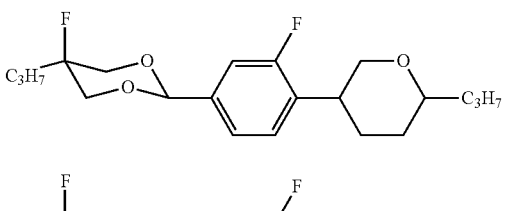
(1-2-61) 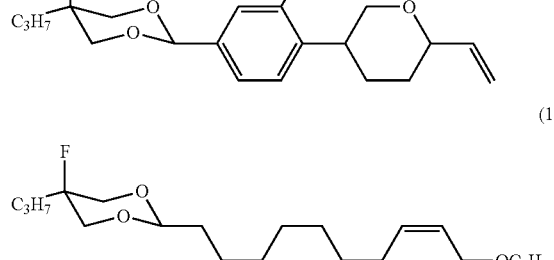
(1-2-62) 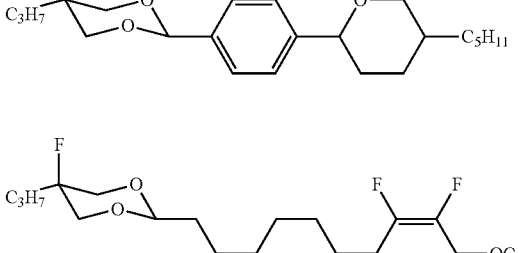
(1-2-63) 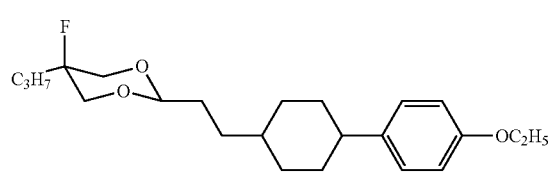
(1-2-64) 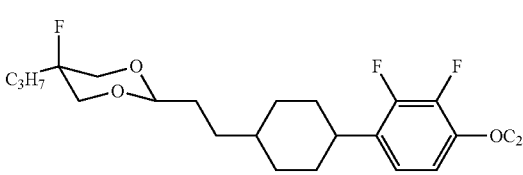
(1-2-65) 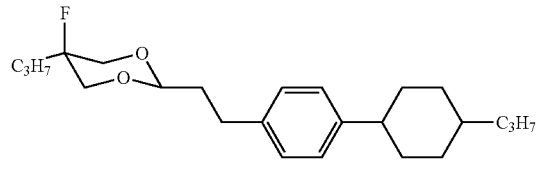
(1-2-66) 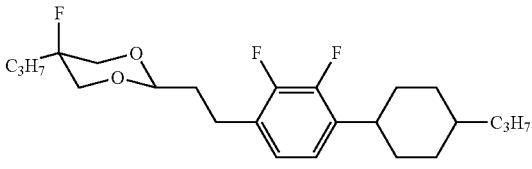
(1-2-67) 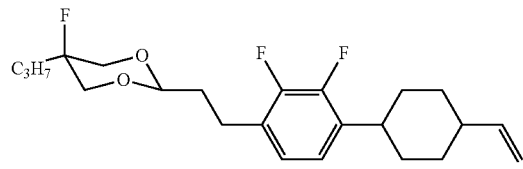
(1-2-68) 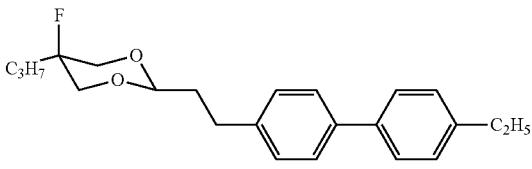

(1-2-69)
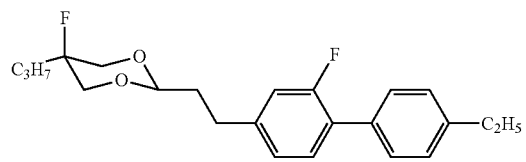
(1-2-70)
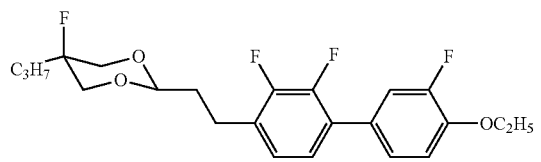
(1-2-71)
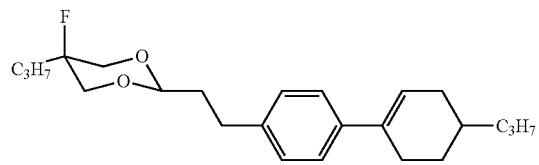
(1-2-72)
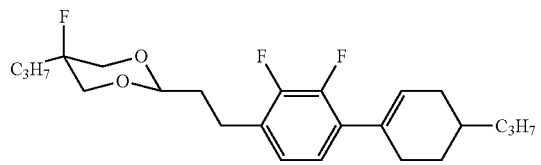
(1-2-73)
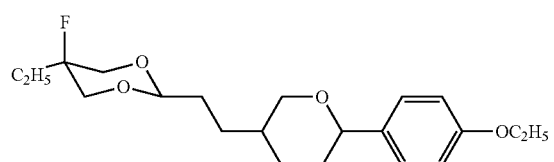
(1-2-74)
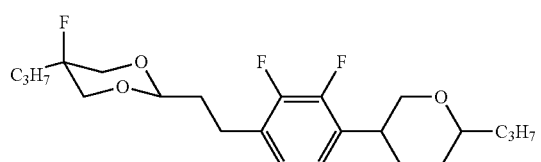
(1-2-75)
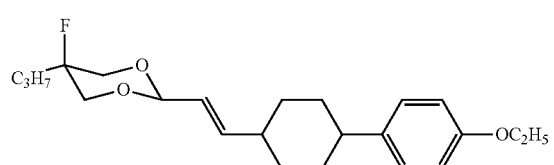
(1-2-76)
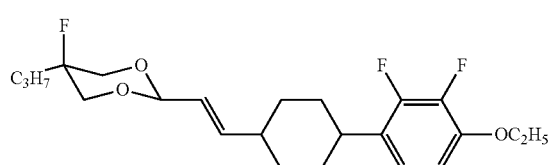
(1-2-77)
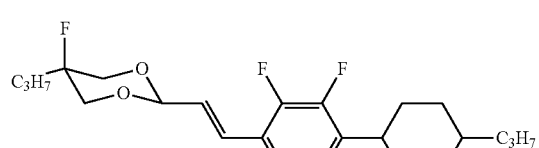
(1-2-78)
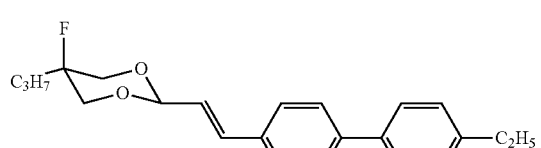
(1-2-79)
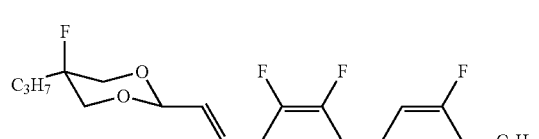
(1-2-80)
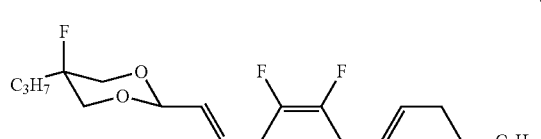
(1-2-81)
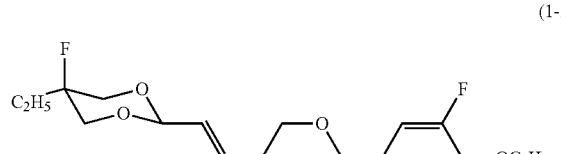
(1-2-82)
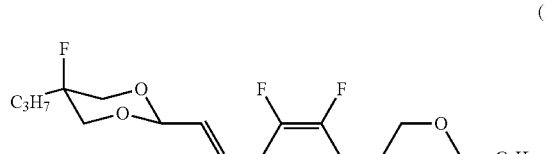
(1-2-83)
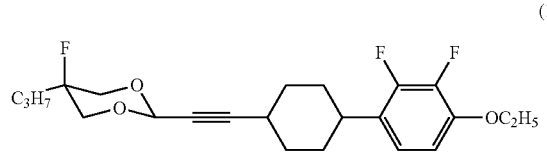
(1-2-84)
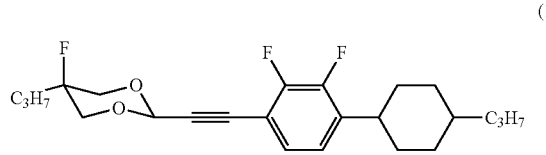
(1-2-85)
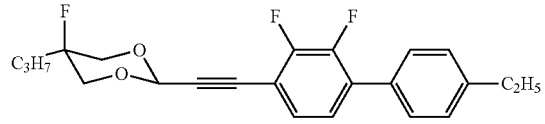
(1-2-86)
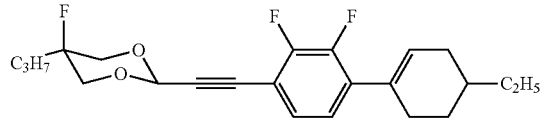

-continued
(1-2-87)
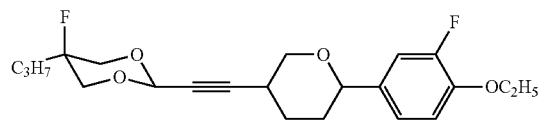
(1-2-88)
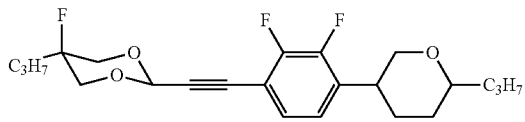
(1-2-89)
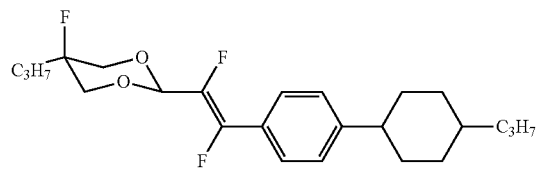
(1-2-90)
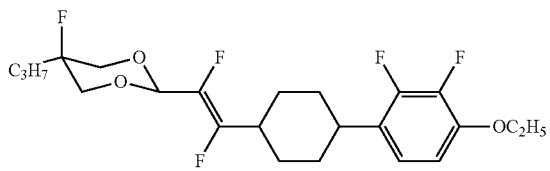
(1-2-91)
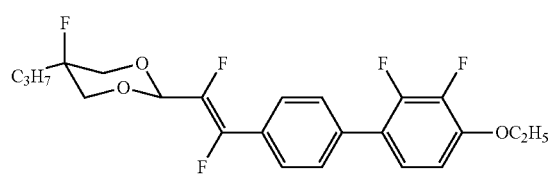
(1-2-92)
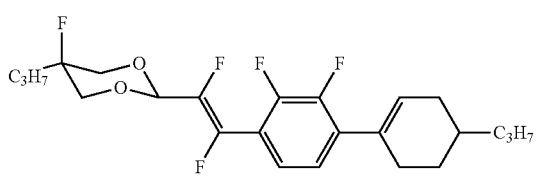
(1-2-93)
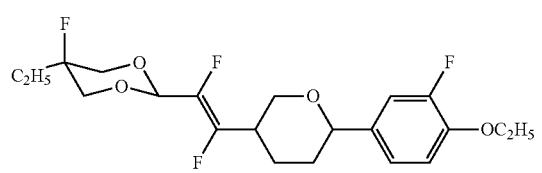
(1-2-94)
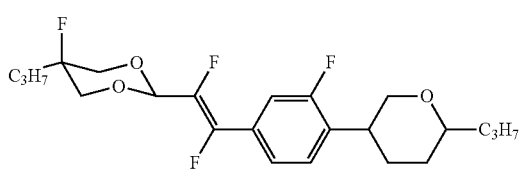
(1-2-95)
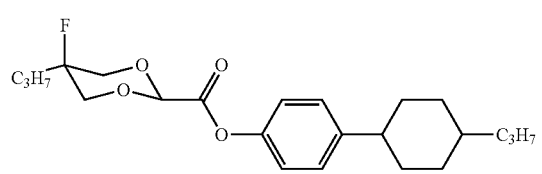
(1-2-96)
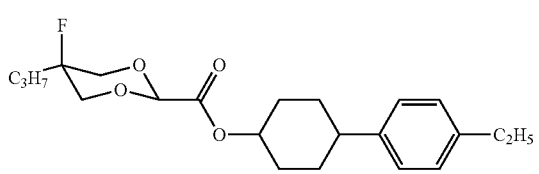
(1-2-97)
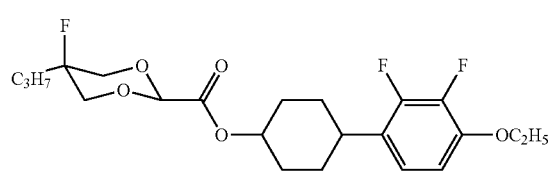
(1-2-98)
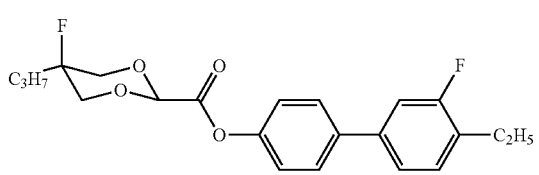
(1-2-99)
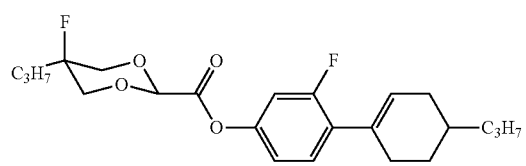
(1-2-100)
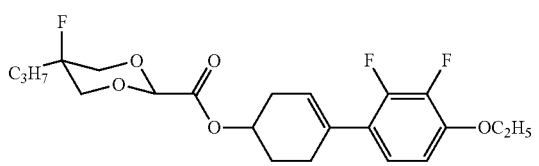
(1-2-101)
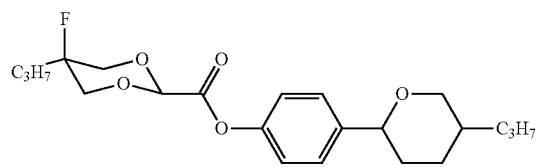
(1-2-102)
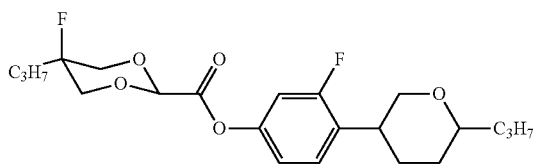

-continued
(1-2-103)
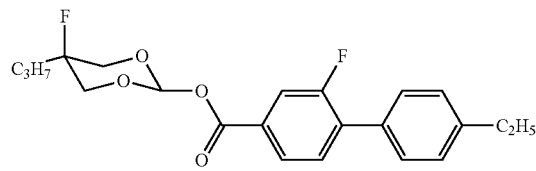
(1-2-104)
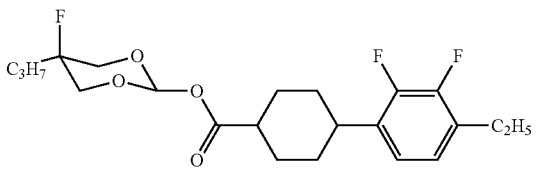
(1-2-105)
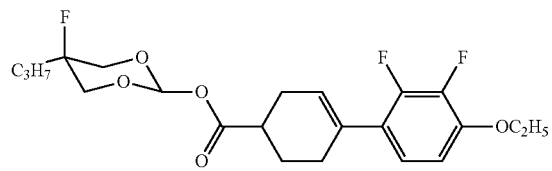
(1-2-106)
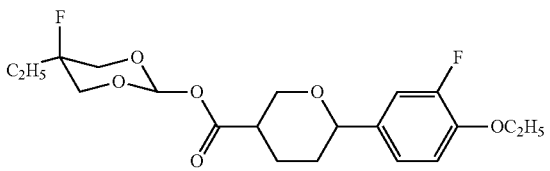
(1-2-107)
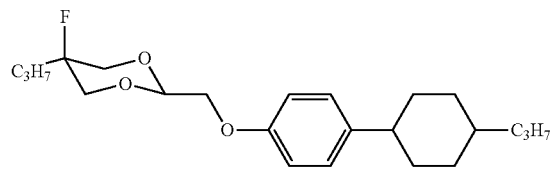
(1-2-108)
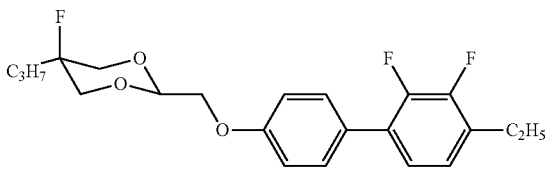
(1-2-109)
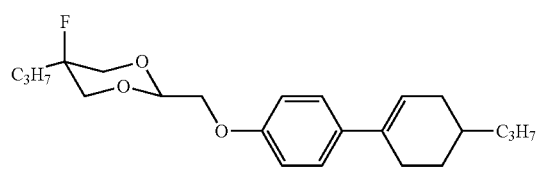
(1-2-110)
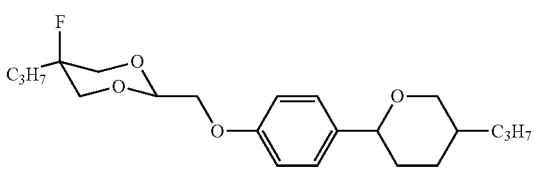
(1-2-111)
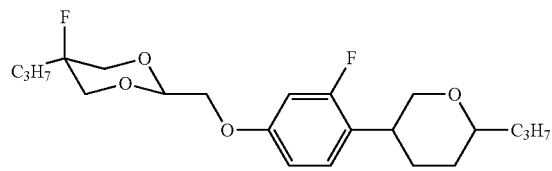
(1-2-112)
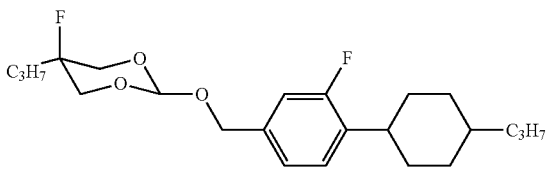
(1-2-113)
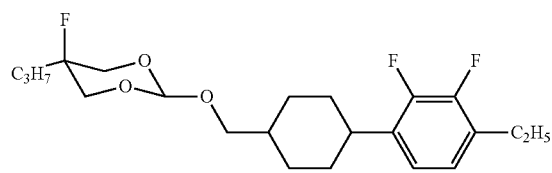
(1-2-114)
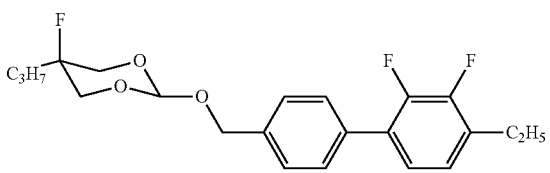
(1-2-115)
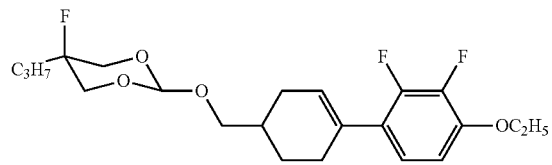
(1-2-116)
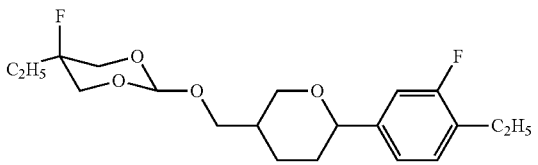
(1-2-117)
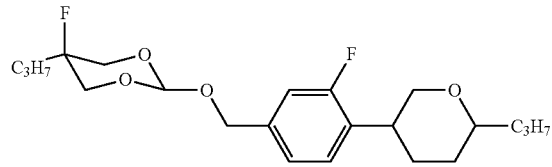
(1-2-118)
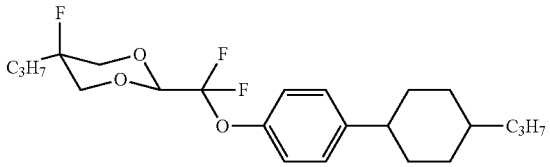

-continued
(1-2-119)
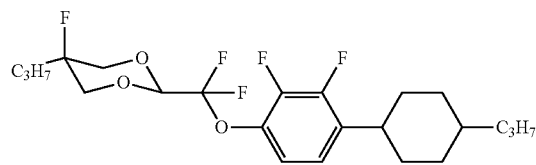
(1-2-120)
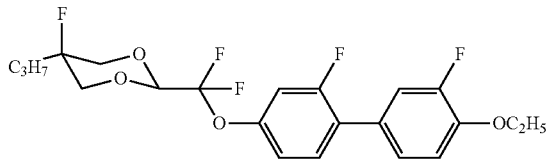
(1-2-121)
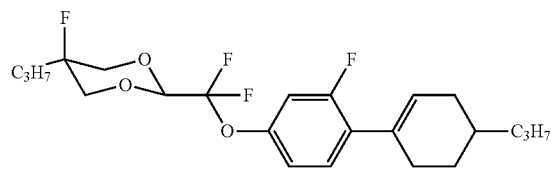
(1-2-122)
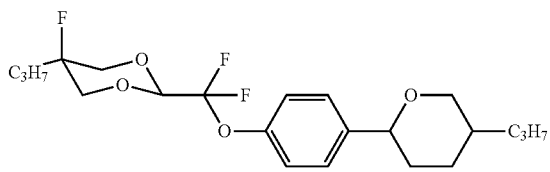
(1-2-123)
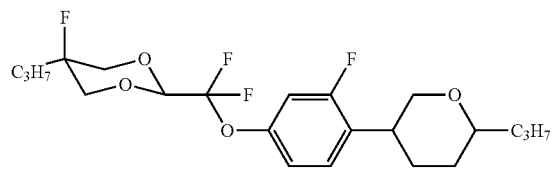
(1-2-124)
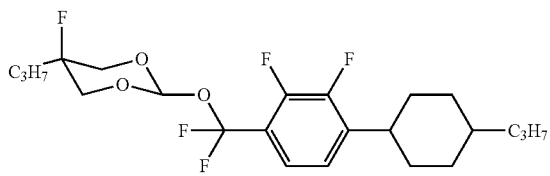
(1-2-125)
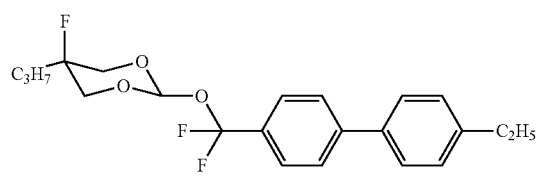
(1-2-126)
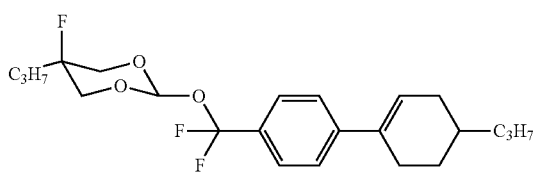
(1-2-127)
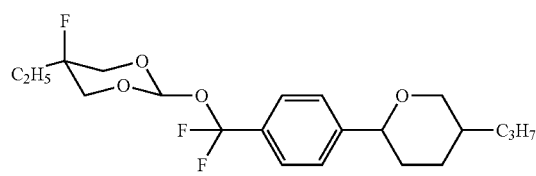
(1-2-128)
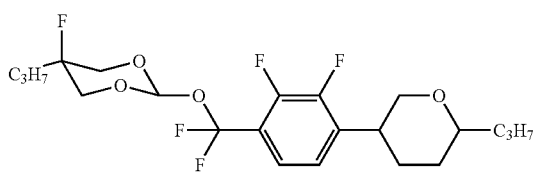
(1-2-129)
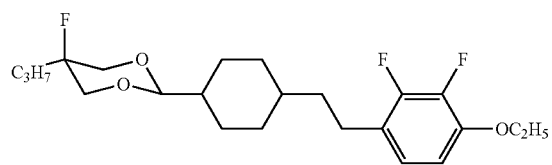
(1-2-130)
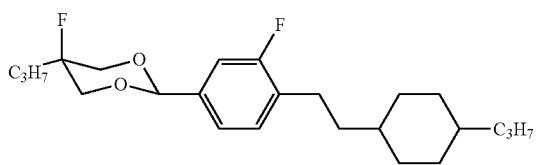
(1-2-131)
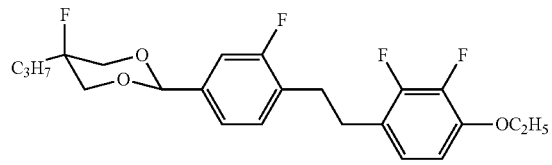
(1-2-132)
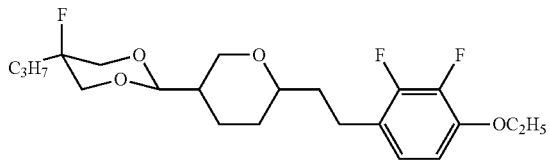
(1-2-133)
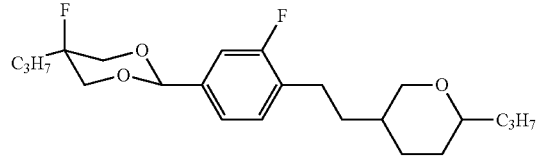
(1-2-134)
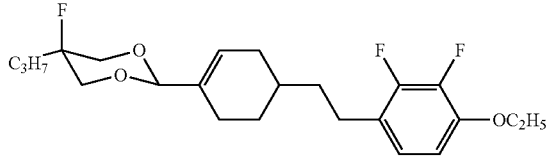

-continued
(1-2-135)
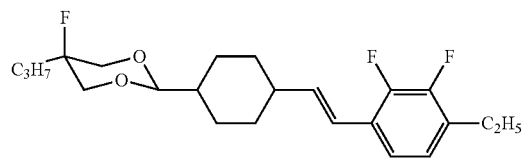
(1-2-136)
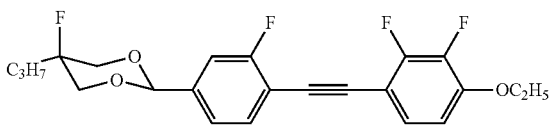
(1-2-137)
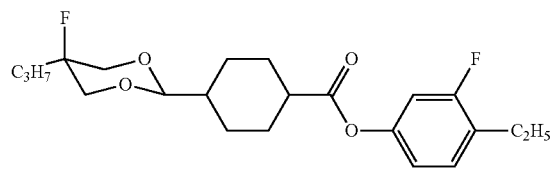
(1-2-138)
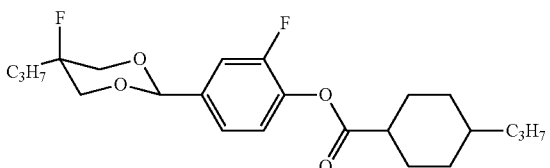
(1-2-139)
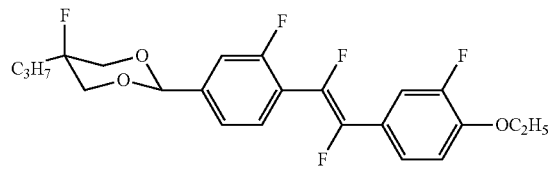
(1-2-140)
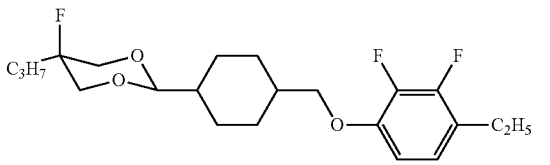
(1-2-141)
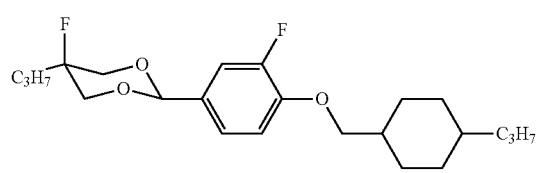
(1-2-142)
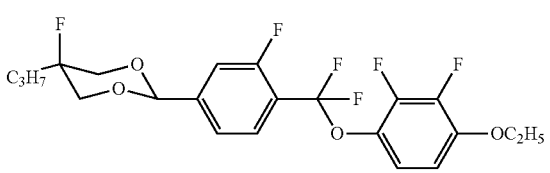
(1-2-143)
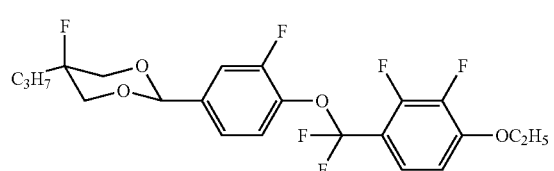
(1-2-144)
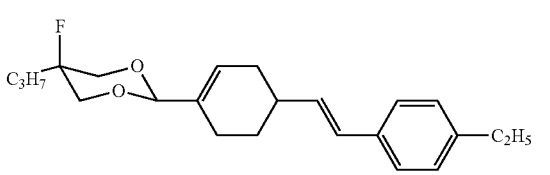
(1-2-145)
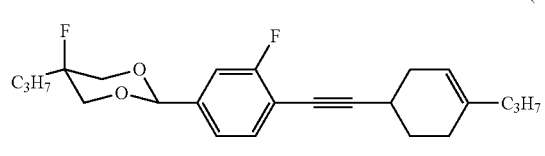
(1-2-146)
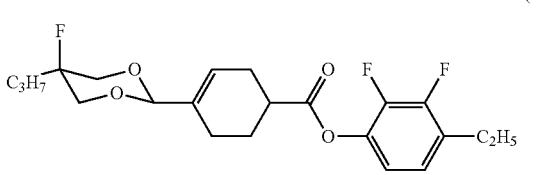
(1-2-147)
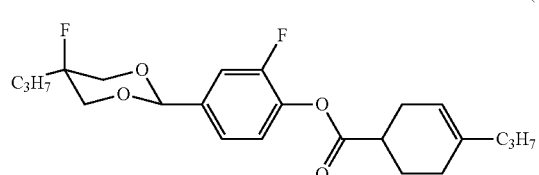
(1-2-148)
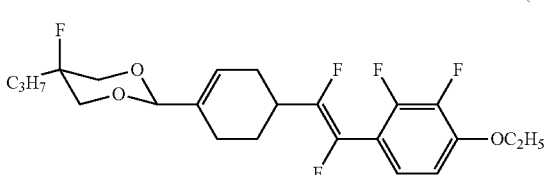
(1-2-149)
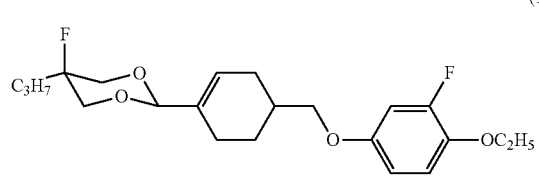
(1-2-150)
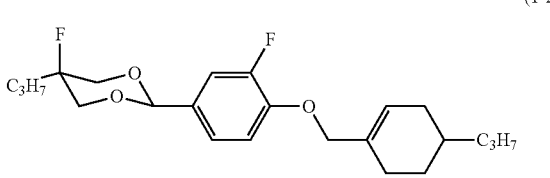

-continued
(1-2-151)
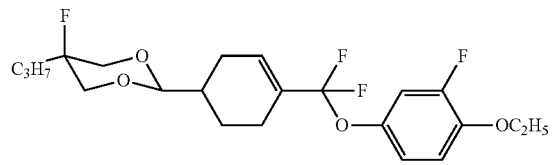
(1-2-152)
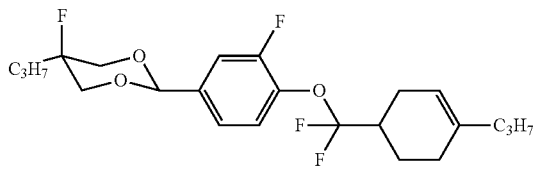
(1-2-153)
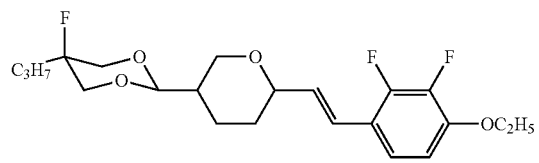
(1-2-154)
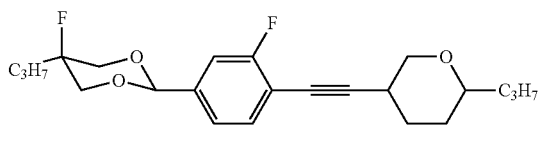
(1-2-155)
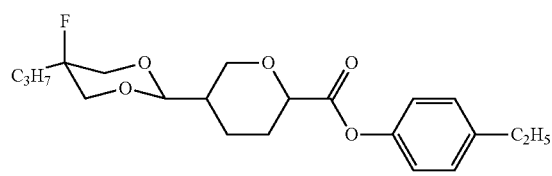
(1-2-156)
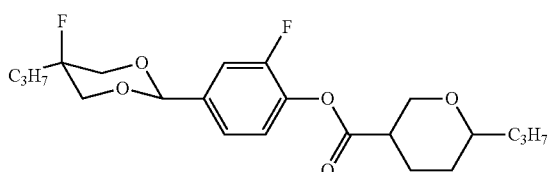
(1-2-157)
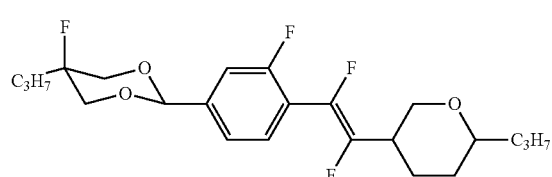
(1-2-158)
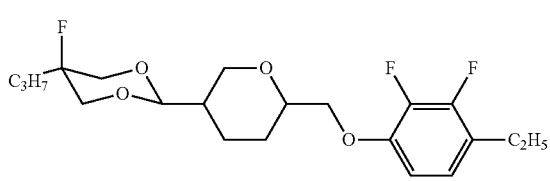
(1-2-159)
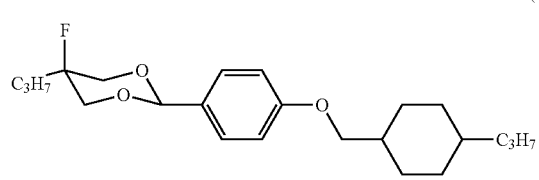
(1-2-160)
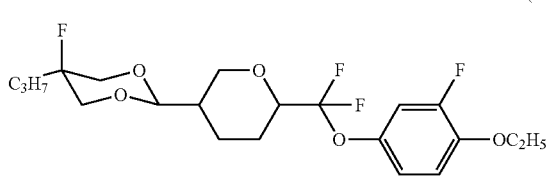
(1-2-161)
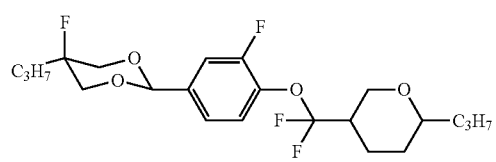
(1-2-162)
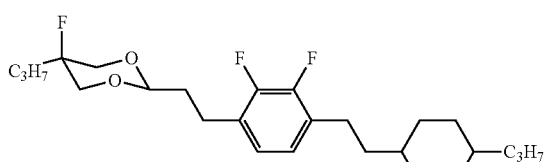
(1-2-163)
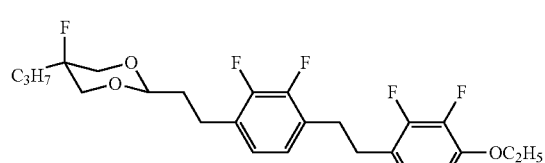
(1-2-164)
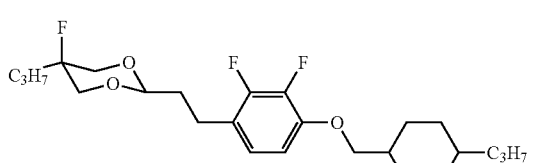
(1-2-165)
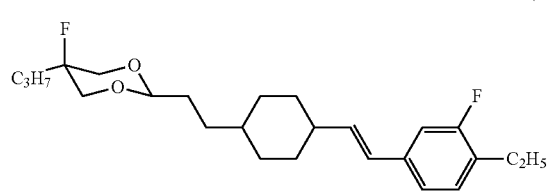
(1-2-166)
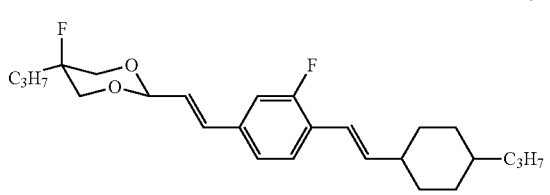

-continued
(1-2-167)
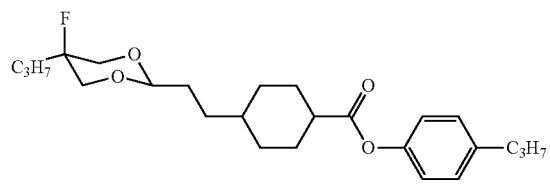
(1-2-168)
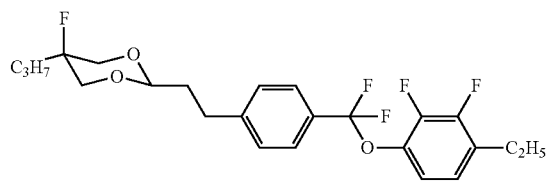
(1-2-169)
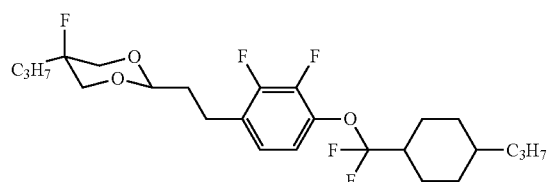
(1-2-170)
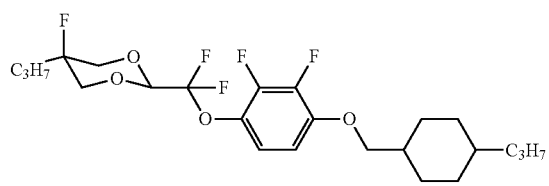
(1-2-171)
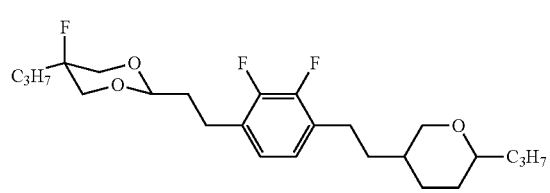
(1-2-172)
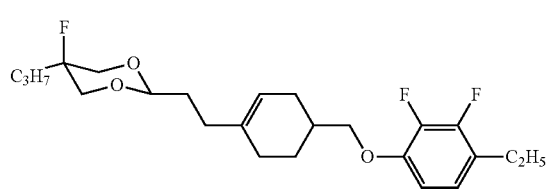
(1-2-173)
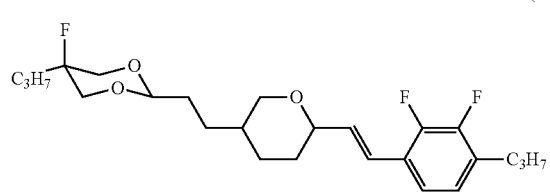
(1-2-174)
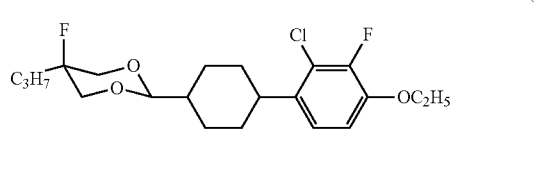
(1-2-175)
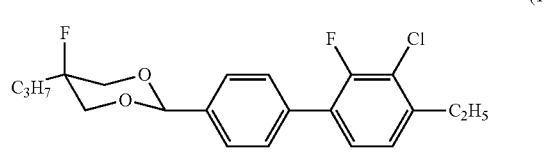
(1-2-176)
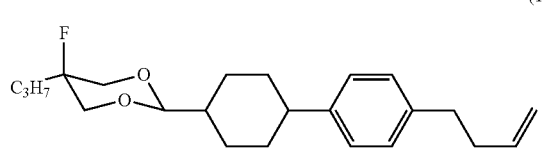
(1-2-177)
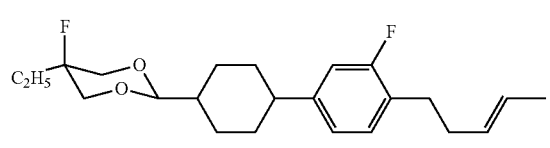
(1-2-178)
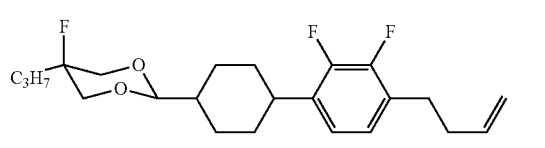
(1-2-179)
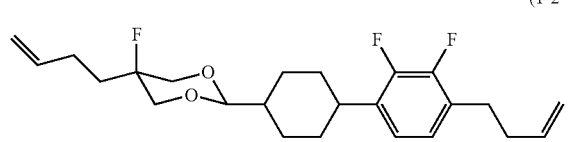
(1-2-180)
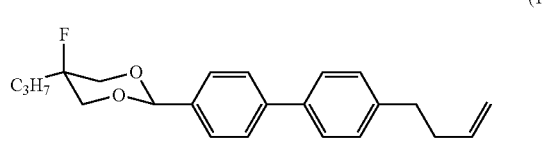
(1-2-181)
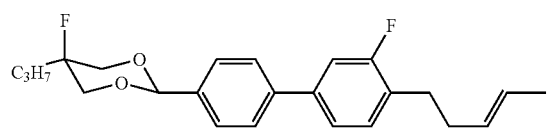
(1-2-182)
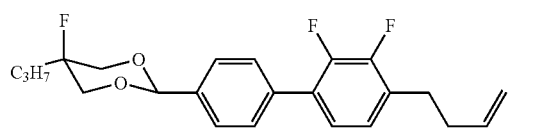
C 127 (N 120) I
$T_{NI}$ = 122° C., $\Delta\varepsilon$ = −3.21, $\Delta n$ = 0.187

-continued
(1-2-183)
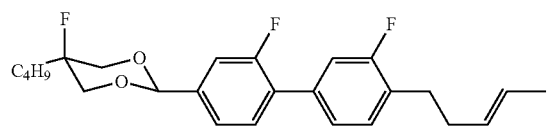
(1-2-184)
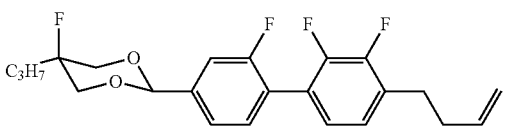
(1-2-185)
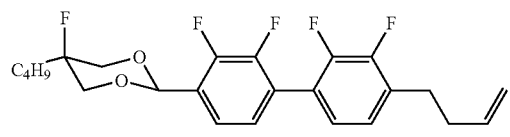
(1-2-186)
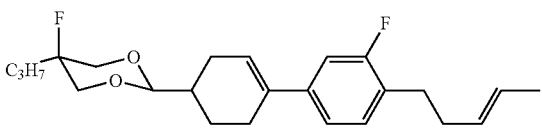
(1-2-187)
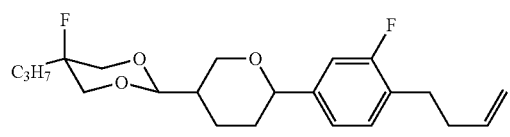
(1-2-188)
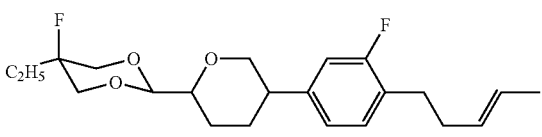
(1-2-189)
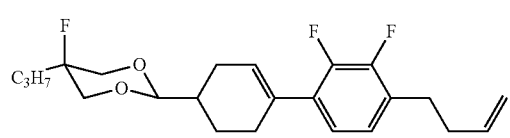
(1-2-190)
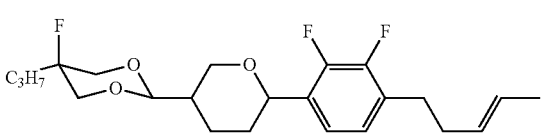
(1-2-191)
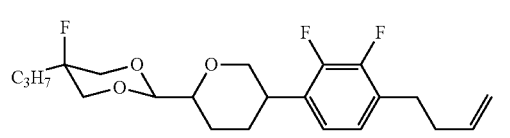
(1-2-192)
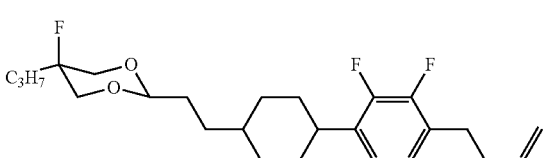
(1-2-193)
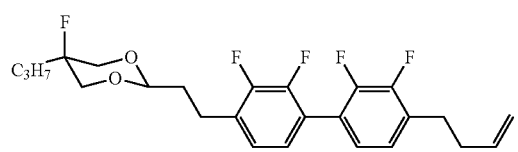
(1-2-194)
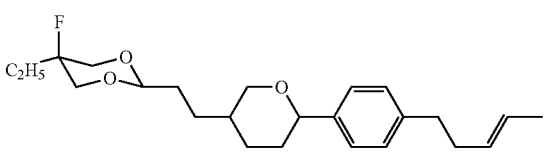
(1-2-195)
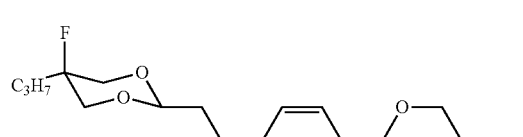
(1-2-196)
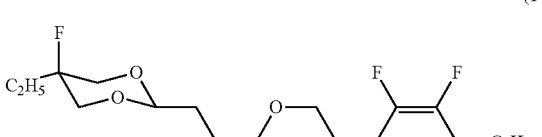
(1-2-197)
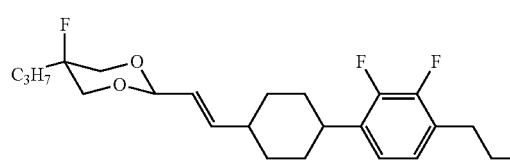
(1-2-198)
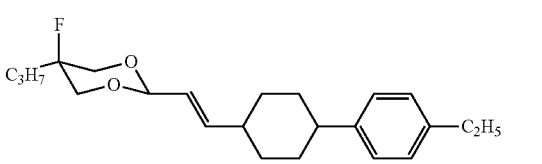
(1-2-199)
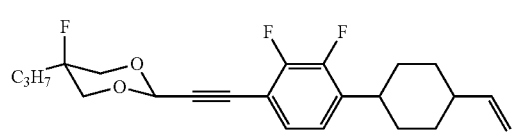
(1-2-200)
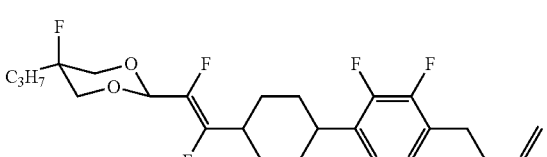

(1-2-201)
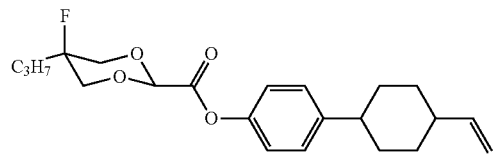
(1-2-202)
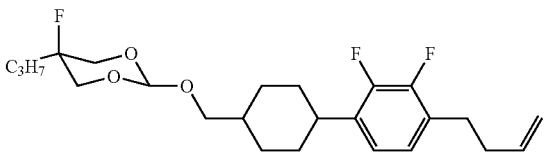
(1-2-203)
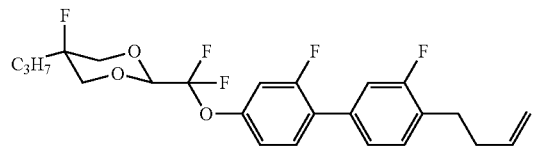
(1-2-204)
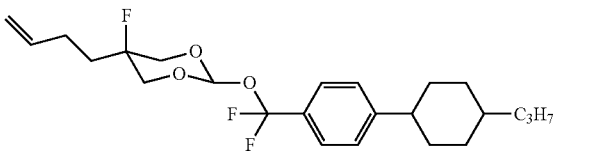
(1-2-205)
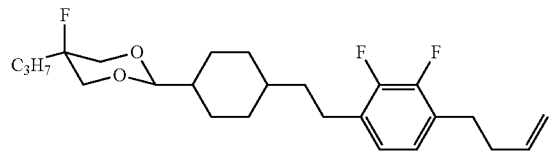
(1-2-206)
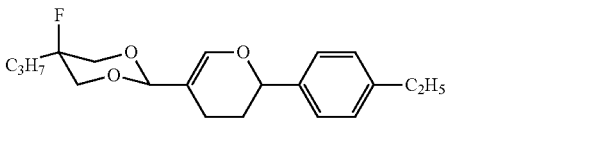
(1-2-207)
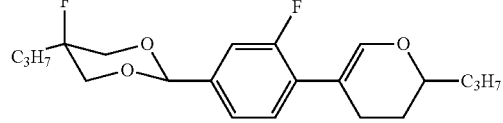
(1-2-208)
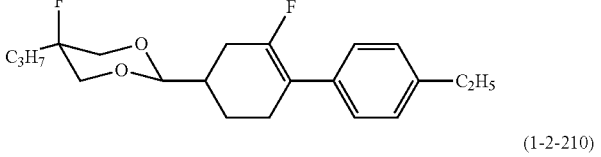
(1-2-209)
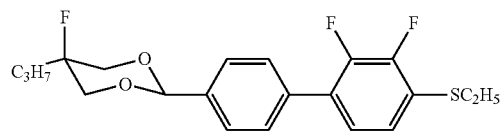
(1-2-210)
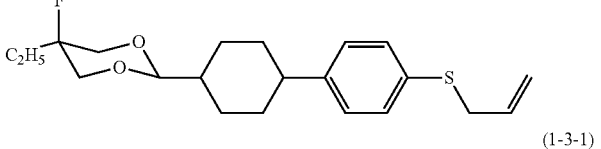
(1-2-211)
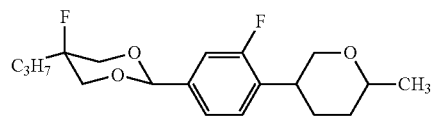
(1-3-1)
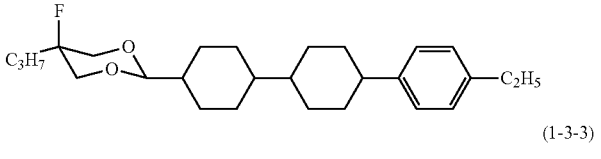
(1-3-2)
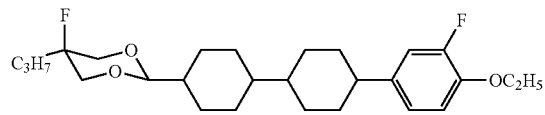
(1-3-3)
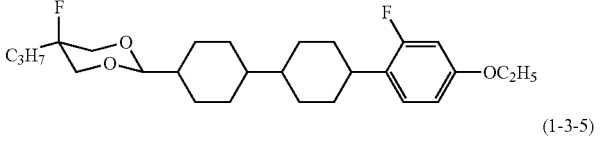
(1-3-4)
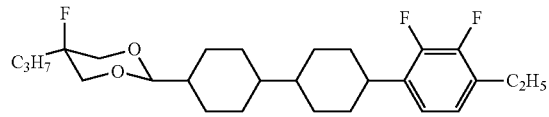
(1-3-5)
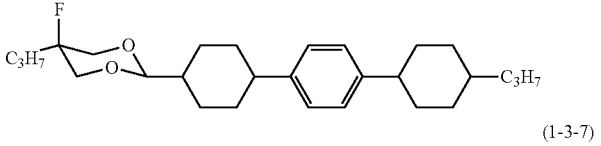
(1-3-6)
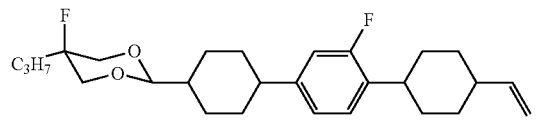
(1-3-7)
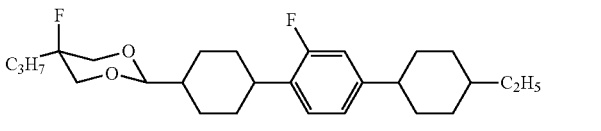
(1-3-8)
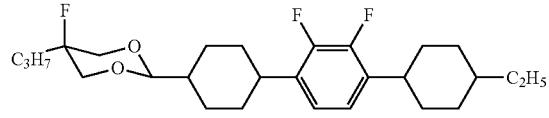
(1-3-9)
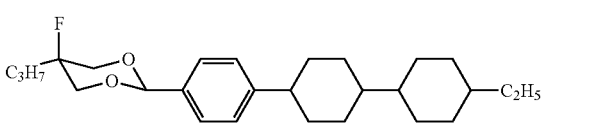

-continued
(1-3-10)
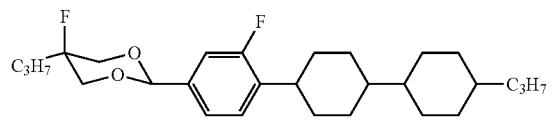
(1-3-11)
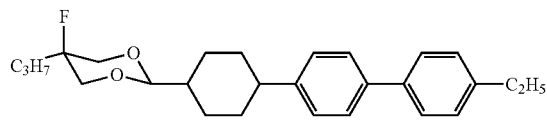
(1-3-12)
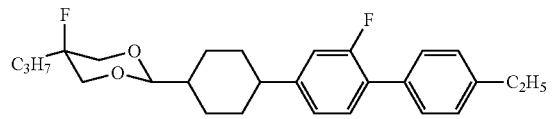
(1-3-13)
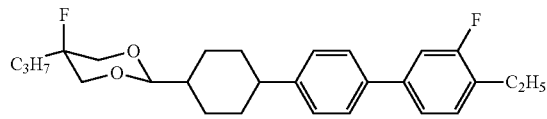
(1-3-14)
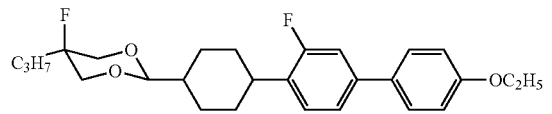
(1-3-15)
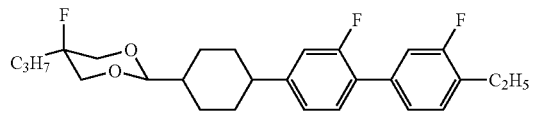
(1-3-16)
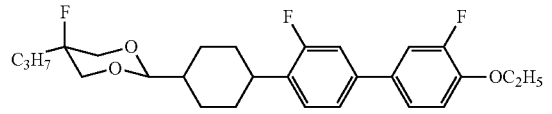
(1-3-17)
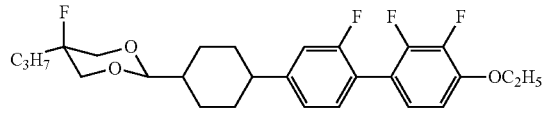
(1-3-18)
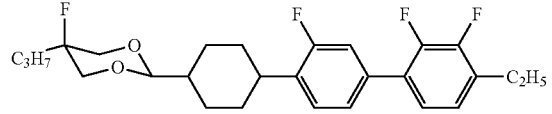
(1-3-19)
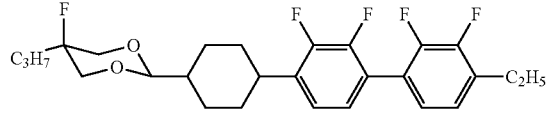
(1-3-20)
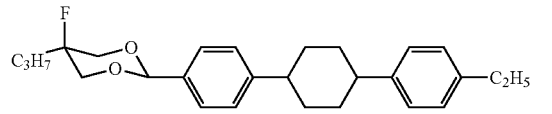
(1-3-21)
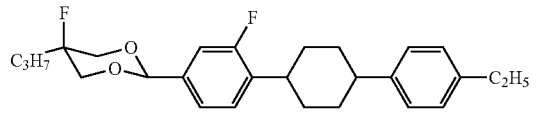
(1-3-22)
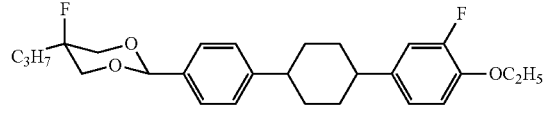
(1-3-23)
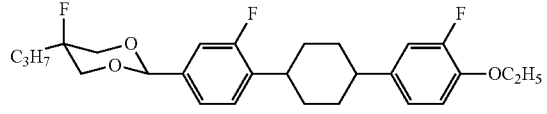
(1-3-24)
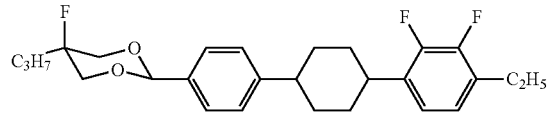
(1-3-25)
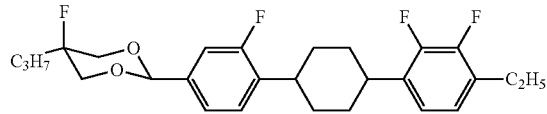
(1-3-26)
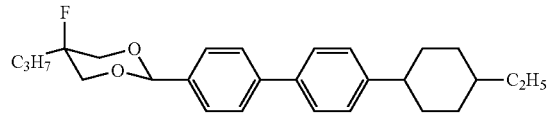
(1-3-27)
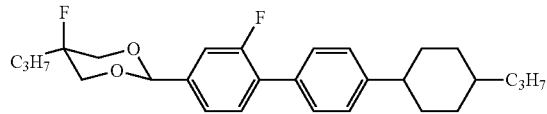
(1-3-28)
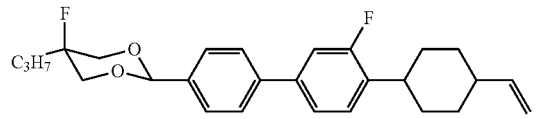
(1-3-29)
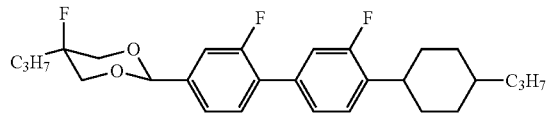
(1-3-30)
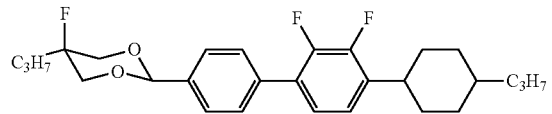

-continued
(1-3-32)
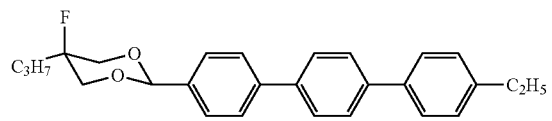
(1-3-33)
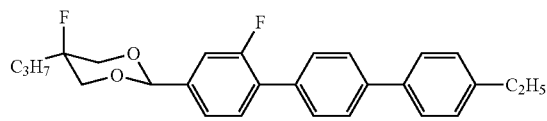
(1-3-34)
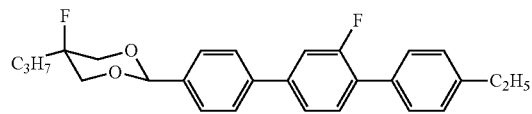
(1-3-35)
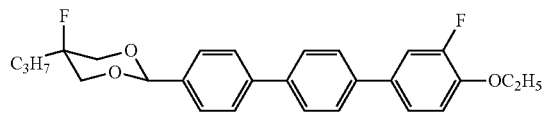
(1-3-36)
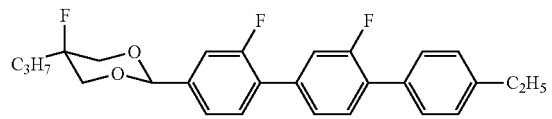
(1-3-37)
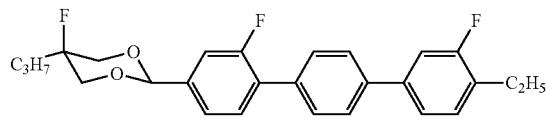
(1-3-38)
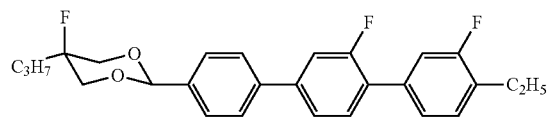
(1-3-39)
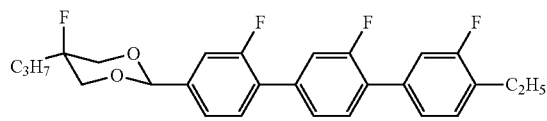
(1-3-40)
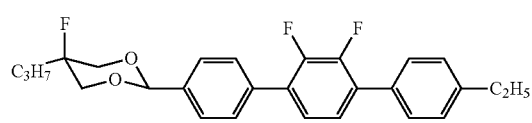
(1-3-41)
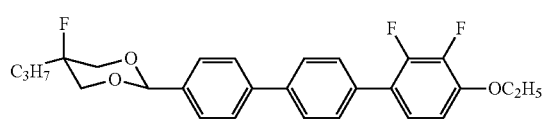
(1-3-42)
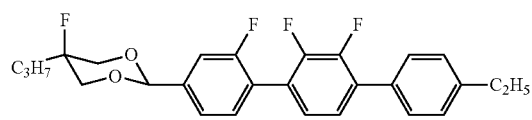
(1-3-43)
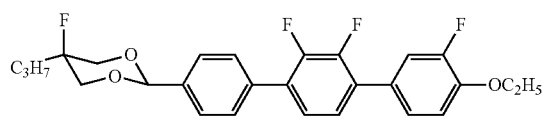
(1-3-44)
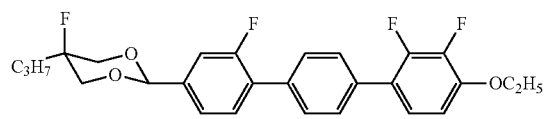
(1-3-45)
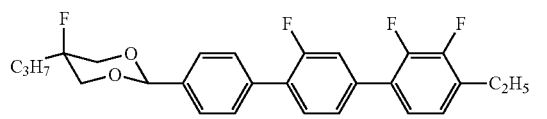
(1-3-46)
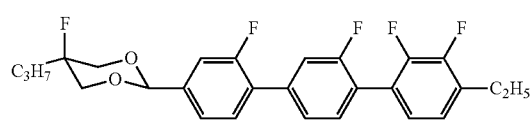
(1-3-47)
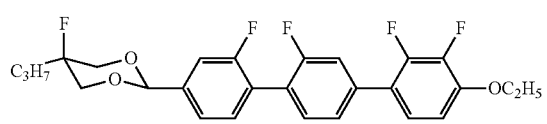
(1-3-48)
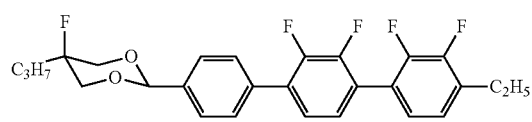
(1-3-49)
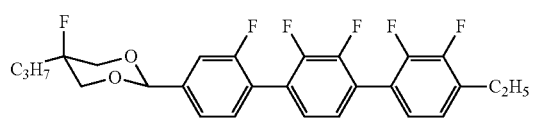
(1-3-50)
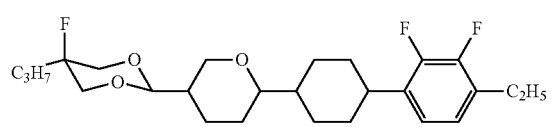
(1-3-51)
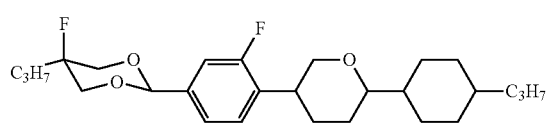
(1-3-52)
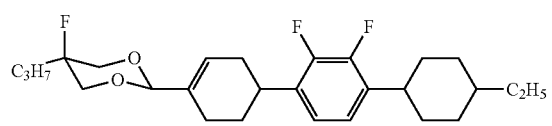
(1-3-53)
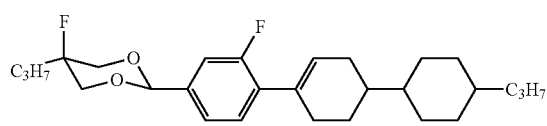

-continued
(1-3-54)
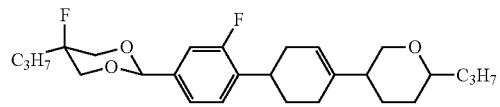
(1-3-55)
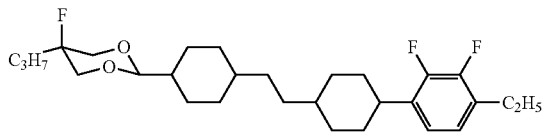
(1-3-56)
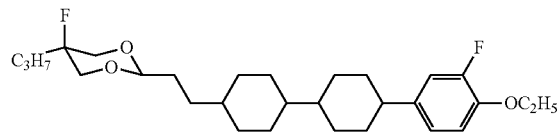
(1-3-57)
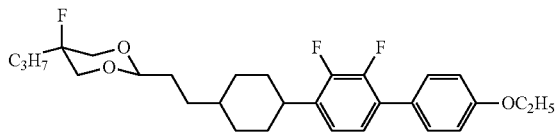
(1-3-58)
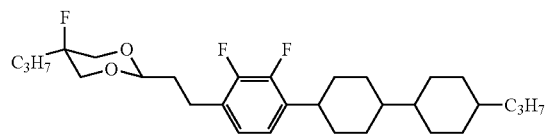
(1-3-59)
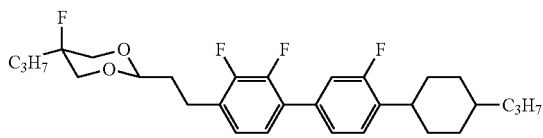
(1-3-60)
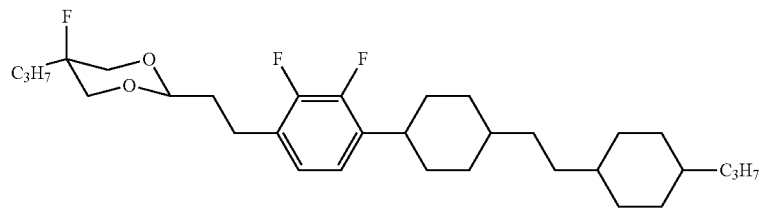
(1-3-61)
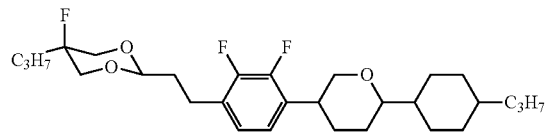
(1-3-62)
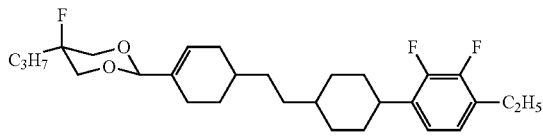
(1-3-63)
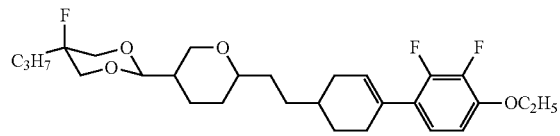
(1-3-64)
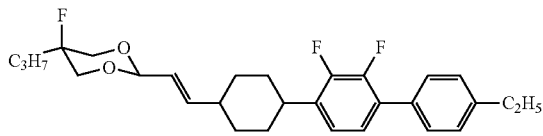
(1-3-65)
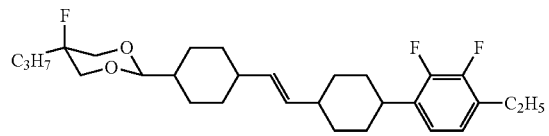
(1-3-66)
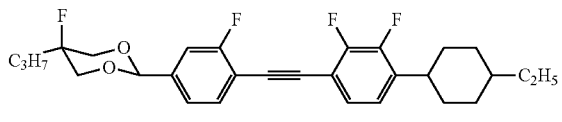
(1-3-67)
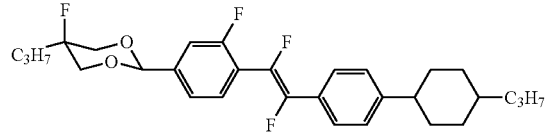
(1-3-68)
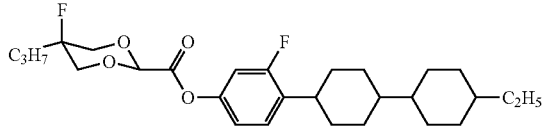
(1-3-69)
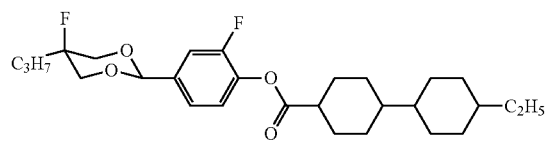
(1-3-70)
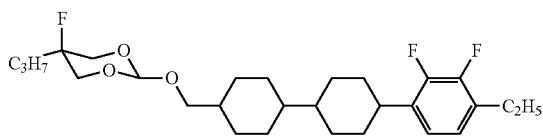

-continued
(1-3-71)
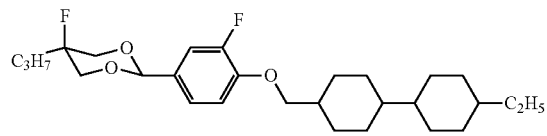
(1-3-72)
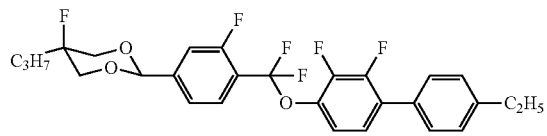
(1-3-73)
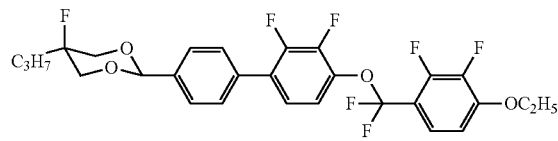
(1-3-74)
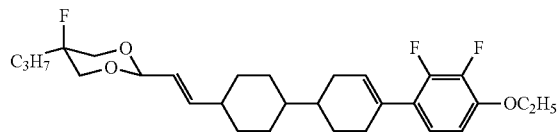
(1-3-75)
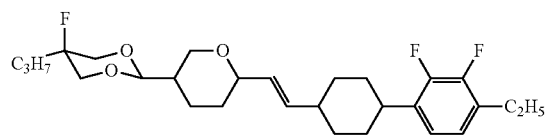
(1-3-76)
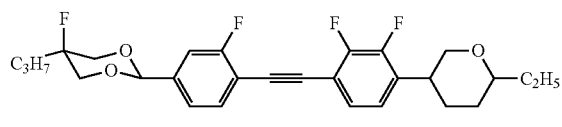
(1-3-77)
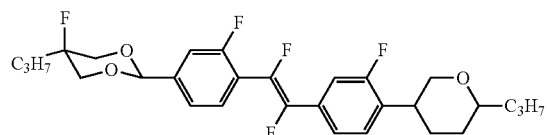
(1-3-78)
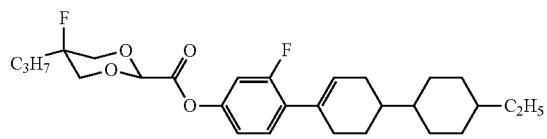
(1-3-79)
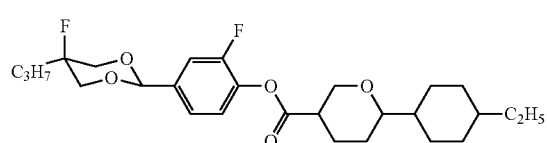
(1-3-80)
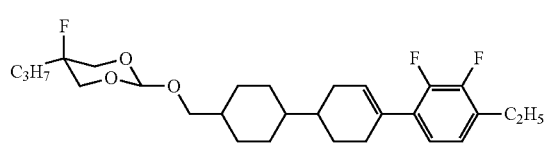
(1-3-81)
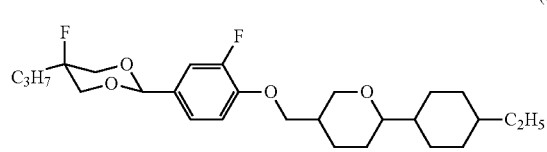
(1-3-82)
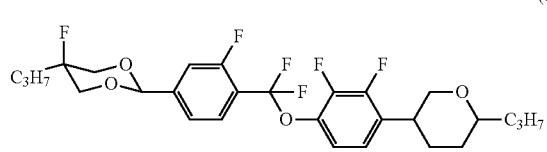
(1-3-83)
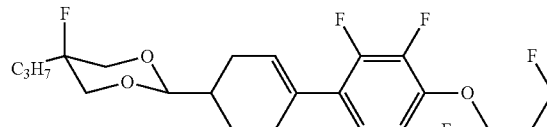
(1-3-84)
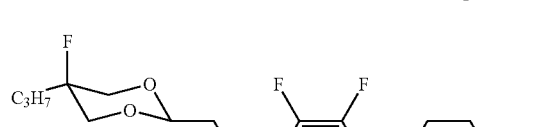
(1-3-85)
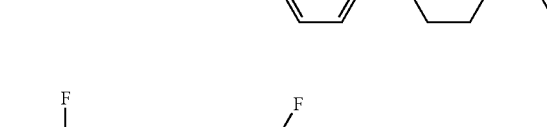

-continued
(1-3-86)
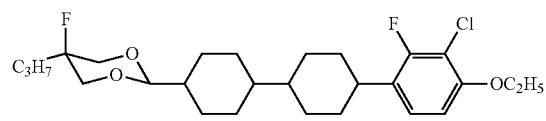
(1-3-87)
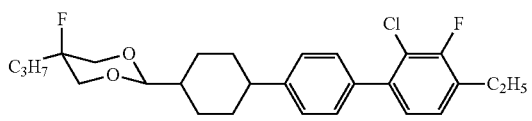
(1-3-88)
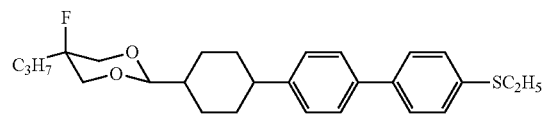
(1-3-89)
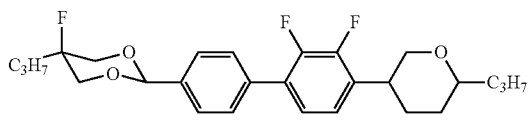
(1-3-90)
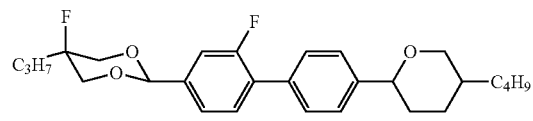
(1-3-91)
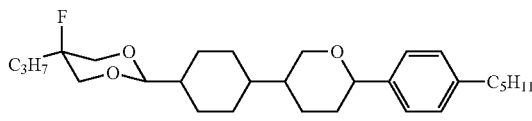
(1-3-92)
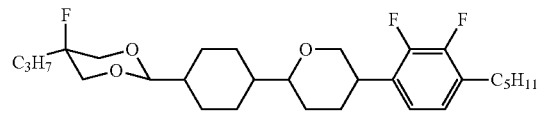
(1-3-93)
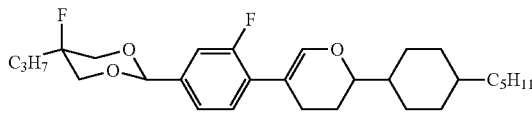
(1-3-94)
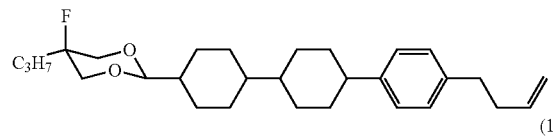
(1-3-95)
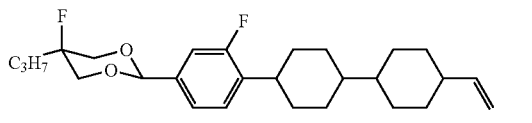
(1-3-96)
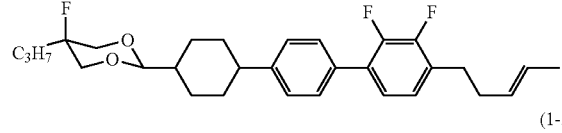
(1-3-97)
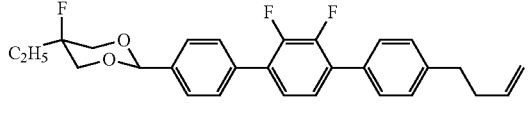
(1-3-98)
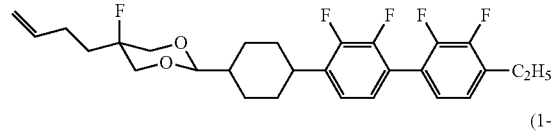
(1-3-99)
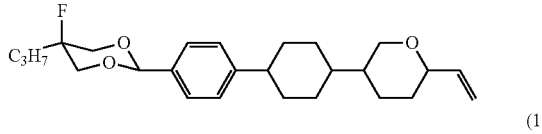
(1-3-100)
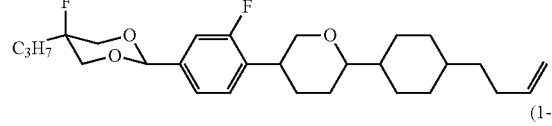
(1-3-101)
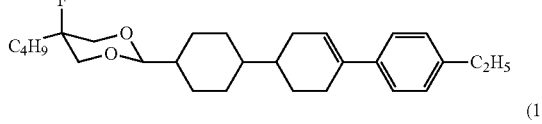
(1-3-102)
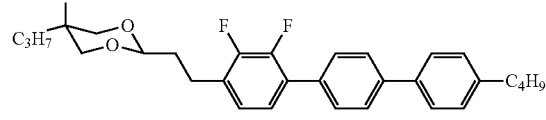
(1-3-103)
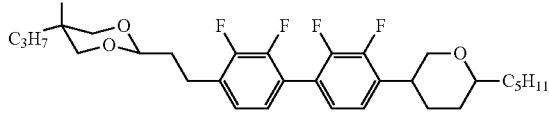
(1-3-104)
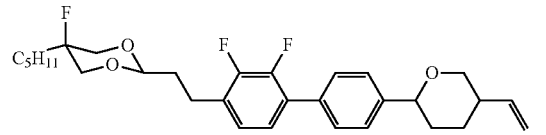
(1-3-105)
(1-3-106)

-continued (1-3-107)

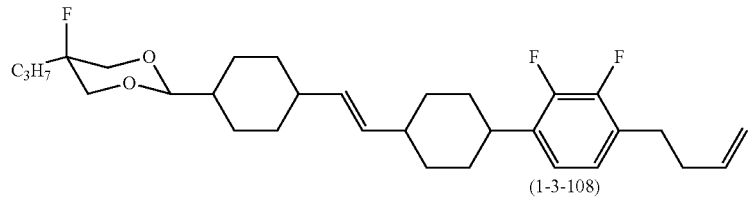

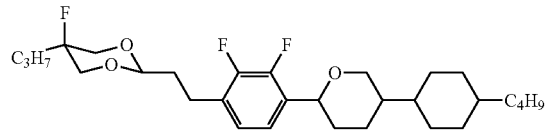
(1-3-108)

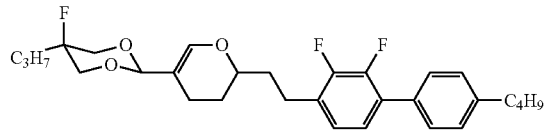
(1-3-109)

Comparative Example 1

Compound (C-1) was prepared as a comparative compound in order to compare the invention with a conventional technology. The compound is described in JP H11-12271 A.

Synthesis of Comparative Compound (C-1)

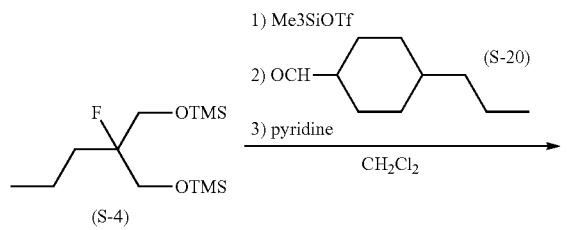

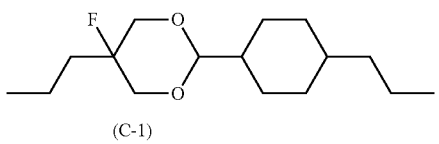

reduced pressure, and the residue was purified by silica gel column chromatography (heptane:ethyl acetate=20:1 in a volume ratio). The residue was further purified by recrystallization from heptane to give compound (C-1) having fluorine atom in axial position (0.17 g; 8.8%).

Chemical shifts δ (ppm; CDCl$_3$): 4.18 (d, J=5.8, 1H), 4.07 (dd, J=12.3, 2H), 3.61 (dd, J=35.3, J=12.8, 2H), 1.90-1.83 (m, 2H), 1.79-1.72 (m, 2H), 1.61-1.52 (m, 1H), 1.46-1.35 (m, 4H), 1.35-1.24 (m, 2H), 1.22-1.11 (m, 3H), 1.05 (dq, J=13.0, J=3.4, 2H), 0.96-0.80 (m, 8H).

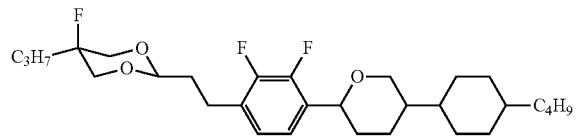
(1-3-108)

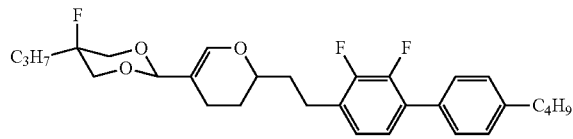
(1-3-109)

First Step

Under a nitrogen atmosphere, compound (S-4) (2.00 g), trimethylsilyl trifluoromethanesulfonate (0.12 mL) and dichloromethane (10 mL) were put in a reaction vessel, and the resulting mixture was cooled to −70° C. A dichloromethane (5 mL) solution of compound (S-20) (1.25 g) prepared according to a publicly known method was slowly added thereto, and the resulting mixture was stirred for 2 hours. Pyridine (0.75 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under Physical properties of comparative compound (C-1) were as described below. In addition, for measurement of maximum temperature, optical anisotropy, dielectric anisotropy and viscosity, a sample in which a ratio of the compound to the base liquid crystal was 5% by weight: 95% by weight was used.

Transition temperature: C 114 I.

Maximum temperature (T$_{NI}$)=28.6° C.; optical anisotropy (Δn)=0.0510; dielectric anisotropy (Δ∈)=−4.01; and viscosity (η)=53.3 mPa·s.

When physical properties of compound (1-1-1) obtained in Example 1 and physical properties of comparative compound (C-1) were compared, compound (1-1-1) was found to be superior to comparative compound (C-1) in view of a high compatibility with other liquid crystal compounds.

Comparative Example 2

Compound (C-2) was prepared as a comparative compound. Compound (C-2) is described in WO 1998/014418 A.

Synthesis of Comparative Compound (C-2)

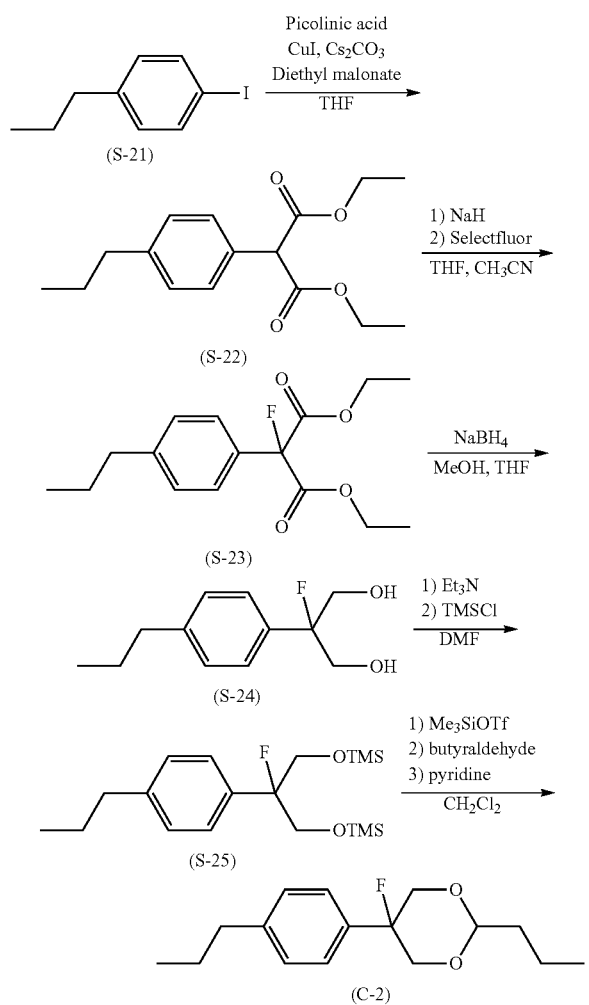

First Step

Under a nitrogen atmosphere, picolinic acid (4.50 g), copper iodide (I) (3.48 g), cesium carbonate (59.6 g) and THF (75 mL) were put in a reaction vessel, and the resulting mixture was stirred at room temperature. Compound (S-21) (15.0 g) prepared according to a publicly known method and diethyl malonate (19.5 g) were slowly added thereto, and the resulting mixture was stirred at 70° C. for 6 hours. The resulting reaction mixture was poured into a saturated aqueous solution of ammonium chloride, and an aqueous layer was subjected to extraction with ethyl acetate. Organic layers were washed with water and saturated brine, and then dried over anhydrous magnesium sulfate. The resulting solution was concentrated under reduced pressure, and the residue was purified by silica gel column chromatography (heptane:ethyl acetate=4:1 in a volume ratio) to give compound (S-22) (16.0 g; 94%).

Second Step

Under a nitrogen atmosphere, sodium hydride (3.75 g) and THF (100 mL) were put in a reaction vessel, and the resulting mixture was cooled to 0° C. A THF (10 mL) solution of compound (S-22) (16.0 g) was slowly added thereto, and the resulting mixture was stirred for 2 hours. The resulting reaction mixture was heated to room temperature, and stirred for 1 hour. The resulting reaction mixture was heated to 40° C., and stirred for 4 hours. The resulting reaction mixture was cooled to 0° C., an acetonitrile (100 mL) suspension of Selectfluor (20.3 g) was added thereto, and the resulting mixture was heated to room temperature. The resulting reaction mixture was poured into water, and an aqueous layer was subjected to extraction with diethyl ether. Organic layers combined were washed with water, a 1 N hydrochloric acid solution, saturated sodium bicarbonate water and saturated brine, and dried over anhydrous magnesium sulfate. The resulting solution was concentrated under reduced pressure, and the residue was purified by silica gel column chromatography (heptane:ethyl acetate=2:1 in a volume ratio) to give compound (S-23) (15.7 g; 93%).

Third Step

Under a nitrogen atmosphere, compound (S-23) (15.7 g), methanol (90 mL) and THF (15 mL) were put in a reaction vessel, and the resulting mixture was stirred at room temperature. Sodium borohydride (10.0 g) was added little by little thereto, and the resulting mixture was stirred for 2 hours. The resulting reaction mixture was poured into ice water, and an aqueous layer was subjected to extraction with ethyl acetate. Organic layers combined were washed with saturated brine, and dried over anhydrous magnesium sulfate. The resulting solution was concentrated under reduced pressure to give a crude product of compound (S-24) (8.61 g; 76%).

Fourth Step

Under a nitrogen atmosphere, compound (S-24) (8.61 g), triethylamine (31.1 mL) and N,N-dimethylformamide (50 mL) were put in a reaction vessel, and the resulting mixture was stirred at room temperature. Chlorotrimethylsilane (14.3 mL) was slowly added thereto, and the resulting mixture was stirred for 1 hour. The resulting reaction mixture was poured into water, and an aqueous layer was subjected to extraction with toluene. Organic layers combined were washed with water and saturated brine, and dried over anhydrous magnesium sulfate. The resulting solution was concentrated under reduced pressure to give a crude product of compound (S-25) (14.5 g; 100%).

Fifth Step

Under a nitrogen atmosphere, compound (S-25) (14.5 g), trimethylsilyl trifluoromethanesulfonate (0.66 mL) and dichloromethane (90 mL) were put in a reaction vessel, and the resulting mixture was cooled to −70° C. A dichloromethane (20 mL) solution of butyraldehyde (4.17 mL) was slowly added thereto, and the resulting mixture was stirred for 2 hours. Pyridine (4.27 mL) was added thereto, and then the resulting mixture was heated to room temperature. The resulting reaction mixture was poured into saturated sodium bicarbonate water, and an organic layer was washed with water and saturated brine, and then dried over anhydrous magnesium sulfate. The resulting solution was concentrated under reduced pressure, and the residue was purified by silica gel column chromatography (heptane:ethyl acetate=20:1 in a volume ratio). The residue was further purified by recrystallization from heptane to give compound (C-2) having fluorine atom in axial position (3.53 g; 33%).

Chemical shifts δ (ppm; CDCl$_3$): 7.29 (d, J=8.2 Hz, 2H), 7.21 (d, J=8.2, 2H), 4.69 (t, J=5.2, 1H), 4.19-4.12 (m, 2H), 4.08-3.96 (m, 2H), 2.59 (t, J=7.5 Hz, 2H), 1.77-1.71 (m, 2H), 1.68-1.58 (m, 2H), 1.54-1.44 (m, 2H), 0.98-0.91 (m, 6H).

Physical properties of comparative compound (C-2) were as described below.

Transition temperature: C 42.6 I.

Maximum temperature $(T_{NI})$=–81.4° C.; optical anisotropy ($\Delta n$)=0.0217; dielectric anisotropy ($\Delta\epsilon$)=–0.82; and viscosity ($\eta$)=47.4 mPa·s.

When physical properties of compound (1-1-1) obtained in Example 1 and physical properties of comparative compound (C-2) were compared, compound (1-1-1) was found to be superior to comparative compound (C-2) in that compound (1-1-1) showed a higher clearing point and a larger negative dielectric anisotropy.

1-2. Example of Composition (1)

Liquid crystal composition (1) of the invention will be described in detail by way of Examples. The invention is not restricted by the Examples. The invention includes a mixture of a composition in Example 6 and a composition in Example 7. The invention also includes a mixture obtained by mixing at least two compositions in Examples. Compounds in Examples were expressed using symbols according to definitions in Table 1 described below. In Table 1, a configuration of 1,4-cyclohexylene is trans. A parenthesized number next to a symbolized compound in Examples corresponds to the number of the compound. A symbol (–) means any other liquid crystal compound. A ratio (percentage) of a liquid crystal compound is expressed in terms of weight percentage (% by weight) based on the total weight of the liquid crystal composition. Values of physical properties of the composition were summarized in a last part. The physical properties were measured according to the methods described above, and were directly described without extrapolating measured values.

TABLE 1

| Method for Description of Compounds using Symbols R—($A_1$)—$Z_1$— ... —$Z_n$—($A_n$)—R' | |
|---|---|
| 1) Left-terminal Group R— | Symbol |
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| 2) Right-terminal Group —R' | Symbol |
| —$C_nH_{2n+1}$ | -n |
| —$OC_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | —nV |
| —$C_mH_{2m}$—CH=CH—$C_nH_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —CF=CH—CF$_3$ | —FVCF3 |
| —C≡N | —C |

TABLE 1-continued

| Method for Description of Compounds using Symbols R—($A_1$)—$Z_1$— ... —$Z_n$—($A_n$)—R' | |
|---|---|
| 3) Bonding Group —$Z_n$— | Symbol |
| —$C_nH_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —$A_n$— | Symbol |
| cyclohexane | H |
| benzene | B |
| fluorobenzene (F) | B(F) |
| 2-fluorobenzene | B(2F) |
| difluorobenzene | B(F,F) |
| 2,5-difluorobenzene | B(2F,5F) |
| 2,3-difluorobenzene | B(2F,3F) |
| 2-fluoro-3-chlorobenzene | B(2F,3CL) |
| dioxane | G |
| tetrahydropyran | dh |

TABLE 1-continued

Method for Description of Compounds using Symbols
R—(A₁)—Z₁—...—Zₙ—(Aₙ)—R'

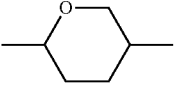 Dh

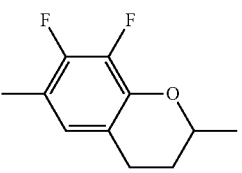 Cro(7F,8F)

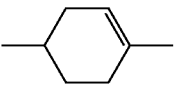 ch

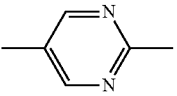 Py

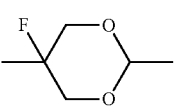 G(5F)

5) Examples of Description

Example 1  3-G(5F)B-3

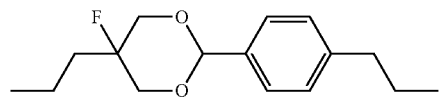 [SMILES: CCCc1ccc(C2OCC(F)(CCC)CO2)cc1]

Example 2  3-G(5F)BB(2F,3F)—O2

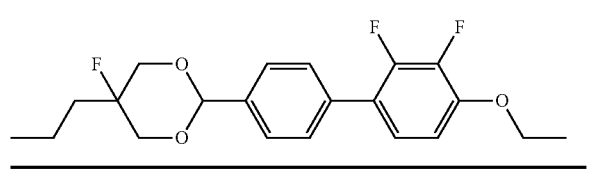

Example 7

| | | |
|---|---|---|
| 3-G(5F)B-3 | (1-1-1) | 5% |
| 3-HB-O2 | (13-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |
| 5-HBB(F)B-2 | (15-5) | 8% |
| 5-HBB(F)B-3 | (15-5) | 7% |

NI=87.3° C.; Δn=0.181; Δ∈=7.6; η=39.6 mPa·s.

Example 8

| | | |
|---|---|---|
| 3-G(5F)B(F)-O2 | (1-1-4) | 5% |
| 2-HB-C | (5-1) | 4% |
| 3-HB-C | (5-1) | 12% |
| 3-HB-O2 | (13-5) | 14% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 3% |
| 5-HHEB-F | (3-10) | 3% |
| 2-HHB(F)-F | (3-2) | 7% |
| 3-HHB(F)-F | (3-2) | 7% |
| 5-HHB(F)-F | (3-2) | 6% |
| 3-HHB(F,F)-F | (3-3) | 5% |

NI=95.6° C.; Δn=0.100; Δ∈=4.1; η=19.8 mPa·s.

Example 9

| | | |
|---|---|---|
| 3-G(5F)HB-2 | (1-2-1) | 5% |
| 5-HB-CL | (2-2) | 16% |
| 3-HH-4 | (13-1) | 12% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=110.5° C.; Δn=0.089; Δ∈=3.1; η=18.7 mPa·s.

Example 10

| | | |
|---|---|---|
| 3-G(5F)BB(2F,3F)-2 | (1-2-30) | 5% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 10% |
| 5-HHEBB-F | (4-17) | 2% |
| 3-HH2BB(F,F)-F | (4-15) | 3% |
| 1O1-HBBH-4 | (15-1) | 3% |
| 1O1-HBBH-5 | (15-1) | 3% |

NI=92.6° C.; Δn=0.116; Δ∈=8.4; η=36.1 mPa·s.

Example 11

| | | |
|---|---|---|
| 3-G(5F)BB(2F,3F)-O2 | (1-2-31) | 5% |
| 5-HB-F | (2-2) | 12% |
| 6-HB-F | (2-2) | 9% |
| 7-HB-F | (2-2) | 7% |
| 2-HHB-OCF3 | (3-1) | 5% |
| 3-HHB-OCF3 | (3-1) | 5% |
| 4-HHB-OCF3 | (3-1) | 7% |

-continued

| | | |
|---|---|---|
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 4% |
| 3-HH2B(F)-F | (3-5) | 3% |
| 3-HBB(F)-F | (3-23) | 10% |
| 5-HBB(F)-F | (3-23) | 10% |
| 5-HBBH-3 | (15-1) | 3% |
| 3-HB(F)BH-3 | (15-2) | 3% |

NI=88.5° C.; Δn=0.098; Δ∈=3.7; η=18.4 mPa·s.

Example 12

| | | |
|---|---|---|
| 3-G(5F)2B(2F,3F)-O2 | (1-1-15) | 5% |
| 5-HB-CL | (2-2) | 3% |
| 7-HB(F)-F | (2-3) | 7% |
| 3-HH-4 | (13-1) | 9% |
| 3-HH-EMe | (13-2) | 23% |
| 3-HHEB-F | (3-10) | 8% |
| 5-HHEB-F | (3-10) | 8% |
| 3-HHEB(F,F)-F | (3-12) | 8% |
| 4-HHEB(F,F)-F | (3-12) | 4% |
| 4-HGB(F,F)-F | (3-103) | 4% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 6% |

NI=74.6° C.; Δn=0.064; Δ∈=5.0.

Example 13

| | | |
|---|---|---|
| 3-G(5F)B(F)H-V | (1-2-21) | 5% |
| 3-HB-O1 | (13-5) | 13% |
| 3-HH-4 | (13-1) | 5% |
| 3-HB(2F,3F)-O2 | (6-4) | 12% |
| 5-HB(2F,3F)-O2 | (6-4) | 12% |
| 2-HHB(2F,3F)-1 | (7-1) | 10% |
| 3-HHB(2F,3F)-1 | (7-1) | 11% |
| 3-HHB(2F,3F)-O2 | (7-1) | 13% |
| 5-HHB(2F,3F)-O2 | (7-1) | 13% |
| 3-HHB-1 | (14-1) | 6% |

Example 14

| | | |
|---|---|---|
| 3-G(5F)B(F)dh-3 | (1-2-60) | 5% |
| 2-HH-5 | (13-1) | 3% |
| 3-HH-4 | (13-1) | 15% |
| 3-HB-O2 | (13-5) | 12% |
| 3-H2B(2F,3F)-O2 | (6-4) | 15% |
| 5-H2B(2F,3F)-O2 | (6-4) | 15% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 8% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

Example 15

| | | |
|---|---|---|
| 2-G(5F)chB(2F,3F)-2 | (1-2-45) | 5% |
| 2-HH-3 | (13-1) | 18% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 13% |
| 3-HH1OB(2F,3F)-O2 | (7-5) | 19% |
| 3-HHB-1 | (14-1) | 5% |
| 3-HHB-O1 | (14-1) | 3% |
| 5-B(F)BB-2 | (14-8) | 2% |

Example 16

| | | |
|---|---|---|
| 2-G(5F)dhB(F)-2 | (1-2-48) | 5% |
| 2-HH-3 | (13-1) | 16% |
| 7-HB-1 | (13-5) | 10% |
| 5-HB-O2 | (13-5) | 8% |
| 3-HB(2F,3F)-O2 | (6-1) | 15% |
| 5-HB(2F,3F)-O2 | (6-1) | 14% |
| 3-HHB(2F,3CL)-O2 | (7-12) | 3% |
| 4-HHB(2F,3CL)-O2 | (7-12) | 3% |
| 5-HHB(2F,3CL)-O2 | (7-12) | 2% |
| 3-HH1OCro(7F,8F)-5 | (10-6) | 4% |
| 5-HBB(F)B-2 | (15-5) | 10% |
| 5-HBB(F)B-3 | (15-5) | 10% |

Example 17

| | | |
|---|---|---|
| 3-G(5F)B-3 | (1-1-1) | 3% |
| 3-G(5F)B(F)-O2 | (1-1-4) | 4% |
| 2-HH-3 | (13-1) | 6% |
| 3-HH-V1 | (13-1) | 10% |
| 1V2-HH-1 | (13-1) | 8% |
| 1V2-HH-3 | (13-1) | 7% |
| 3-BB(2F,3F)-O2 | (6-3) | 8% |
| 5-BB(2F,3F)-O2 | (6-3) | 4% |
| 3-H1OB(2F,3F)-O2 | (6-5) | 7% |
| 2-HH1OB(2F,3F)-O2 | (7-5) | 8% |
| 3-HH1OB(2F,3F)-O2 | (7-5) | 15% |
| 3-HDhB(2F,3F)-O2 | (7-3) | 6% |
| 3-HHB-1 | (14-1) | 3% |
| 3-HHB-3 | (14-1) | 2% |
| 2-BB(2F,3F)B-3 | (8-1) | 9% |

NI=76.9° C.; Δn=0.104; Δ∈=−4.3; η=22.8 mPa·s.

Example 18

| | | |
|---|---|---|
| 3-G(5F)HB-2 | (1-2-1) | 5% |
| 1V2-BEB(F,F)-C | (5-15) | 6% |
| 3-HB-C | (5-1) | 13% |
| 2-BTB-1 | (13-10) | 10% |
| 5-HH-VFF | (13-1) | 30% |
| 3-HHB-1 | (14-1) | 4% |
| VFF-HHB-1 | (14-1) | 8% |
| VFF2-HHB-1 | (14-1) | 11% |
| 3-H2BTB-2 | (14-17) | 5% |
| 3-H2BTB-3 | (14-17) | 4% |
| 3-H2BTB-4 | (14-17) | 4% |

NI=84.1° C.; Δn=0.129; Δδ=5.7; η=13.9 mPa·s.

Example 19

| | | |
|---|---|---|
| 3-G(5F)BB(2F,3F)-2 | (1-2-30) | 3% |
| 3-G(5F)BB(2F,3F)-O2 | (1-2-31) | 3% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 35% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 6% |
| 3-GB(F,F)XB(F,F)-F | (3-113) | 5% |
| 3-HHBB(F,F)-F | (4-6) | 3% |

NI=86.5° C.; Δn=0.111; Δ∈=7.1; η=20.1 mPa·s.

Example 20

| | | |
|---|---|---|
| 3-G(5F)BB(2F,3F)-2V | (1-2-182) | 2% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 5% |
| 5-BB(F)B(F,F)XB(F,F)-F | (4-47) | 3% |
| 3-HH-V | (13-1) | 41% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 6% |
| 3-GB(F,F)XB(F,F)-F | (3-113) | 5% |
| 3-HHBB(F,F)-F | (4-6) | 3% |

NI=81.9° C.; Δn=0.103; Δ∈=6.7; η=12.9 mPa·s.

Example 21

| | | |
|---|---|---|
| 3-G(5F)BB(2F,3F)-2V | (1-2-182) | 3% |
| 3-HB-O1 | (13-5) | 15% |
| 3-HH-4 | (13-1) | 5% |
| 3-HB(2F,3F)-O2 | (6-1) | 12% |
| 5-HB(2F,3F)-O2 | (6-1) | 11% |
| 2-HHB(2F,3F)-1 | (7-1) | 12% |
| 3-HHB(2F,3F)-1 | (7-1) | 11% |
| 3-HHB(2F,3F)-O2 | (7-1) | 12% |
| 5-HHB(2F,3F)-O2 | (7-1) | 13% |
| 3-HHB-1 | (14-1) | 6% |

NI=87.2° C.; Δn=0.093; Δ∈=−3.4; η=36.6 mPa·s.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has a high stability to heat, light and so forth, a high clearing point, a low minimum temperature of a liquid crystal phase, a small viscosity, a suitable optical anisotropy, a large negative dielectric anisotropy, a suitable elastic constant and an excellent compatibility with other liquid crystal compounds. A liquid crystal composition of the invention contains the compound, and has a high maximum temperature of a nematic phase, a low minimum temperature of the nematic phase, a small viscosity, a suitable optical anisotropy, a large negative dielectric anisotropy and a suitable elastic constant. The composition has a suitable balance regarding at least two of physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a display of a personal computer, a television and so forth.

What is claimed is:

1. A compound represented by formula (1):

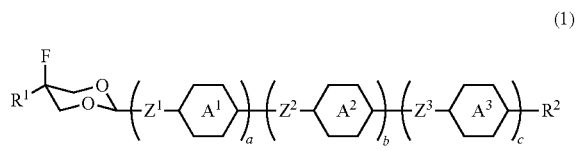

(1)

wherein, in formula (1), $R^1$ and $R^2$ are independently alkyl having 1 to 15 carbons, and in the alkyl, at least one of —$CH_2$— may be replaced by —O— or —S—, and at least one of —$(CH_2)_2$— may be replaced by —CH=CH—;

ring $A^1$, ring $A^2$ and ring $A^3$ are independently 1,4-cyclohexylene, 1,4-phenylene, 1,4-phenylene in which at least one of hydrogen is replaced by halogen, tetrahydropyran-2,5-diyl, or tetrahydropyran-2,5-diyl in which at least one of hydrogen is replaced by halogen, and in the rings, at least one of —$(CH_2)_2$— may be replaced by —CH=CH—, and at least one of ring $A^1$, ring $A^2$ and ring $A^3$ is represented by formula (A):

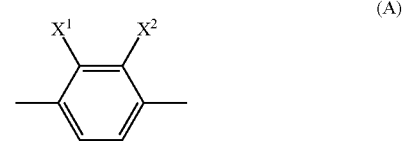

(A)

wherein, $X^1$ and $X^2$ are independently hydrogen or halogen; and $Z^1$, $Z^2$ and $Z^3$ are independently a single bond, —$(CH_2)_2$—, —CH=CH—, —C≡C—, —COO—, —OCO—, —$CH_2O$—, —$OCH_2$—, —$CF_2O$—, —$OCF_2$— or —CF=CF—, wherein, in the case where both $X^1$ and $X^2$ are fluorine when ring $A^1$ is represented by formula (A), $Z^1$ is —$(CH_2)_2$—, —CH=CH—, —$CH_2O$— or —$OCH_2$—; and a, b and c are independently 0 or 1, and a sum of a, b and c is 1, 2 or 3.

2. The compound according to claim 1, represented by formulas (1-1) to (1-3):

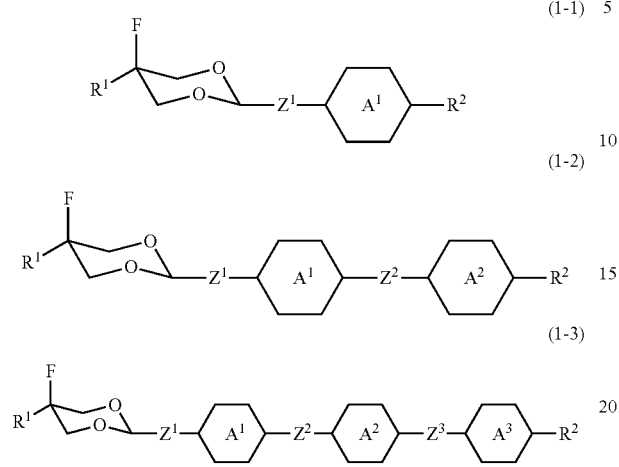

wherein, in formulas (1-1) to (1-3),
  $R^1$ and $R^2$ are independently alkyl having 1 to 15 carbons, alkoxy having 1 to 14 carbons, alkenyl having 2 to 15 carbons and alkenyloxy having 2 to 14 carbons;
  ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by halogen, tetrahydropyran-2,5-diyl or dihydropyrane-2,5-diyl, but at least one is a ring represented by formula (A):

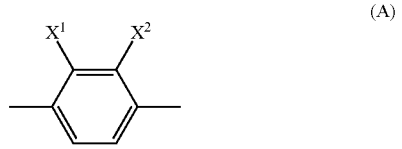

wherein, $X^1$ and $X^2$ are independently hydrogen or fluorine; and
  $Z^1$, $Z^2$ and $Z^3$ are independently a single bond, —(CH$_2$)$_2$—, —CH—CH—, —COO—, —OCO—, —CH$_2$O—, —OCH$_2$—, —CF$_2$O— or —OCF$_2$—.

3. The compound according to claim 1, wherein $R^1$ and $R^2$ are independently alkyl having 1 to 15 carbons, alkoxy having 1 to 14 carbons, alkenyl having 2 to 15 carbons and alkenyloxy having 2 to 14 carbons, ring $A^1$, ring $A^2$ and ring $A^3$ are independently 1,4-cyclohexylene, 1,4-cyclohexenylene, 1,4-phenylene, 1,4-phenylene in which at least one of hydrogen is replaced by fluorine, tetrahydropyran-2,5-diyl or dihydropyrane-2,5-diyl, but at least one is a ring represented by formula (A):

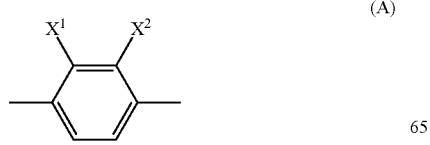

wherein, $X^1$ and $X^2$ are independently hydrogen or fluorine, and $Z^1$, $Z^2$ and $Z^3$ are independently a single bond, —(CH$_2$)$_2$—, —CH—CH—, —CH$_2$O— or —OCH$_2$—.

4. The compound according to claim 1, represented by formula (1-1-a), formula (1-1-b), formulas (1-2-a) to (1-2-k), formula (1-2-m), formulas (1-3-a) to (1-3-k) and formulas (1-3-m) to (1-3-t):

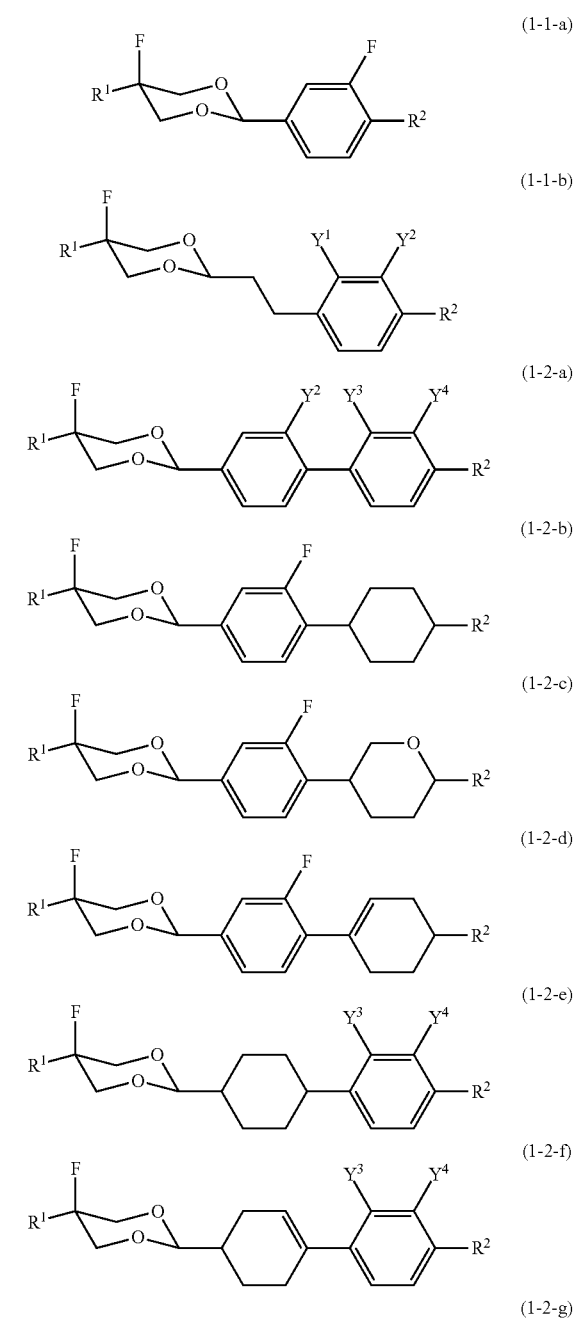

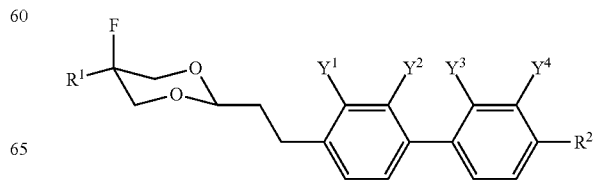

-continued
(1-2-h)
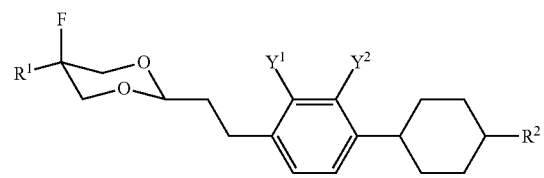
(1-2-i)
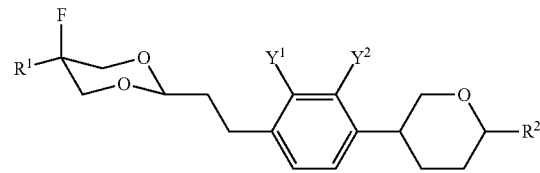
(1-2-j)
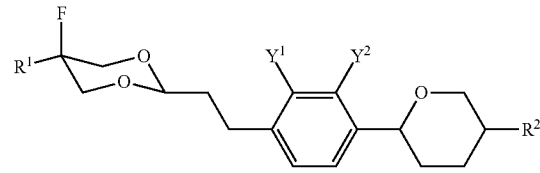
(1-2-k)
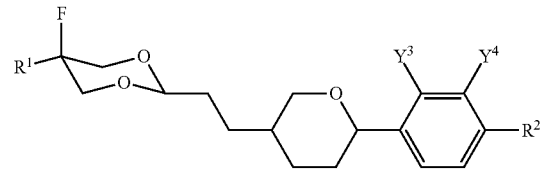
(1-2-m)
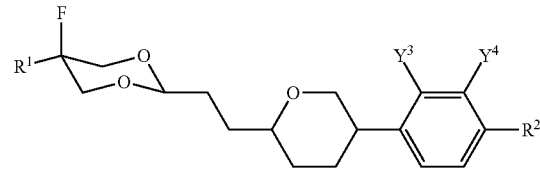
(1-3-a)
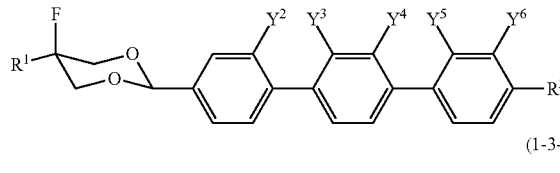
(1-3-b)
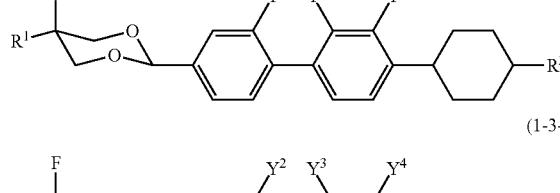
(1-3-c)
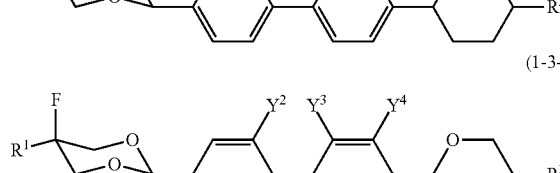
-continued
(1-3-e)
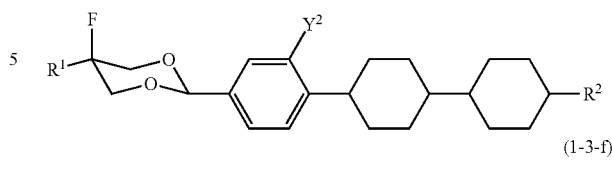
(1-3-f)
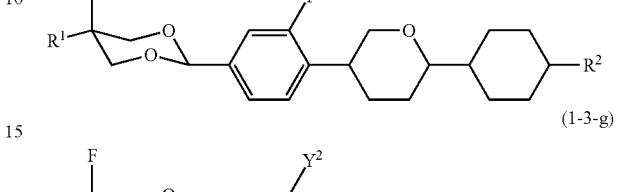
(1-3-g)
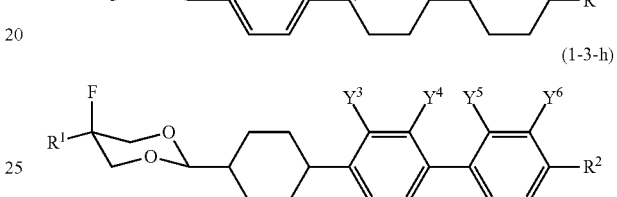
(1-3-h)
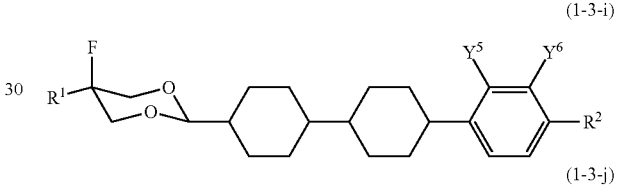
(1-3-i)
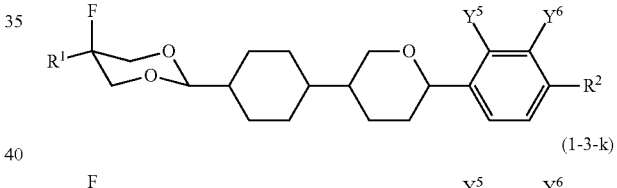
(1-3-j)
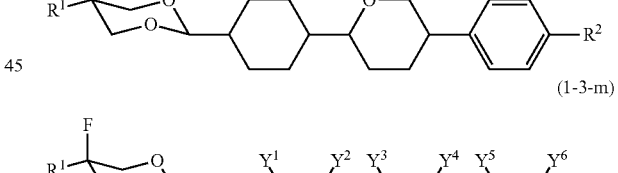
(1-3-k)
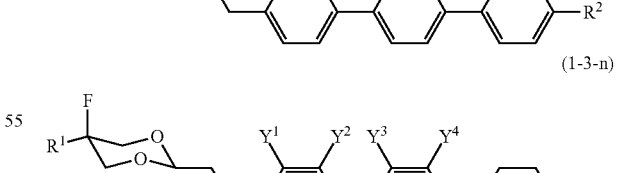
(1-3-m)
(1-3-n)
(1-3-o)
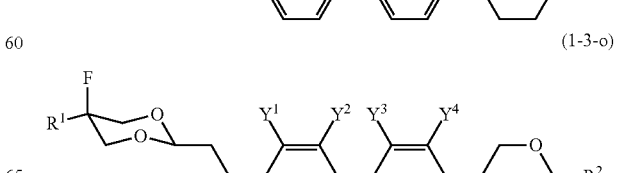

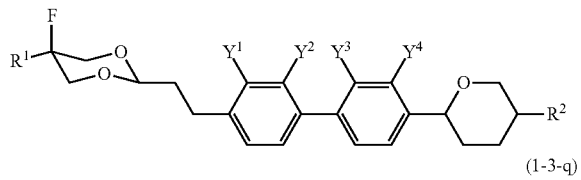
(1-3-p)

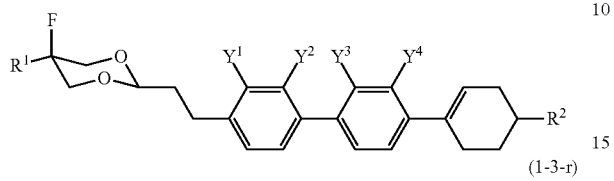
(1-3-q)

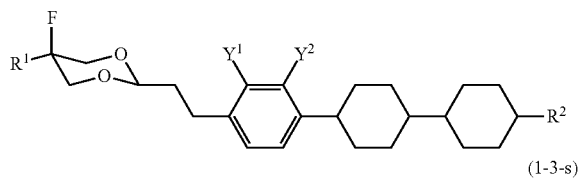
(1-3-r)

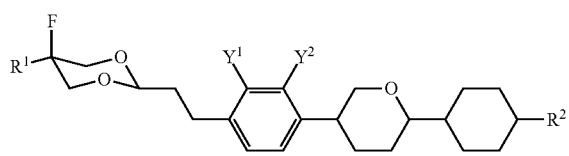
(1-3-s)

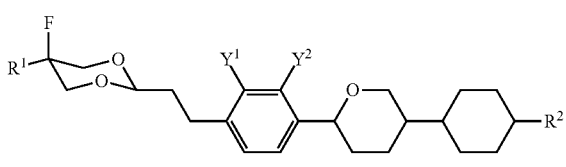
(1-3-t)

wherein, in formula (1-1-a), formula (1-1-b), formulas (1-2-a) to (1-2-k), formula (1-2-m), formulas (1-3-a) to (1-3-k) and formulas (1-3-m) to (1-3-t), $R^1$ and $R^2$ are independently alkyl having 1 to 10 carbons, alkoxy having 1 to 9 carbons, alkenyl having 2 to 10 carbons and alkenyloxy having 2 to 9 carbons; and $Y^1$ to $Y^6$ are independently hydrogen or fluorine.

5. A liquid crystal composition, containing at least one compound according to claim 1.

6. The liquid crystal composition according to claim 5, further containing at least one compound selected from the group of compounds represented by formulas (6) to (12):

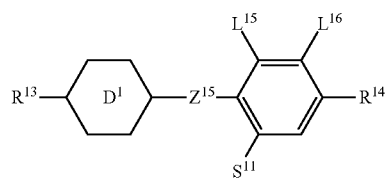
(6)

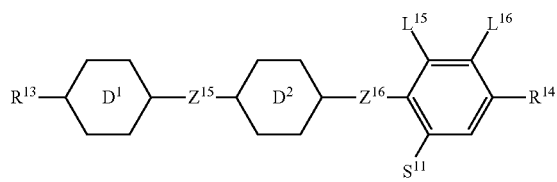
(7)

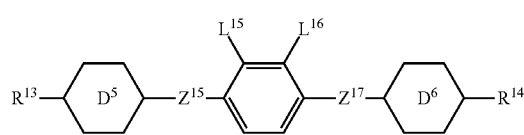
(8)

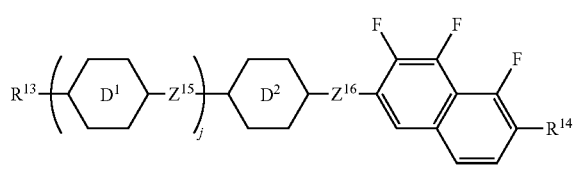
(9)

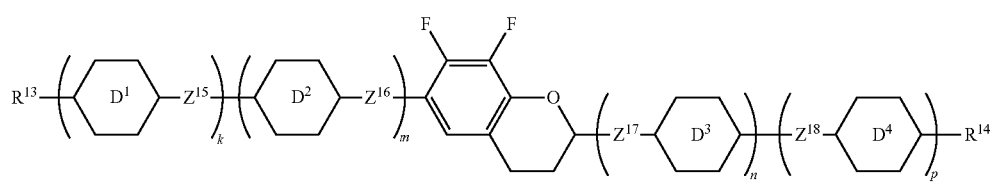
(10)

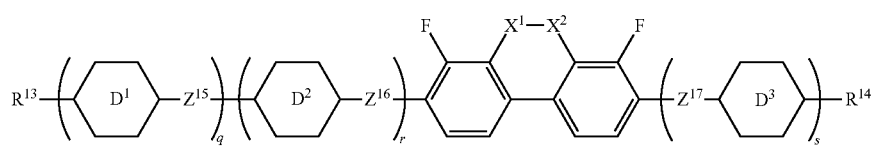
(11)

(12)

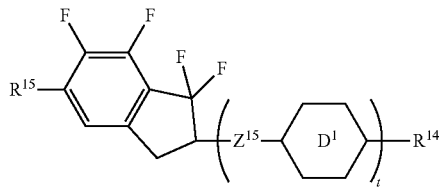

wherein, in formulas (6) to (12),
$R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$R^{14}$ is alkyl having 1 to 10 carbons, and in the alkyl, at least one of —$CH_2$— may be replaced by —O—, and at least one of hydrogen may be replaced by fluorine;
$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$S^{11}$ is hydrogen or methyl;
$X^1$ and $X^2$ are independently —$CF_2$—, —O— or —CHF—;
ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;
$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;
$L^{15}$ and $L^{16}$ are independently fluorine or chlorine; and
j, k, m, n, p, q, r and s are independently 0 or 1, a sum of k, m, n and p is 1 or 2, a sum of q, r and s is 0, 1, 2 or 3, and t is 1, 2 or 3.

7. The liquid crystal composition according to claim 5, further containing at least one compound selected from the group of compounds represented by formulas (13) to (15):

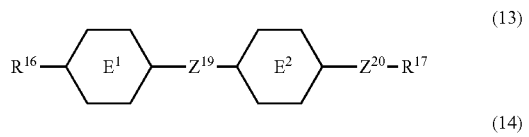
(13)

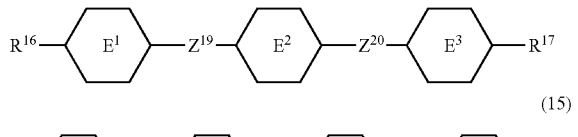
(14)

(15)

wherein, in formulas (13) to (15),
$R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and
$Z^{19}$, $Z^{20}$ and $Z^{21}$ are independently a single bond, —$CH_2CH_2$—, —CH=CH—, —C≡C— or —COO—.

8. The liquid crystal composition according to claim 5, further containing at least one compound selected from the group of compounds represented by formulas (2) to (4):

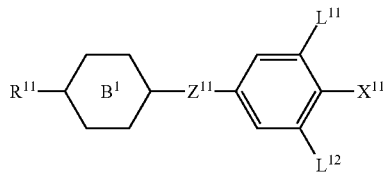
(2)

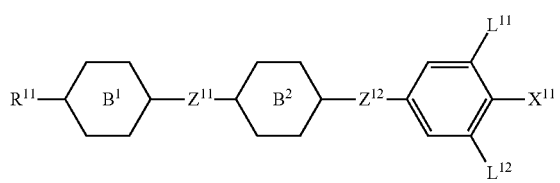
(3)

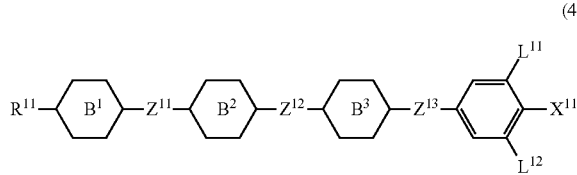
(4)

wherein, in formulas (2) to (4),
$R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
ring $B^1$, ring $B^2$ and ring $B^3$ are independently 1,4-cyclohexylene, 1,4-phenylene in which at least one of hydrogen is replaced by fluorine, tetrahydropyran-2,5-diyl, 1,3-dioxane-2,5-diyl or pyrimidine-2,5-diyl;
$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and
$L^{11}$ and $L^{12}$ are independently hydrogen or fluorine.

9. The liquid crystal composition according to claim 5, further containing at least one compound selected from the group of compounds represented by formula (5):

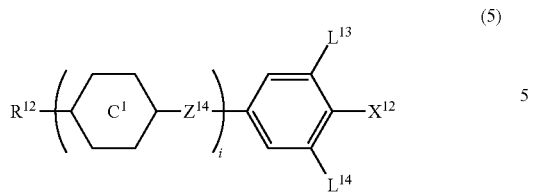

(5)

wherein, in formula (5),
- $R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
- $X^{12}$ is —C≡N or —C≡C—C≡N;
- ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
- $Z^{14}$ is a single bond, —$CH_2CH_2$—, —C≡C—, —COO—, —$CF_2O$—, —$OCF_2$— or —$CH_2O$—;
- $L^{13}$ and $L^{14}$ are independently hydrogen or fluorine; and
- i is 1, 2, 3 or 4.

10. The liquid crystal composition according to claim 5, further containing at least one optically active compound and/or polymerizable compound.

11. The liquid crystal composition according to claim 5, further containing at least one antioxidant and/or ultraviolet light absorber.

12. A liquid crystal display device, including the liquid crystal composition according to claim 5.

\* \* \* \* \*